United States Patent
Zhang et al.

(10) Patent No.: US 11,505,601 B2
(45) Date of Patent: Nov. 22, 2022

(54) COMPOSITIONS AND METHODS USING A SINGLE-DOMAIN ANTIBODY BINDING TRANSFERRIN AND PROTEIN A FOR INCREASING PROTEIN HALF-LIFE IN SERUM

(71) Applicant: NANJING LEGEND BIOTECH CO., LTD., Nanjing (CN)

(72) Inventors: Yafeng Zhang, Nanjing (CN); Shu Wu, Nanjing (CN); Fei Sun, Nanjing (CN); Shuai Yang, Nanjing (CN); Chuan-Chu Chou, Westfield, NJ (US)

(73) Assignee: Nanjing Legend Biotech Co., Ltd, Nanjing (CN)

( * ) Notice: Subject to any disclaimer, the term of this patent is extended or adjusted under 35 U.S.C. 154(b) by 0 days.

(21) Appl. No.: 16/755,268

(22) PCT Filed: Oct. 11, 2017

(86) PCT No.: PCT/US2017/056125
§ 371 (c)(1),
(2) Date: Apr. 10, 2020

(87) PCT Pub. No.: WO2019/074498
PCT Pub. Date: Apr. 18, 2019

(65) Prior Publication Data
US 2022/0033481 A1 Feb. 3, 2022

(51) Int. Cl.
C07K 16/18 (2006.01)
C07K 19/00 (2006.01)
C07K 14/79 (2006.01)
A61K 39/395 (2006.01)
A61K 47/68 (2017.01)
C12N 15/63 (2006.01)

(52) U.S. Cl.
CPC .......... *C07K 16/18* (2013.01); *A61K 39/3955* (2013.01); *A61K 47/6811* (2017.08); *A61K 47/6813* (2017.08); *C07K 19/00* (2013.01); *C12N 15/63* (2013.01); *C07K 14/79* (2013.01); *C07K 2317/565* (2013.01); *C07K 2317/569* (2013.01); *C07K 2319/03* (2013.01); *C07K 2319/31* (2013.01)

(58) Field of Classification Search
CPC .. C07K 16/18; C07K 2317/569; C07K 19/00; C07K 14/79; C07K 2319/31; A61K 39/3955; A61K 47/6811
See application file for complete search history.

(56) References Cited

U.S. PATENT DOCUMENTS

| 9,193,780 B2 | 11/2015 | Hultberg et al. |
| 2010/0172894 A1 | 7/2010 | Brown et al. |
| 2016/0200830 A1 | 7/2016 | Zhang et al. |

FOREIGN PATENT DOCUMENTS

| JP | 2012507557 A | 3/2012 |
| JP | 2017095503 A | 6/2017 |
| WO | 2010056550 | 5/2010 |
| WO | 2011051327 A2 | 5/2011 |
| WO | 2015121092 A1 | 8/2015 |

OTHER PUBLICATIONS

NCBI Protein Database record for Transferrin [*Homo sapiens*], GenBank AAH59367. 1, dated Jul. 17, 2006, 2 pages as published, no author indicated.*
Benjamini et al, 1991. Immunology: A Short Course, 2nd edition, p. 40 only.*
Ferrara et al (2015. mAbs. 7(1): 32-41).*
International Search Report dated Feb. 22, 2018 from International Application No. PCT/US2017/056125.
GenBank Accession No. PH1753 Ig heavy chain V region (clone NP-12-19)—mouse (fragment), Mar. 17, 1999 [online]. [Retrieved on Feb. 7, 2018]. Retrieved from the internet: <URL:https://www.ncbi.nlm.nih.gov/protein/PH1753>.
Anonymous: "Purification of Antibody Fragments and Single Domain Antibodies With Amsphere(TM) A3 Protein A Resin", BioProcess International, Sep. 26, 2017 (Sep. 26, 2017), pp. 1-2, XP055795295, Retrieved from the Internet: URL:https://bioprocessintl.com/sponsored-content/purification-antibody-fragments-single-domain-antibodies-amsphere-a3-protein-resin/ [retrieved on Apr. 14, 2021].
Gerald Platteau et al: "Purification of antibody fragments and single domain antibodies with Amsphere (TM) A3 Protein A resin", Oct. 5, 2017 (Oct. 5, 2017), pp. 1-12, XP055712744, Retrieved from the Internet: URL:https://pdfs.semanticscholar.org/cf0e/ff622fc5cbc1d278b298eeb4148b36dc8e41.pdf [retrieved on Jul. 8, 2020].
Kevin A. Henry et al: "A Rational Engineering Strategy for Designing Protein A-Binding Camelid Single-Domain Antibodies", PLOS ONE, vol. 11, No. 9, Sep. 15, 2016 (Sep. 15, 2016), p. e0163113, XP055471386, DOI: 10.1371/journal.pone.0163113.

\* cited by examiner

*Primary Examiner* — Zachary C Howard
(74) *Attorney, Agent, or Firm* — Ice Miller LLP

(57) ABSTRACT

Novel antibodies, such as single domain antibodies (sdAbs), or antigen-binding fragments thereof that specifically bind a transferrin are described. Compositions, methods and systems for increasing the half-life of a target protein in a serum using an antibody or fragment thereof against a transferrin are also described.

14 Claims, 15 Drawing Sheets
Specification includes a Sequence Listing.

COMPOSITIONS AND METHODS USING A SINGLE-DOMAIN ANTIBODY BINDING TRANSFERRIN AND PROTEIN A FOR INCREASING PROTEIN HALF-LIFE IN SERUM

CROSS-REFERENCE TO RELATED APPLICATIONS

This application is a Section 371 of International Patent Application No. PCT/US2017/056125, filed Oct. 11, 2017, which was published on Apr. 18, 2019, under International Publication No. WO 2019/074498 A1, the disclosure which is incorporated herein by reference in its entirety.

SUBMISSION OF SEQUENCE LISTING ON ASCII TEXT FILE

This application contains a sequence listing, which is submitted electronically via EFS-Web as an ASCII formatted sequence listing with a file name "065782.3US1 Sequence Listing" and a creation date of Apr. 1, 2020 and having a size of 125 kb. The sequence listing submitted via EFS-Web is part of the specification and is herein incorporated by reference in its entirety.

FIELD OF THE INVENTION

The present inventions relates to single-domain antibodies (sdAbs) that specifically recognize transferrin and methods of making and using the same.

BACKGROUND OF THE INVENTION

Pharmacokinetics of a drug candidate is a critical parameter and often largely determines whether or not the drug candidate will be further developed into a drug or used for a therapeutic application. In particular, pharmacokinetic studies of protein- and peptide-based therapeutics, including antibodies, have demonstrated that such therapeutics have varying serum half-lives, and those peptides and proteins with a short serum half-life, although having a promising therapeutic potential, are thus often unsuitable for further drug development. For example, albumin and gamma immunoglobulins (IgGs) are known to have very long serum half-lives of up to 20 days [1]. In addition, the Fc domain of other IgGs can be engineered to alter their binding interactions to neonatal Fc receptor as a method of prolonging serum half-life [2]. However, many other natural human proteins, such as insulin, antibody fragments such as antigen binding fragments (Fabs) or single chain variable fragment (scFvs), and short peptides usually have much shorter serum half-lives ranging from minutes to approximately only 1 hour. An efficient, cost effective and safe way of extending serum half-lives of proteins and peptides with short half-lives is therefore critical for these molecules to become therapeutic drugs, diagnostic tools, etc.

Several strategies have been developed in an effort to prolong the serum half-life of proteins and other peptidic molecules that are short-lived in serum to avoid clearance of such therapeutic or diagnostic proteins from circulation. Several technologies employed to facilitate serum half-life extension of proteins and peptidic molecules include conjugation with a chemical attachment such as polyethylene glycol (i.e. pegylation) [3], fusion to the Fc region of an antibody [4] and fusion to a protein naturally having a long serum half-life, such as albumin [5]. Unfortunately, these technologies suffer from complications including complex manufacturing and characterization processes, low expression levels and undesired functions of the generated molecules.

Another approach that has been more recently developed to extend the serum half-life of proteins and other peptidic molecules employs the use of antibody fragments against serum proteins. Albumin, due mainly to its high serum concentration and long serum half-life, has been the most selected target for this purpose. An isolated domain antibody against human albumin was shown to prolong the serum half-life of interferon (IFN)-α2b after the two molecules were fused at the genetic level and expressed as a fusion protein [6, 7]. The serum half-life of the newly generated fusion protein molecule is not only longer than that of IFN-α2b, but even longer than that of the fusion protein of albumin and IFN-α2b.

Heavy chain variable domains of camelid heavy chain antibodies (HCAbs), known as $V_H H$ or single domain antibodies (sdAbs), have also been exploited for this purpose. For example, a sdAb against human albumin was shown to extend the serum half-life of an anti-TNFα sdAb fragment from less than one hour to over two days [8].

Another serum protein with a long half-life is transferrin. Transferrin is a plasma glycoprotein that transfers iron ion and has a serum concentration of approximately 3 g/L and serum half-life of 7-8 days. Thus, transferrin is an ideal fusion partner to extend the serum half-life of peptidic molecules with unsatisfactory pharmacokinetics. Studies have shown that fusion to transferrin significantly extended the serum half-life of both glucagon-like peptide 1 (GLP1) [9] and acetylcholine receptor[10].

New methods for increasing the serum half-life of proteins, and for producing proteins with improved serum half-life, that are efficient, cost-effective, and produce such proteins in high yield would facilitate the development of novel protein-based diagnostics or therapeutics. Embodiments of the present invention relate to such methods.

BRIEF SUMMARY OF THE INVENTION

The present invention relates to novel antibodies against transferrin, and particularly single domain antibodies (sdAbs) against transferrin. The present invention also relates to methods and compositions of using antibodies that specifically bind transferrin to increase the half-life of a target protein in the presence of the transferrin, and novel fusion proteins comprising the target protein having increased half-life in the presence of the transferrin.

In one general aspect, the present invention relates to a polypeptide comprising at least one immunoglobulin single domain antibody (sdAb) that specifically binds human and cynomolgus monkey serum transferrin protein and protein A resin, wherein the sdAb can be purified by protein A column and used for half-life extension fragments for short half-life proteins or fragments.

In one general aspect, the present invention relates to an isolated antibody or antigen-binding fragment thereof that specifically binds a transferrin, the antibody or antigen-binding fragment thereof comprising one or more frameworks selected from the group consisting of:
  (a) a framework 1 having an amino acid sequence selected from the group consisting of SEQ ID NO: 1-SEQ ID NO: 37;
  (b) a framework 2 having an amino acid sequence selected from the group consisting of SEQ ID NO: 91-SEQ ID NO: 127;

(c) a framework 3 having an amino acid sequence selected from the group consisting of SEQ ID NO: 181-SEQ ID NO: 217; and (d) a framework 4 having an amino acid sequence selected from the group consisting of SEQ ID NO: 271-SEQ ID NO: 307.

In another general aspect, the present invention relates to an isolated humanized antibody or antigen-binding fragment thereof that specifically binds a transferrin, the humanized antibody or antigen-binding fragment thereof comprising one or more frameworks selected from the group consisting of:

(a) a framework 1 having an amino acid sequence selected from the group consisting of SEQ ID NO: 38-SEQ ID NO: 45;

(b) a framework 2 having an amino acid sequence selected from the group consisting of SEQ ID NO: 128-SEQ ID NO: 135;

(c) a framework 3 having an amino acid sequence selected from the group consisting of SEQ ID NO: 218-SEQ ID NO: 225; and (d) a framework 4 having an amino acid sequence selected from the group consisting of SEQ ID NO: 308-SEQ ID NO: 315.

In another general aspect, the present invention relates to an isolated antibody or antigen-binding fragment thereof that specifically binds a transferrin, the antibody or antigen-binding fragment thereof comprising one or more complementarity determining regions (CDRs) selected from the group consisting of:

(a) a CDR1 having an amino acid sequence selected from the group consisting of SEQ ID NO: 46-SEQ ID NO: 82;

(b) a CDR2 having an amino acid sequence selected from the group consisting of SEQ ID NO: 136-SEQ ID NO: 172; and (c) a CDR3 having an amino acid sequence selected from the group consisting of SEQ ID NO: 226-SEQ ID NO: 262.

In another general aspect, the present invention relates to an isolated humanized antibody or antigen-binding fragment thereof that specifically binds a transferrin, the humanized antibody or antigen-binding fragment thereof comprising one or more complementarity determining regions (CDRs) selected from the group consisting of:

(a) a CDR1 having an amino acid sequence selected from the group consisting of SEQ ID NO: 83-SEQ ID NO: 90;

(b) a CDR2 having an amino acid sequence selected from the group consisting of SEQ ID NO: 173-SEQ ID NO: 180; and (c) a CDR3 having an amino acid sequence selected from the group consisting of SEQ ID NO: 263-SEQ ID NO: 270.

Preferably, the antibody or fragment thereof is a single domain antibody (sdAb). More preferably, the antibody or antibody fragment thereof is a sdAb comprising an amino acid sequence at least 90%, preferably at least 95%, more preferably 100% identical to a sequence selected from the group consisting of SEQ ID NO: 316-SEQ ID NO: 352.

In another general aspect, the present invention relates to a humanized antibody or fragment thereof that specifically binds a transferrin, the antibody or fragment thereof comprising one or more frameworks selected from the group consisting of:

(a) a framework 1 having the amino acid sequence of SEQ ID NO: 38 or SEQ ID NO: 45;

(b) a framework 2 having the amino acid sequence of SEQ ID NO: 128 or SEQ ID NO: 135;

(c) a framework 3 having the amino acid sequence of SEQ ID NO: 218 or SEQ ID NO: 225; and (d) a framework 4 having the amino acid sequence of SEQ ID NO: 308 or SEQ ID NO: 315.

In another general aspect, the present invention relates to an humanized antibody or fragment thereof that specifically binds a transferrin, the antibody or fragment thereof comprising one or more complementarity determining regions (CDRs) selected from the group consisting of:

(a) a CDR1 having the amino acid sequence of SEQ ID NO: 83 or SEQ ID NO: 90;

(b) a CDR2 having the amino acid sequence of SEQ ID NO: 173 or SEQ ID NO: 180; and (c) a CDR3 having the amino acid sequence of SEQ ID NO: 263 or SEQ ID NO: 270.

Preferably, the antibody or fragment thereof is a humanized single domain antibody (sdAb). More preferably, the humanized antibody or antibody fragment thereof is a sdAb comprising an amino acid sequence at least 90%, preferably at least 95%, more preferably 100% identical to the amino acid sequence of SEQ ID NO: 353 or SEQ ID NO: 360.

The present invention also relates to a fusion protein comprising the antibody or fragment thereof according to embodiments of the present invention, a target protein, and optionally a linker, wherein the antibody or fragment thereof is fused to the carboxyl-terminus or amino-terminus of the target protein, and the linker optionally separates the antibody and the carboxyl-terminus or amino-terminus of the target protein.

The present invention also relates to a nucleic acid molecule comprising a cDNA or synthetic DNA encoding the antibody or antigen-binding fragment thereof or a nucleic acid encoding the fusion protein according to embodiments of the present invention, and related expression vectors and host cells.

In another general aspect, the present invention relates to a method for increasing the half-life of a target protein. The method comprises:

(1) obtaining a fusion protein, wherein the fusion protein comprises an antibody or fragment thereof that specifically binds a transferrin according to an embodiment of the invention, the target protein, and optionally a linker, wherein the antibody or fragment thereof is fused to the carboxyl-terminus or amino-terminus of the target protein, and the linker optionally separates the antibody and the carboxyl-terminus or amino-terminus of the target protein; and (2) exposing the fusion protein to the transferrin, wherein the transferrin increases the half-life of the target protein in the fusion protein compared to the target protein alone.

According to an embodiment of the present invention, the fusion protein is obtained by a method comprising:

(a) obtaining an expression vector encoding the fusion protein;

(b) introducing the expression vector into a cell to obtain a recombinant cell;

(c) growing the recombinant cell under conditions to allow expression of the fusion protein; and (d) obtaining the fusion protein from the recombinant cell.

Another general aspect of the invention relates to a composition comprising an effective amount of a fusion protein, wherein the fusion protein comprises an antibody or fragment thereof that specifically binds a transferrin according to an embodiment of the invention, a target protein, and optionally a linker, wherein the antibody or fragment thereof is fused to the carboxyl-terminus or amino-terminus of the target protein, and the linker optionally separates the antibody and the carboxyl-terminus or amino-terminus of the target protein. Preferably, the composition further comprises the transferrin.

The present invention also relates to a method comprising exposing a composition according to an embodiment of the present invention to the transferrin to thereby increase the half-life of the target protein in the fusion protein.

A further aspect of the present invention relates to a system for increasing the half-life of a target protein, the system comprising:
(1) an expression vector comprising a first nucleotide sequence encoding an antibody or fragment thereof that specifically binds a transferrin according to an embodiment of the invention, and optionally a second nucleotide sequence encoding a linker, wherein the first and second nucleotide sequences are operably linked;
(2) a host cell; and
(3) the transferrin.

Other aspects, features and advantages of the invention will be apparent from the following disclosure, including the detailed description of the invention and its preferred embodiments and the appended claims.

BRIEF DESCRIPTION OF THE DRAWINGS

The foregoing summary, as well as the following detailed description of the invention, will be better understood when read in conjunction with the appended drawings. For the purpose of illustrating the invention there are shown in the drawings embodiments which are presently preferred. It should be understood, however, that the invention is not limited to the precise arrangements and instrumentalities shown. In the drawings:

FIG. 4A: SPR sensorgram of sdAb AS01274 binding to human transferrin (TfR) at varying concentrations of sdAb, i.e., 7.8125 nM, 31.25 nM, 125 nM, 500 nM and 20000 nM from the top to the bottom of the plot;

FIG. 4B: SPR sensorgram of sdAb AS01299 binding to human transferrin (TfR) at varying concentrations of sdAb, i.e., 7.8125 nM, 31.25 nM, 125 nM, 500 nM and 20000 nM from the top to the bottom of the plot;

FIG. 4C: SPR sensorgram of sdAb AS01274 binding to cynomolgus monkey transferrin (TfR) at varying concentrations of sdAb, i.e., 3.90626 nM, 15.625 nM, 62.5 nM, 250 nM and 1000 nM from the top to the bottom of the plot;

FIG. 4D: SPR sensorgram of sdAb AS01299 binding to cynomolgus monkey transferrin at varying concentrations of sdAb, i.e., 3.90626 nM, 15.625 nM, 62.5 nM, 250 nM and 1000 nM from the top to the bottom of the plot.

FIG. 5A, binding of heat treated AS01274 sdAb and AS01299 sdAb for human transferrin; and FIG. 5B, binding of heat treated AS01274 sdAb and AS01299 sdAb for cynomolgus monkey transferrin.

FIG. 8A: SPR sensorgram of sdAb AS01274 binding to human transferrin at varying concentrations of sdAb, i.e., 0.375 nM, 0.75 nM, 1.5 nM, 3 nM, 6 nM and 12 nM from the top to the bottom of the plot;

FIG. 8B: SPR sensorgram of sdAb AS01274VHa binding to human transferrin at varying concentrations of sdAb, i.e., 0.75 nM, 1.5 nM, 3 nM, 6 nM and 12 nM from the top to the bottom of the plot;

FIG. 8C: SPR sensorgram of sdAb AS01274VHa-A49 binding to human transferrin at varying concentrations of sdAb, i.e., 0.75 nM, 1.5 nM, 3 nM, 6 nM and 12 nM from the top to the bottom of the plot;

FIG. 8D: SPR sensorgram of sdAb AS01274 binding to cynomolgus monkey transferrin at varying concentrations of sdAb, i.e., 0.1875 nM, 0.375 nM, 0.75 nM, 1.5 nM and 3 nM from the top to the bottom of the plot;

FIG. 8E: SPR sensorgram of sdAb AS01274VHa binding to cynomolgus monkey transferrin at varying concentrations of sdAb, i.e., 0.375 nM, 0.75 nM, 1.5 nM, 3 nM and 6 nM from the top to the bottom of the plot;

FIG. 8F: SPR sensorgram of sdAb AS01274VHa-A49 binding to cynomolgus monkey transferrin at varying concentrations of sdAb, i.e., 0.75 nM, 1.5 nM, 3 nM, 6 nM and 12 nM from the top to the bottom of the plot;

FIG. 9A: SPR sensorgram of sdAb AS01299 binding to human transferrin at varying concentrations of sdAb, i.e., 0.375 nM, 0.75 nM, 1.5 nM, 3 nM, 6 nM and 12 nM from the top to the bottom of the plot;

FIG. 9N: SPR sensorgram of sdAb AS01274VH4-L47 binding to cynomolgus monkey transferrin at varying concentrations of sdAb, i.e., 0.1875 nM, 0.375 nM, 0.75 nM, 1.5 nM, 3 nM and 6 nM from the top to the bottom of the plot.

DETAILED DESCRIPTION OF THE INVENTION

Figure 1:
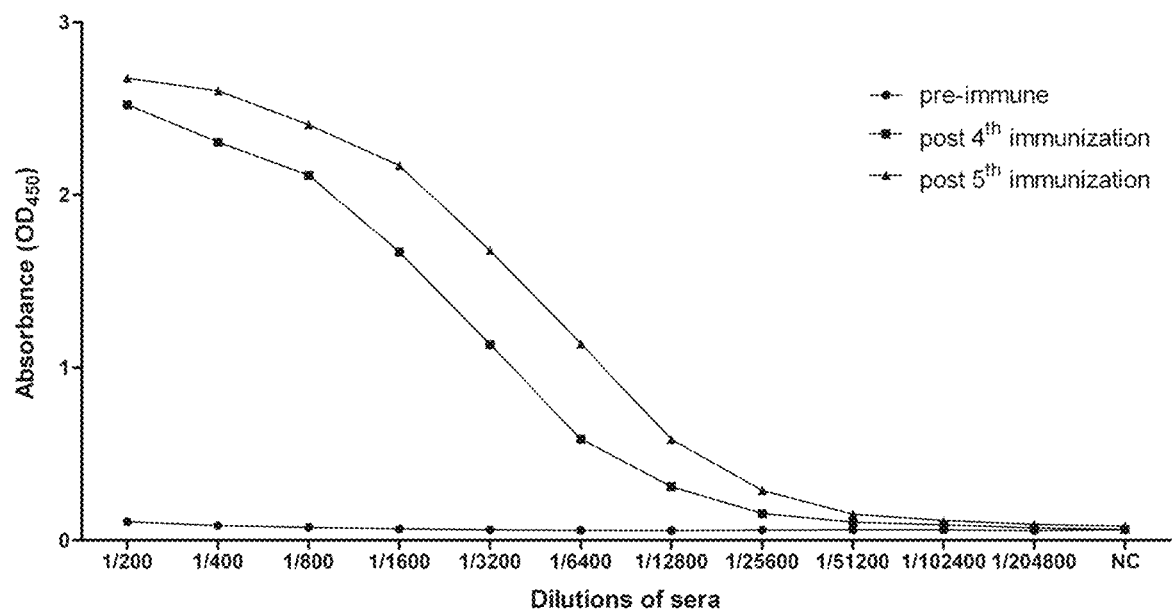
FIG. 1 is a graph showing the immune response of llama against human transferrin after being immunized with an antigen.

Various publications are cited or described in the background and throughout the specification and each of these references is herein incorporated by reference in its entirety. Discussion of documents, acts, materials, devices, articles or the like which has been included in the present specification is for the purpose of providing context for the present invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. It must be noted that as used herein and in the appended claims, the singular forms "a," "an," and "the" include plural reference unless the context clearly dictates otherwise.

One of ordinary skill in the art will be familiar with the structure of an antibody. The light and heavy chains each contain a variable region that is responsible for binding the target antigen. The variable region contains the antigen binding determinants of the molecule, thus determining the specificity of an antibody for its target antigen. The variable regions of the light and heavy chains each comprise three complementarity determining regions (CDRs).

As used herein "complementarity determining region" and "CDR" refer to an amino acid sequence of a variable region of a heavy or light chain of an antibody that contributes to specific recognition of, and binding specificity for, the antigen. The CDRs are referred to as CDR1, CDR2, and CDR3. According to embodiments of the present invention, at least one of the sequences of CDR1, CDR2, and CDR3 contributes to specific recognition of, and binding specificity for, an antibody or fragment thereof against transferrin, and preferably against human transferrin.

An "antibody fragment" as used herein includes any suitable antigen-binding antibody fragment. For example, an antibody fragment can comprise a single-chain variable region. According to embodiments of the present invention, an antibody is preferably a single-domain antibody (sdAb).

As used herein, "single-domain antibody" or "sdAb" refers to the antigen-binding site of a heavy-chain antibody (HCAb) of camelids, such as camel, llama and alpaca, and sharks, which is naturally devoid of light chains. The antigen-binding site of HCAb of camelids is formed by a single variable domain designated $V_HH$. The sdAbs usually exist as monomeric proteins having relatively small sizes. A sdAb according to the invention has three CDRs (CDR1, CDR2, and CDR3).

As used herein, "antibody or fragment thereof against transferrin," "antibody or fragment thereof that specifically binds transferrin," and "transferrin antibody," shall all have the same meaning, and refer to an antibody or fragment thereof, that binds specifically to transferrin.

As used herein, "sdAb against transferrin," "sdAb that specifically binds transferrin," and "transferrin sdAb," shall all have the same meaning, and refer to a single domain antibody that binds specifically to transferrin.

"Protein A" is a 40-60 kDa surface protein originally found in the cell wall of Staphylococcus aureus. It binds immunoglobulins, most notably IgGs, from many mammalian species through an interaction of two α-helices of its IgBDs (A, B, C, D, E) with the CH2 and CR3 domains in the Fc fragment of an Ig molecule. Protein A binds with high affinity to human IgG1 and IgG2 as well as mouse IgG2a and IgG2b but only with moderate affinity to human IgM, IgA and IgE as well as to mouse IgG3 and IgG1. Protein A also binds to the antibody variable region in the case of the human VH3 family.

"Humanized" forms of non-human (e.g., llama or camelid) antibodies are chimeric antibodies that contain minimal sequence derived from non-human immunoglobulin. In some embodiments, a humanized antibody is a human immunoglobulin (recipient antibody) in which residues from a CDR of the recipient are replaced by residues from a CDR of a non-human species (donor antibody) such as mouse, rat, rabbit, camel, llama, alpaca, or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin.

As used herein, "binds specifically to" or "against" when used in connection with an antibody or fragment thereof and transferrin refers to the binding or interaction between the antibody or fragment thereof, such as a sdAb, and the transferrin. An antibody or fragment thereof, such as a sdAb, according to the invention binds to a transferrin with a dissociation constant ($K_D$) of between $10^{-6}$ and $10^{-9}$ M, or less, and preferably with a dissociation constant of less than $10^{-9}$ M. The term "$K_D$" refers to the dissociation constant, which is obtained from the ratio of Kd to Ka (i.e., Kd/Ka) and is expressed as a molar concentration (M). $K_D$ values for antibodies can be determined using methods in the art in view of the present disclosure. For example, the $K_D$ of an antibody can be determined by using surface plasmon resonance, such as by using a biosensor system, e.g., a Biacore® system, or by using bio-layer interferometry technology, such as a Octet RED96 system.

Any method known in the art can be used for determining specific antigen-antibody binding including, for example, surface plasmon resonance (SPR), scatchard analysis and/or competitive binding assays, such as radioimmunoassay (RIA), enzyme immunoassays (EIA) and sandwich competition assays, and the different variants thereof known in the art, as well as other techniques mentioned herein. Methods for determining the binding affinities or dissociation constants are known to those skilled in the art.

Any method known in the art can be used for characterizing an antibody or sdAb according to the invention, such as SDS-polyacrylamide gel electrophoresis (PAGE), circular dichroism (CD), size exclusion chromatography (SEC), etc. Methods for characterizing proteins, i.e. determining the oligomeric state, melting temperature, molecular weight, purity, etc., are known to those skilled in the art.

As used herein, the "half-life" of a protein or polypeptide refers to the time taken for the concentration of the polypeptide to be reduced by 50% in an assay conducted in vivo or in vitro. The reduction can be caused by degradation, clearance or sequestration of the polypeptide in the assay. The half-life of a polypeptide can be determined in any manner known in the art in view of the present disclosure, such as by pharmacokinetic analysis. For example, to measure the half-life of a protein or polypeptide in vivo, a suitable dose of the polypeptide is administered to a warm-blooded animal (i.e. to a human or to another suitable mammal, such as a mouse, rabbit, rat, pig, dog, or a primate); blood samples or other samples from the animal are collected; the level or concentration of the protein or polypeptide in the sample is determined; and the time until the level or concentration of the polypeptide has been reduced by 50% compared to the initial level upon dosing is calculated based on measured data. See, e.g., Kenneth, A et al., Chemical Half-life of Pharmaceuticals: A Handbook for Pharmacists and Peters et al., Pharmacokinetic analysis: A Practical Approach (1996).

As used herein, "an increase in half-life" or "longer half-life" refers to an increase in any one of the parameters used to describe the protein half-life, such as the $t½-\alpha$, $t½-\beta$ and the area under the curve (AUC), any two of these parameters, or essentially all of these parameters, as compared to a control.

As used herein, a "fusion tag" is a polypeptide sequence that can be operably linked to a target protein or polypeptide to generate a fusion protein for the ease of subsequent manipulation, such as for the expression, purification, in vitro and in vivo analysis and characterization of the protein, or diagnostic or therapeutic application. A fusion tag may exhibit one or more properties. For example, the fusion tag may selectively bind to a purification medium that contains a binding partner for the fusion tag and allows the operably linked target protein or fusion protein to be easily purified. The fusion tag can be, for example, glutathione S-transferase (GST), maltose binding protein, polyhistidine (His-tag), FLAG-tag, avidin, biotin, streptavidin, chitin binding domain, a ligand of a cellular receptor, the Fc region of an antibody, green fluorescent protein, etc.

The present invention relates to antibodies or fragments thereof against transferrin and methods of using antibodies or fragments thereof against a transferrin to increase the half-life of a target protein, i.e., by obtaining a fusion protein with a target protein, and exposing the fusion protein to the transferrin, for example, in a serum. In a particular embodiment, the invention relates to novel sdAbs against transferrin and their uses.

Accordingly, in one general aspect, the present invention relates to a polypeptide comprising at least one immunoglobulin single domain antibody (sdAb) that specifically binds human and cynomolgus monkey serum transferrin protein and protein A resin, wherein the sdAb can be purified by protein A column and used for half-life extension fragments for short half-life proteins or fragments.

Accordingly, in one general aspect, the present invention relates to an isolated antibody or fragment and humanized antibody or fragment thereof that specifically binds a transferrin comprise an amino acid sequence SEQ ID NO: 316-SEQ ID NO: 360.

Accordingly, in another general aspect, the present invention provides an isolated antibody or fragment and a humanized antibody or fragment thereof that specifically binds a transferrin, the antibody or fragment thereof comprising:

(a) a framework 1 having an amino acid sequence selected from the group consisting of SEQ ID NO: 1-SEQ ID NO: 45;

(b) a framework 2 having an amino acid sequence selected from the group consisting of SEQ ID NO: 91-SEQ ID NO: 135;

(c) a framework 3 having an amino acid sequence selected from the group consisting of SEQ ID NO: 181-SEQ ID NO: 225; and (d) a framework 4 having an amino acid sequence selected from the group consisting of SEQ ID NO: 271-SEQ ID NO: 315.

Accordingly, in another general aspect, the present invention provides an isolated antibody or fragment or a humanized antibody or fragment thereof that specifically binds a transferrin, the antibody or fragment thereof comprising:

(a) a framework 1 having an amino acid sequence selected from the group consisting of
  (1) SEQ ID NO: 1-SEQ ID NO: 45; and
  (2) amino acid sequences that have 4, 3, 2, or 1 amino acid(s) difference with the amino acid sequences of SEQ ID NO:1-SEQ ID NO:45;
(b) a framework 2 having an amino acid sequence selected from the group consisting of
  (1) SEQ ID NO: 91-SEQ ID NO: 135; and
  (2) amino acid sequences that have 4, 3, 2, or 1 amino acid(s) difference with the amino acid sequences of SEQ ID NO:91-SEQ ID NO:135
(c) a framework 3 having an amino acid sequence selected from the group consisting of
  (1) SEQ ID NO: 181-SEQ ID NO: 225; and
  (2) amino acid sequences that have 4, 3, 2, or 1 amino acid(s) difference with the amino acid sequences of SEQ ID NO: 181-SEQ ID NO:225; and
(d) a framework 4 having an amino acid sequence selected from the group consisting of
  (1) SEQ ID NO: 271-SEQ ID NO: 315; and
  (2) amino acid sequences that have 4, 3, 2, or 1 amino acid(s) difference with the amino acid sequences of SEQ ID NO:271-SEQ ID NO:315.

Accordingly, in another general aspect, the present invention provides an isolated antibody or fragment and a humanized antibody or fragment thereof that specifically binds a transferrin, the antibody or fragment thereof comprising:
  (a) a complementarity determining region (CDR)1 having an amino acid sequence selected from the group consisting of SEQ ID NO: 46-SEQ ID NO: 90;
  (b) a CDR2 having an amino acid sequence selected from the group consisting of SEQ ID NO: 136-SEQ ID NO: 180; and
  (c) a CDR3 having an amino acid sequence selected from the group consisting of SEQ ID NO: 226-SEQ ID NO: 270.

Accordingly, in another general aspect, the present invention provides an isolated antibody or fragment and a humanized antibody or fragment thereof that specifically binds a transferrin, the antibody or fragment thereof comprising:
  (a) a complementarity determining region (CDR)1 having an amino acid sequence selected from the group consisting of
    (1) SEQ ID NO: 46-SEQ ID NO: 90; and
    (2) amino acid sequences that have 4, 3, 2, or 1 amino acid(s) difference with the amino acid sequences of SEQ ID NO:46-SEQ ID NO:90; and/or
  (b) a CDR2 having an amino acid sequence selected from the group consisting of
    (1) SEQ ID NO: 136-SEQ ID NO: 180; and
    (2) amino acid sequences that have 4, 3, 2, or 1 amino acid(s) difference with the amino acid sequences of SEQ ID NO:136-180; and/or
  (c) a CDR3 having an amino acid sequence selected from the group consisting of
    (1) SEQ ID NO: 226-SEQ ID NO: 270; and
    (2) amino acid sequences that have 4, 3, 2, or 1 amino acid(s) difference with the amino acid sequences of SEQ ID NO:226-SEQ ID NO:270.

According to embodiments of the present invention, an isolated antibody, preferably a sdAb, or fragment thereof, comprises a framework 1, CDR1, framework 2, CDR2, framework3, CDR 3, and framework 4 described above.

According to embodiments of the present invention, an isolated antibody or fragment thereof that specifically binds a transferrin has an affinity ($K_D$) for transferrin that is $10^{-6}$ to $10^{-9}$ M or less, and preferably having an affinity lower than $10^{-9}$ M. In a most preferred embodiment, an isolated antibody or fragment thereof according to the invention has a $K_D$ for transferrin that is in the subnanomolar range, for example, in the picomolar range, such as 1-10 pM, 15, 20, 30, 40, 50, 60, 70, 80, 90 or 100 pM.

Preferably, an isolated antibody or fragment thereof according to an embodiment of the present invention comprises a CDR1 amino acid sequence of SEQ ID NO:46, a CDR2 amino acid sequence of SEQ ID NO:136, and a CDR3 amino acid sequence of SEQ ID NO:226. In yet another particular embodiment, an isolated antibody or fragment thereof according to an embodiment of the present invention comprises a CDR1 amino acid sequence of SEQ ID NO:62, a CDR2 amino acid sequence of SEQ ID NO:152, and a CDR3 amino acid sequence of SEQ ID NO:242.

According to embodiments of the present invention, an antibody or fragment thereof, such as a sdAb, that specifically binds transferrin can comprise an amino acid sequence at least 90%, preferably at least 95%, more preferably 100%, identical to an amino acid sequence selected from the group consisting of SEQ ID NOs: 316-352.

According to a preferred embodiment of the present invention, an antibody or fragment thereof that specifically binds transferrin is a sdAb. For example, a sdAb according to the invention that specifically binds transferrin can be a camelid $V_HH$ antibody.

In a particularly preferred embodiment of the present invention, a sdAb that specifically binds transferrin can comprise an amino acid sequence at least 90%, preferably at least 95%, more preferably 100%, identical to the amino acid sequence of AS01274 (QVQLVESGG-GLVQPGGSLRLSCVASGSIASIAT-MAWYRQAPGQQRELVAGITRGGS TKY-ADSVKGRFTISRDNAKNTLYLQMNSLKPDDTAVYYC-TDYSRKYYQDYWGQGT QVTVSS (SEQ ID NO: 316)) or an amino acid sequence at least 90%, preferably at least 95% or 100%, identical to the amino acid sequence of

AS01299
(QVQLVESGGGLVQPGGSLRLSCAASGSIFSIATMAWYRQAPGKQRELVA

GITRSGSTNYRDSVKGRFTISRDNAKNTMYLQMNSLKPEDTAVYYCTDYS

SRYYHDYWGQGTQVTVSS (SEQ ID NO: 332)).

In a particularly preferred embodiment of the present invention, a sdAb that specifically binds protein A can comprise an amino acid sequence at least 90%, preferably at least 95%, more preferably 100%, identical to the amino acid sequence selected from the group consisting of

AS01290
(SEQ ID NO: 325)
(QVQLVESGGGLVQAGGSLRLSCAASRSISTLRFMAWYRQAPGEQRELVA

AETSAGRLTYADSVKGRFTVSRDNAKDTIDLQMNSLKPEDTGVYYCAARG

LADYWGQGTQVTVSS),

AS01274
(SEQ ID NO: 316)
(QVQLVESGGGLVQPGGSLRLSCVASGSIASIATMAWYRQAPGQQRELVA

GITRGGSTKYADSVKGRFTISRDNAKNTLYLQMNSLKPDDTAVYYCTDYS

RKYYQDYWGQGTQVTVSS),

AS01284
(SEQ ID NO: 321)
(QVQLVESGGGLVQAGGSLRLSCAASGSIRPLRFMAWYRQAPGNQRGLVA

AETSGGTIRYADSVKGRFTISRDNAKNTMYLQMNSLKPEDTAVYYCAARD

LDDYWGQGIQVTVSS),

AS01299
(SEQ ID NO: 332)
(QVQLVESGGGLVQPGGSLRLSCAASGSIFSIATMAWYRQAPGKQRELVA

GITRSGSTNYRDSVKGRFTISRDNAKNTMYLQMNSLKPEDTAVYYCTDYS

SRYYHDYWGQGTQVTVSS),

AS01313
(SEQ ID NO: 343)
(QVKLEESGGGLVQAGGSLRLSCAASGRTFSSHTMGWFRQPPGKEREFVA

VIHWSGASTYYTDSVKGRFTISRDNAKNTVYLQMNSLKPEDTAIYYCAAE

VPVSTWPPTEYSWWGQGTQVTVSS),
and

AS02360
(SEQ ID NO: 349)
(QVQLVESGGGLVQPGGSLRLSCAASGSIASINTMAWYRQSPGKQRELVA

GITRGGSTNYADSVKGRFTISRDNAKNTVYLQMNSLKPEDTAVYYCTDYS

LGYYQDYWGQGTQVTVSS).

In a particularly preferred embodiment of the present invention, the sdAb is a humanized sdAb, wherein the humanized sdAb specifically binds transferrin and comprises an amino acid sequence at least 90%, preferably at least 95%, more preferably 100%, identical to the amino acid sequence of AS01274VHa (EVQLVESGGGLVQPGGSLRLSCAASGSIASIATMAWYRQAPGKGLELVAGITRGGS TKYADSVKGRFTISRDNSKNTLYLQMNSLRAEDTAVYYCTDYSRKYYQDYWGQGT LVTVSS (SEQ ID NO: 353)) or an amino acid sequence at least 90%, preferably at least 95% or 100%, identical to AS01274VHa-A49
(EVQLVESGGGLVQPGGSLRLSCAASGSIASIATMAWYRQAPGKGLELVS

GITRGGSTKYADSVKGRFTISRDNSKNTLYLQMNSLRAEDTAVYYCTDYS

RKYYQDYWGQGTLVTVSS (SEQ ID NO: 355)).

In a particularly preferred embodiment of the present invention, the sdAb is a humanized sdAb, wherein the humanized sdAb specifically binds transferrin and comprises an amino acid sequence at least 90%, preferably at least 95%, more preferably 100%, identical to the amino acid sequence of AS01299VH3a
(EVQLVESGGGLVQPGGSLRLSCAASGSIFSIATMAWYRQAPGKGLELVA

GITRSGSTNYRDSVKGRFTISRDNSKNTMYLQMNSLRAEDTAVYYCTDYS

SRYYHDYWGQGTLVTVSS (SEQ ID NO: 354));

or an amino acid sequence at least 90%, preferably at least 95% or 100%, identical to AS01299VH3a-A49
(EVQLVESGGGLVQPGGSLRLSCAASGSIFSIATMAWYRQAPGKGLELVS

GITRSGSTNYRDSVKGRFTISRDNSKNTMYLQMNSLRAEDTAVYYCTDYS

SRYYHDYWGQGTLVTVSS (SEQ ID NO: 356));

or an amino acid sequence at least 90%, preferably at least 95% or 100%, identical to AS01299VH3a-L47
(EVQLVESGGGLVQPGGSLRLSCAASGSIFSIATMAWYRQAPGKGLEWVA

GITRSGSTNYRDSVKGRFTISRDNSKNTMYLQMNSLRAEDTAVYYCTDYS

SRYYHDYWGQGTLVTVSS (SEQ ID NO: 357));

or an amino acid sequence at least 90%, preferably at least 95% or 100%, identical to AS01299VH3a-M78
(EVQLVESGGGLVQPGGSLRLSCAASGSIFSIATMAWYRQAPGKGLELVA

GITRSGSTNYRDSVKGRFTISRDNSKNTLYLQMNSLRAEDTAVYYCTDYS

SRYYHDYWGQGTLVTVSS (SEQ ID NO: 358));

or an amino acid sequence at least 90%, preferably at least 95% or 100%, identical to

AS01299VH4
(EVQLVESGGGLVQPGGSLRLSCAASGSIFSIATMAWYRQAPGKGLELVS

GITRSGSTNYRDSVKGRFTISRDNSKNTLYLQMNSLRAEDTAVYYCTDYS

SRYYHDYWGQGTLVTVSS (SEQ ID NO: 359));

or an amino acid sequence at least 90%, preferably at least 95% or 100%, identical to

AS01299VH4-L47
(EVQLVESGGGLVQPGGSLRLSCAASGSIFSIATMAWYRQAPGKGLEWVS

GITRSGSTNYRDSVKGRFTISRDNSKNTLYLQMNSLRAEDTAVYYCTDYS

SRYYHDYWGQGTLVTVSS (SEQ ID NO: 360)).

The present inventions also provides a nucleic acid comprising a complementary DNA (cDNA) sequence encoding an antibody or fragment thereof according to an embodiment of the invention. Also provided are vectors comprising the nucleic acid molecule, particularly expression vectors, and recombinant host cells comprising the vectors that can subsequently be used for downstream applications such as expression, purification, etc. The nucleic acid molecules, vectors and host cells can be obtained using methods known in the art in view of the present disclosure.

According to embodiments of the present invention, a nucleic acid molecule comprises a cDNA or synthetic DNA sequence encoding an amino acid sequence at least 90%, preferably at least 95%, more preferably 100%, identical to an amino acid sequence selected from the group consisting of SEQ ID NOs: 316-360.

As used herein, a "cDNA or synthetic DNA" refers to a DNA molecule that is different from a naturally occurring DNA molecule in at least one of the nucleotide sequence and the physical or chemical property of the DNA molecule. For example, the "cDNA or synthetic DNA" can be different from the naturally occurring DNA in nucleotide sequence by not containing one or more introns present in the natural genomic DNA sequence. The "cDNA or synthetic DNA"

can also be different from a naturally occurring DNA in one or more physical or chemical properties, such as having a different DNA modification, regardless of whether the "cDNA or synthetic DNA" comprises the same or different nucleotide sequence as that of the naturally occurring DNA.

As used herein, "DNA modification" refers to any modification to the DNA, such as by independently attaching to one or more nucleotides of the DNA one or more biochemical functional groups (such as a methyl group, phosphate group, etc.). Different host cells can have different DNA modification systems, thus producing different DNA molecules even through the DNA molecules can have identical nucleotide sequence.

A "cDNA or synthetic DNA" can be made by any method in vivo or in vitro so long as the obtained "cDNA or synthetic DNA" is distinguishable from a naturally occurring DNA molecule. For example, a "cDNA" can be made from a messenger RNA (mRNA) template in a reaction catalyzed by the enzymes reverse transcriptase and DNA polymerase, or RNA-dependent DNA polymerase. In one embodiment, a "cDNA" can be made and amplified via a reverse transcriptase polymerase chain reaction (RT-PCR) with the desired mRNA template and DNA primers. A "synthetic DNA" can be made in vitro using any method known in the art. A "synthetic DNA" can also be made in vivo in a host cell that does not naturally contain a nucleic acid molecule having the identical nucleotide sequence as that of the "synthetic DNA," such that the "synthetic DNA" made by the host cell is distinguishable from any naturally occurring DNA sequence in at least one or more physical or chemical properties, such as DNA methylation.

An antibody or fragment thereof according to embodiments of the invention can be produced recombinantly from a recombinant host cell using methods known in the art in view of the present disclosure.

The recombinantly produced antibody or fragment thereof can be different from the naturally occurring antibody or fragment thereof, for example, in posttranslational modification of amino acids. As used herein, "posttranslational modification of amino acids" refers to any modification to the amino acids after translation of the amino acids, such as by attaching to one or more amino acids independently one or more biochemical functional groups (such as acetate, phosphate, various lipids and carbohydrates), changing the chemical nature of an amino acid (e.g. citrullination), or making structural changes (e.g. formation of disulfide bridges).

Embodiments of the present invention also relate to methods of recombinantly expressing and purifying an antibody or fragment thereof that specifically binds transferrin. According to embodiments of the present invention, the method comprises obtaining an expression vector encoding an antibody or fragment thereof according to an embodiment of the invention, introducing the expression vector into a host cell to obtain a recombinant cell, growing the recombinant cell under conditions that allow expression of the antibody or fragment thereof, and obtaining the antibody or fragment thereof from the recombinant cell. The antibody or fragment thereof that specifically binds transferrin can be isolated by applying the lysate, supernatant, or periplasmic extract of the recombinant cell comprising the antibody or fragment thereof, to an affinity column associated with the transferrin.

In another embodiment, the antibody or fragment thereof that specifically binds transferrin further comprises a fusion tag that facilitates purification of the antibody or fragment thereof from the recombinant cell, by for example, applying the lysate, supernatant, or periplasmic extract of the recombinant cell comprising the antibody or fragment thereof, to an affinity column associated with a binding partner of the fusion tag.

Antibodies or fragments thereof, and particularly sdAbs, according to embodiments of the invention that specifically bind transferrin have high affinity for transferrin (e.g., picomolar range) and a longer half-life in a serum supplemented with transferrin, as compared to the half-life in a serum that is not supplemented with the transferrin. Without wishing to be bound by theory, it is believed that the binding interaction between the antibody or fragment thereof, such as sdAb, and the transferrin contributes to the longer half-life of the antibody or fragment thereof in a serum. Such antibody or fragment thereof can thus be used to increase the half-life of a target protein fused to the antibody or fragment in a serum or a composition comprising the transferrin.

Thus, in another general aspect, the present invention relates to a method of increasing the half-life of a target protein in a serum. The method comprises (1) obtaining a fusion protein, wherein the fusion protein comprises an antibody or fragment thereof that specifically binds a transferrin, the target protein, and optionally a linker, wherein the antibody or fragment thereof is fused to the carboxyl-terminus or amino-terminus of the target protein, and the linker optionally separates the antibody and the carboxyl-terminus or amino-terminus of the target protein; and (2) exposing the fusion protein to the transferrin, wherein the transferrin increases the half-life of the target protein in the fusion protein compared to the target protein alone.

According to embodiments of the present invention, the transferrin used in the exposing step can be present in any composition, including a serum or a buffered composition made in vitro. Preferably, the fusion protein is exposed to the transferrin by administering it to a serum comprising the transferrin.

According to embodiments of the present invention, when exposed to the transferrin, the fusion protein has an increased half-life, as determined, for example by measuring the half-life, as compared to the target protein alone. The fusion protein can optionally contain a linker that fuses the target protein to the antibody or fragment thereof, and also functions to separate the target protein from the antibody or fragment thereof. Linkers that can be used to fuse two protein molecules together will be well known to those skilled in the art in view of the present disclosure.

The antibody or fragment thereof can be fused to the target protein by any method known in the art, such as, for example, via genetic fusion or covalent linkage, in view of the present disclosure. The antibody or fragment thereof can be linked to either the amino-terminus or the carboxyl terminus of the target protein.

Preferably, the fusion protein comprises an antibody or fragment thereof according to embodiments of the present invention. For example, the antibody or fragment thereof comprises an amino acid sequence selected from the group consisting of the amino acid sequence of CDR1 having an amino acid sequence selected from the group consisting of SEQ ID NO: 46-SEQ ID NO: 90, the amino acid sequence of CDR2 having an amino acid sequence selected from the group consisting of SEQ ID NO: 136-SEQ ID NO: 180, and the amino acid sequence of CDR3 having an amino acid sequence selected from the group consisting of SEQ ID NO: 226-SEQ ID NO: 270. More preferably, the antibody or fragment thereof of the fusion protein is a sdAb and even more preferably is a sdAb comprising an amino acid sequence at least 90%, preferably at least 95%, more preferably 100%, identical to an amino acid sequence selected from AS01274 (SEQ ID NO: 316) or AS01299 (SEQ ID NO: 332). Most preferably, the antibody or fragment thereof of the fusion protein is a sdAb comprising an amino acid sequence at least 90%, preferably at least 95%, more preferably 100%, identical to an amino acid sequence selected from AS01274VHa (SEQ ID NO: 353), AS01299VH3a (SEQ ID NO: 354), AS01274VHa-A49 (SEQ ID NO: 355), AS01299VH3a-A49 (SEQ ID NO: 356), AS01299VH3a-L47 (SEQ ID NO: 357), AS01299VH3a-M78 (SEQ ID NO: 358), AS01299VH4 (SEQ ID NO: 359), or AS01299VH4-L47 (SEQ ID NO: 360).

According to embodiments of the present invention, the target protein is a peptide or polypeptide, such as a therapeutic polypeptide, a polypeptide that can be used for a diagnostic purpose, or a polypeptide for structural-activity studies. For example, the target protein can be an antibody, peptide, or any other polypeptide that has been or will be developed or used for a therapeutic or diagnostic purpose, or a polypeptide subject to structural and/or functional analysis. Preferably, the target protein is a therapeutic peptide or polypeptide that is unstable in serum and in need of increased serum half-life to be used for therapeutic, diagnostic purposes, etc.

The fusion proteins according to embodiments of the present invention can be used for various purposes using methods known in the art in view of the present disclosure. For example, a fusion protein can be used for assaying the affinity of the target protein to a binding partner, e.g., for drug screening or target identification purposes. It can also be used in a diagnostic method, particularly if the method involves administering the target protein to the serum. It can further be used for therapeutic purposes, particularly if the target protein is known to be unstable in serum.

Another general aspect of the invention relates to a composition comprising an effective amount of a fusion protein, wherein the fusion protein comprises an antibody or fragment thereof that specifically binds a transferrin, a target protein, and optionally a linker, wherein the antibody or fragment thereof is fused to the carboxyl-terminus or amino-terminus of the target protein, and the linker optionally separates the antibody and the carboxyl-terminus or amino-terminus of the target protein. Preferably, the composition further comprises the transferrin, which increases the half-life of the fusion protein in the composition. The composition can further comprise a pharmaceutically acceptable carrier, which can comprise any carrier that is suitable for pharmaceutical or diagnostic purposes. Depending on the use, the effective amount can be the amount of the fusion protein that is effective to provide a therapeutic or diagnostic use of the target protein as part of the fusion.

A composition according to an embodiment of the present invention can be used in vivo or in vitro for any purpose. The present invention relates to a method comprising exposing a composition according to an embodiment of the present invention to the transferrin to thereby increase the half-life of the target protein in the fusion protein.

In one embodiment, the present invention relates to a method comprising exposing a composition according to an embodiment of the present invention to the transferrin used in the fusion protein, for example, by administering the composition to a serum comprising transferrin, in vivo or in vitro for identifying a diagnostic or therapeutic agent.

In another embodiment, the present invention relates to a method comprising administering a composition according to an embodiment of the present invention to a subject in need of treatment by the target protein, wherein the composition comprises a therapeutically effective amount of a fusion protein comprising an antibody or fragment thereof that specifically binds the human transferrin and a target protein.

In yet another embodiment, the present invention relates to a method comprising administering the composition to a subject in need of a diagnosis by the target protein, wherein the composition comprises a diagnostically effective amount of the fusion protein.

Embodiments of the present invention also relate to compositions comprising a fusion protein according to the invention, and methods for increasing the half-life of a target protein in a composition. A method for increasing the half-life of a target protein in a composition comprises obtaining a fusion protein, preferably isolated fusion protein, comprising an antibody or fragment thereof against a transferrin, the target protein and an optional linker, wherein the antibody or fragment thereof is fused to the carboxyl-terminus or amino-terminus of the target polypeptide, and the optional linker separates the antibody or fragment thereof and the carboxyl-terminus or amino-terminus of the target polypeptide; and exposing the fusion protein to the transferrin in the composition, wherein the fusion protein has a longer half-life than the target protein alone in the composition.

Without wishing to be bound by theory, it is believed that the specific binding between the antibody or fragment thereof in the fusion protein and the transferrin in a composition or a serum contributes to increased half-life of the target protein.

Embodiments of the present invention also provides methods for obtaining a target protein having increased serum half-life, and for expressing and purifying a fusion protein comprising an antibody or fragment thereof that binds to a transferrin and a target protein.

According to embodiments of the present invention, a method for obtaining a target protein having increased serum half-life comprises:
(a) obtaining an expression vector encoding a fusion protein comprising an antibody or fragment thereof that specifically binds a transferrin, the target protein, and an optional linker, wherein the antibody or fragment thereof is fused to the carboxyl-terminus or amino-terminus of the target protein, and the optional linker separates the antibody and the carboxyl-terminus or amino-terminus of the target protein;
(b) introducing the expression vector of step (a) into a cell to obtain a recombinant cell;
(c) growing the recombinant cell under conditions to allow expression of the fusion protein; and
(d) obtaining the fusion protein from the recombinant cell.

Expression vectors encoding the fusion protein and recombinant cells expressing the fusion protein can be constructed using methods known in the art in view of the present disclosure. Any host cell suitable for recombinant production of the fusion protein can be used such as a mammalian cell, plant cell, yeast cell, or bacterial cell. Preferably, the host cell is a bacterial cell and is *Escherichia coli*. Any method for obtaining the fusion protein from the recombinant cell can be used in view of the present disclosure including, but not limited to, column chromatography such as affinity chromatography.

In one embodiment, the fusion protein can be obtained from a recombinant cell and purified by utilizing the specific interaction between the portion of the fusion protein comprising the antibody or fragment thereof that specifically binds transferrin, and transferrin, to obtain the fusion protein from the recombinant cell.

In another embodiment, the fusion protein can further comprise a fusion tag at the amino-terminus or carboxyl-terminus of the fusion protein to facilitate obtaining and purifying the fusion protein from the recombinant cell. For example, the lysate, periplasmic extract, or supernatant of the recombinant cell comprising the fusion protein can be obtained and applied to a column associated with the appropriate binding partner of the fusion tag. In a particular and non-limiting example, the fusion protein can further comprise a His-tag and the lysate, periplasmic extract, or supernatant of the recombinant cell comprising the fusion protein can be obtained and applied to a nickel column to obtain the fusion protein from the recombinant cell. The column can then be washed, and the fusion protein eluted from the column under the appropriate buffering conditions to obtain the fusion protein.

Another general aspect of the present invention relates to a system for increasing the half-life of a target protein, comprising
(1) an expression vector comprising a first nucleotide sequence encoding an antibody or fragment thereof that specifically binds a transferrin, and optionally a second nucleotide sequence encoding a linker, wherein the first and second nucleotide sequences are operably linked;
(2) a host cell; and
(3) transferrin.

The expression vector can be used to construct an expression vector for a fusion protein comprising an antibody or fragment thereof that specifically binds a transferrin, a target protein, and optionally a linker, wherein the antibody or fragment thereof is fused to the carboxyl-terminus or amino-terminus of the target protein, and the linker optionally separates the antibody and the carboxyl-terminus or amino-terminus of the target protein.

The host cell can be used to construct a recombinant cell for expressing the fusion protein, e.g., by transforming the host cell with the expression vector for the fusion protein, using any method known in the art in view of the present invention.

The transferrin can be used to stabilize the fusion protein. It may also be used to isolate the fusion protein by affinity chromatography.

According to an embodiment of the present invention, the system can further comprise a solid support for capturing the fusion protein via specific binding between the antibody or fragment thereof in the fusion protein and the transferrin associated with the solid support, or via specific binding between a fusion tag on the fusion protein and a binding partner of the fusion tag associated with the solid support.

The system can further comprise one or more buffers useful for the expression and/or isolation of the fusion protein.

The following specific examples of the invention are further illustrative of the nature of the invention, and it needs to be understood that the invention is not limited thereto.

EXAMPLE

Materials and Methods
Isolation of Transferrin sdAbs from a Llama Immune Phage Display Library A male llama (*Lama glama*) was injected subcutaneously with 50 µg human transferrin and 50 µg cynomolgus monkey transferrin on days 1, 22, 36, 50 and 64, respectively [11]. Complete Freund's Adjuvant (Sigma, St. Louis, Mo.) was used for the primary immunization and Incomplete Freund's Adjuvant was used for subsequent immunizations 2-4. Adjuvant was not used for the final immunization. The llama was bled one week following each immunization and heparinized blood was collected for immediate isolation of the peripheral blood leukocytes, which were then stored at −80° C. until further use.

Total RNA was isolated from $1 \times 10^8$ leukocytes using a QIAamp RNA Blood Mini Kit (Qiagen; Hilden, Germany). cDNA was synthesized using $pd(N)_6$ as primer and 566 ng total RNA as the template.

```
Four forward primers
P441_VHHF1
                                        (SEQ ID NO: 361)
(GCCCAGCCGGCCATGGCCSMBGTRCAGCTGGTGGAKTCTGGGGGA), P442_VHHF2
                                        (SEQ ID NO: 362)
(GCCCAGCCGGCCATGGCCCAGGTAAAGCTGGAGGAGTCTGGGGGA), P759_VHHF3
                                        (SEQ ID NO: 363)
(GCCCAGCCGGCCATGGCCCAGGTACAGCTGGTGGAGTCT)
and P444_VHHF4
                                        (SEQ ID NO: 364)
(GCCCAGCCGGCCATGGCCGAGGTGCAGCTGGTGGAGTGTGG)
and two reverse primers
P445_CH2R
                                        (SEQ ID NO: 365)
(CGCCATCAAGGTACCAGTTGA)
and P446_CH2b3R
                                        (SEQ ID NO: 366)
(GGGGTACCTGTCATCCACGGACCAGCTGA)
``` were used to amplify $V_H$-$C_H1$-Hinge-$C_H2$ region of conventional immunoglobulin G antibody (IgG) or $V_H$H-Hinge-$C_H2$ of heavy chain antibody. Amplified $V_H$H products of approximately 600 bp from the primer combination with P445_CH2R were extracted from a 1% agarose gel and purified with a QIAquick Gel Extraction Kit (Qiagen) and the amplified products from primers P446_CH2R were PCR purified. In a second PCR reaction, two primers, P440_VHHF (CATGTGTAGACTCGCGGCCCAGCCGGCCATGGCC) (SEQ ID NO: 367) and P447_VHHR (CATGTGTAGATTCCTGGCCGGCCTGGCCTGAGGAGACGGTGACCTG) (SEQ ID NO: 368) were used to introduce SfiI restriction sites and to amplify the final sdAb fragments from the combined amplified products. The final PCR product was digested with SfiI and ligated into a conventional phagemid vector constructed at GenScript Inc., and transformed into *E. coli* TG1 by electroporation. Phage were rescued and amplified with helper phage M13KO7 (NEB; Ipswich, Mass.).

The llama immune phage display library was panned against human and cynomolgus monkey transferrin that was conjugated to M-280 beads (Invitrogen; Carlsbad, Calif.). Approximately $3 \times 10^{11}$ phages were added to the beads and incubated at 37° C. for 2 hours (hr) for antigen binding. After disposal of unbound phages, the beads were washed six times with phosphate buffered saline supplemented with 0.05% Tween 20 (PBST) for round one and the washes were increased by one for each additional round. Phages were eluted by a 10 minute incubation with 100 µl 100 mM triethylamine and the eluate was subsequently neutralized with 200 µl 1 M Tris-HCl (pH 7.5). Then the eluate was selected by protein A binding using protein A beads and eluted as described above. Then, the phage were amplified as described above but on a smaller scale. After two rounds of panning, eluted phage were used to infect exponentially growing *E. coli* TG1. Individual colonies were used in phage enzyme-linked immunosorbent assay (ELISA).

For phage ELISA, a 96-well microtiter plate was coated overnight with 2 µg/ml human transferrin or cynomolgus monkey and then blocked with 4% modified phosphate buffered saline (MPBS) for 2 hr at 37° C. Phage from individual clones were pre-blocked with 4% MPBS overnight, added to the pre-blocked wells and incubated for 1 hr. Phage ELISA was performed using the GE Healthcare Detection Module Recombinant Phage Antibody System (GE Healthcare, Uppsala, Sweden) and positive phage clones were sequenced.

Expression of Anti-Transferrin sdAbs

All the human transferrin and cynomolgus monkey binders were listed in Table 1. 6 sdAbs (AS02360, AS01313, AS01299, AS01290, AS01284 and AS01274) were selected for sdAb expression and purification. The expressed sdAbs have 6× Histidine purification tag at the carboxyl (C)-terminus. These sdAbs were expressed periplasmically and purified by immobilized metal ion affinity chromatography (IMAC) [13]. Briefly, clones were inoculated in 25 ml LB-Ampicillin (Amp) and incubated at 37° C. with 200 rotations per minute (rpm) shaking overnight. The next day, 20 ml of the culture were used to inoculate 1 L of M9 medium (0.2% glucose, 0.6% $Na_2HPO_4$, 0.3% $KH_2PO_4$, 0.1% $NH_4Cl$, 0.05% NaCl, 1 mM $MgCl_2$, 0.1 mM $CaCl_2$) supplemented with 0.4% casamino acids, 5 mg/L of vitamin B1 and 200 µg/ml of Amp, and cultured for 24 hr. 100 ml of 10× TB nutrients (12% Tryptone, 24% yeast extract and 4% glycerol), 2 ml of 100 mg/ml Amp and 1 ml of 1 M isopropyl-beta-D-Thiogalactopyranoside (IPTG) were added to the culture and incubation was continued for another 65-70 hr at 28° C. with 200 rpm shaking. *E. coli* cells were harvested by centrifugation and lysed with lysozyme. Cell lysates were centrifuged, and clear supernatant was loaded onto High-Trap™ chelating affinity columns (GE Healthcare) and His-tagged proteins were purified.

Thermostability Evaluation by ELISA

SdAbs were diluted to 1.0 µg/ml, 0.2 µg/ml, and 0.04 µg/ml in PBS (pH 7.4). The samples were heated for 30 minutes at 50° C., 55° C., 60° C., 65° C., 70° C. and 75° C. in water bath. All samples were allowed to cool to room temperature on the bench top. Samples were centrifuged to pellet aggregated material. Remaining soluble protein was assayed for binding activity using ELISA. For ELISA, a 96-well microtiter plate was coated overnight with 2 µg/ml human transferrin or cynomolgus monkey and then blocked with 4% modified phosphate buffered saline (MPBS) for 2 hr at 37° C. The heat treated sdAb samples were added to the pre-blocked wells and incubated for 1 hr. A horseradish peroxidase conjugated anti-sdAb antibody served as the secondary reagent. The plate was developed and the absorbance was read at 450 nm.

Surface Plasmon Resonance (SPR) Analysis

Experiments were performed using a BIAcore T200 optical sensor platform and research grade CM5 sensor chips (GE Healthcare). AS01274 sdAb and AS01299 sdAb were immobilized on the sensor chip surface by standard amine coupling. All experiments were carried out in HEPES buffer [10 mM HEPES (pH 7.4), 150 mM NaCl, 3.4 mM EDTA, 0.005% Tween 20] at 25° C. Human Transferrin and Cynomolgus monkey Transferrin were injected at serial dilutions ranging from 3.9 nM to 2000 nM at a flow rate of 30 µl/min unless otherwise indicated. The amount of bound analyte after subtraction from the blank control surface is shown as relative response units (RU). The double referenced sensorgrams from each injection series were analyzed for binding kinetics using BIA evaluation software (GE Healthcare). Dissociation constants ($K_D$s) were calculated from the on- and off-rates ($k_{on}$ and $k_{off}$, respectively), as determined by global fitting of the experimental data to a 1:1 Langmuir binding model ($Chi^2 < 1$).

Measurement of Serum Half-Life

AS01274 sdAb and AS01299 sdAb were selected for serum half-life measurement. The two sdAbs as mentioned above were fused to another sdAb (anti-IL6R sdAb) with very short half-life (minutes to hours) to make AS01274 sdAb fusion protein and AS01299 sdAb fusion protein. The positive control for this experiment is anti-HSA sdAb fusion protein. 3 cynomolgus monkeys with weight of 4-5 kg were intravenously (i.v.) injected with 30 mg AS01274 sdAb fusion protein, AS01299 sdAb fusion protein and anti-HSA fusion protein, respectively. Blood was collected from the eye through a glass capillary at indicated time points. Sera were separated and stored at −80° C. until further use. Concentrations of the injected antibody molecules in the above collected samples were measured by ELISA.

To determine the serum half-life of AS01274 sdAb fusion protein and AS01299 sdAb fusion protein, anti-sdAb polyclonal antibody was coated on microtiter plates (Costar, 9018) overnight at 4° C. at a concentration of 2 µg/ml. The positive control anti-HSA fusion protein was done the same way as the two anti-transferrin sdAb fusion proteins. After washing three times with PBST, plates were blocked with 1% BSA in PBST for two hours at 37° C. Diluted sera (1% BSA in 0.05% PBS-T used as diluent) were added to the wells and incubated at 37° C. for 2 hours. After washing four times with PBST, HRP labeled anti-sdAb polyclonal antibody (0.1 µg/ml) (Abcam, ab9538) was added to the wells and incubated for another 1 hour. After washing the plate with PBST, the color was developed with TMB substrate for 10 minutes, and the reaction was stopped by adding 1 M HCl. The absorbance of each well was measured at 450 nm using a spectrometer. Serial dilutions of purified AS01274 sdAb fusion protein and AS01299 sdAb fusion protein in 1% BSA in PBST were used to generate a standard curve for serum concentration analysis.

Anti-Transferrin sdAb Humanization

Protein sequences of sdAb AS01274 and AS01299 were aligned with the 5 closest human germline sequences sharing the highest degree of homology, respectively. The best human germline sequence was selected as a human acceptor. A homology model was made. According to the model analysis data, residues potentially critical for antigen binding or antibody scaffold formation were left untouched while the rest were selected for conversion into the human counterpart. Initially a panel of four sequence optimized variants was generated (stage 1). These variants were analyzed for a number of parameters and the results obtained were used to design a second set of sdAbs (stage 2). The top 2 humanized sdAbs for AS01274 (AS01274VHa and AS01274VHa-A49) were selected based on binding, stability and functional activity data, and their sequences are shown in Table 1. Top 6 humanized sdAbs for AS01299 (AS01299VH3a, AS01299VH3a-A49, AS01299VH3a-L47, AS01299VH3a-M78, AS01299VH4, and AS01299VH4-L47) were selected based on binding, stability and functional activity data, and their sequences are shown in Table 1.

Humanized Anti-Transferrin sdAb Characterization

Expression of Humanized Anti-Transferrin sdAbs

Eight sdAbs (AS01274VHa, AS01274VHa-A49, AS01299VH3a, AS01299VH3a-A49, AS01299VH3a-L47, AS01299VH4, AS01299VH4-L47 and AS01299VH3a-M78) were selected for sdAb expression and purification. The expressed sdAbs have 6× Histidine purification tag at the carboxyl (C)-terminus. These sdAbs were expressed periplasmically and purified by immobilized metal ion affinity chromatography (IMAC) [13]. The expression and purification procedure is the same as mentioned in camelid sdAb production.

Surface Plasmon Resonance (SPR) Analysis

Experiments were performed using a BIAcore T200 optical sensor platform and research grade CM5 sensor chips (GE Healthcare; Little Chalfont, United Kingdom). Human transferrin was immobilized on the sensor chip surface by standard amine coupling. All experiments were carried out in HEPES buffer [10 mM HEPES (pH 7.4), 150 mM NaCl, 3.4 mM EDTA, 0.005% Tween 20] at 25° C. The humanized anti-transferrin sdAbs were injected at serial dilutions ranging from 0.375 nM to 24 nM at a flow rate of 30 µl/min unless otherwise indicated. The amount of bound analyte after subtraction from the blank control surface is shown as relative response units (RU). The double referenced sensorgrams from each injection series were analyzed for binding kinetics using BIA evaluation software (GE Healthcare). Dissociation constants ($K_Ds$) were calculated from the on- and off-rates ($k_{on}$ and $k_{off}$, respectively), as determined by global fitting of the experimental data to a 1:1 Langmuir binding model ($Chi^2<1$).

Anti-Transferrin sdAb and Protein a Binding Capacity Analysis

Determination of Static Binding Capacity

Two humanized anti-transferrin sdAbs (AS01274VHa-A49 and AS01299VH4) and one sdAb control for human serum albumin (HSA) were used for sdAb and Protein A binding capacity analysis. All three sdAbs were fused to one anti-IL-6R sdAb resulting three sdAb fusion proteins. The sdAb fusion proteins were prepared at a concentration of 2.1-2.4 mg/mL was prepared in PBS, pH 7.4 and filtered using a 0.22 µm low protein binding PVDF filter (Millipore, MA, USA). The protein A resin was equilibrated in PBS for 30 min and filtered to obtain a wet paste. A volume of 1 mL of sdAb fusion protein was added to 100 µL of wet resin. The slurry was incubated in mild shaking for 5 minutes, 10 minutes, 20 minutes, 30 minutes, 40 minutes, 50 minutes, 60 minutes and 100 minutes at room temperature. The resin was washed with 9 mL of PBS, pH 7.4. Protein elution was performed by adding 4 mL of 100 mM glycine-HCl, pH 2.5 to the resin and incubating the slurry in mild shaking for 15 min at room temperature. All fractions, i.e. flow-through, washing, and elution, were collected and analyzed by spectrophotometry at k=280 nm to determine the sdAb fusion protein content.

Determination of Dynamic Binding Capacity

100 µL Protein A resin was packed into a microbore 30 mm×2.1 mm I.D. column. An acetone pulse (0.01 M) was applied to the column to determine the total column void volume. After equilibration with PBS pH 7.4, 1 mL of 3.5 mg/mL sdAb fusion protein in PBS, pH 7.4 was loaded to the column at a linear flow velocity of 0.5 ml/minute. Breakthrough volume was determined at the point where the sdAb fusion protein concentration in the flow-through reached 10% of its feed concentration. This breakthrough volume was corrected by subtracting the void volume, and based on this corrected volume, the dynamic binding capacity of the protein A resin was determined.

Measurement of Serum Half-Life

AS01274VHa-A47 sdAb and AS01299VH4 sdAb were selected for serum half-life measurement. The two sdAbs as mentioned above were fused to another sdAb (anti-IL6R sdAb) with very short half-life (minutes to hours) to make AS01274VHa-A47 sdAb fusion protein and AS01299VH4 sdAb fusion protein. 2 cynomolgus monkeys with weight of 4-5 kg were intravenously (i.v.) injected with 30 mg AS01274VHa-A47 sdAb fusion protein and AS01299VH4 sdAb fusion protein, respectively. Blood was collected from the eye through a glass capillary at indicated time points. Sera were separated and stored at −80° C. until further use. Concentrations of the injected antibody molecules in the above collected samples were measured by ELISA.

To determine the serum half-life of AS01274VHa-A47 sdAb fusion protein and AS01299VH4 sdAb fusion protein, anti-sdAb polyclonal antibody was coated on microtiter plates (Costar, 9018) overnight at 4° C. at a concentration of 2 µg/ml. After washing three times with PBST, plates were blocked with 1% BSA in PBST for two hours at 37° C. Diluted sera (1% BSA in 0.05% PBS-T used as diluent) were added to the wells and incubated at 37° C. for 2 hours. After washing four times with PBST, HRP labeled anti-sdAb polyclonal antibody (0.1 µg/ml) (Abcam, ab9538) was added to the wells and incubated for another 1 hour. After washing the plate with PBST, the color was developed with TMB substrate for 10 minutes, and the reaction was stopped by adding 1 M HCl. The absorbance of each well was measured at 450 nm using a spectrometer. Serial dilutions of purified AS01274 sdAb fusion protein and AS01299 sdAb fusion protein in 1% BSA in PBST were used to generate a standard curve for serum concentration analysis.

Results

Isolation and Characterization of sdAbs

Isolation of transferrin-specific sdAbs was achieved by llama immunization with human transferrin and cynomolgus monkey transferrin, construction of an immune phage display library from the llama and subsequent panning.

Human transferrin and cynomolgus monkey transferrin induced a medium immune response in the llama. An approximately 25,000 fold dilution of the serum after the fifth immunization was still detected as positive (FIG. 1). This level of response is in agreement with what is usually achieved with llama immunization.

Figure 2:
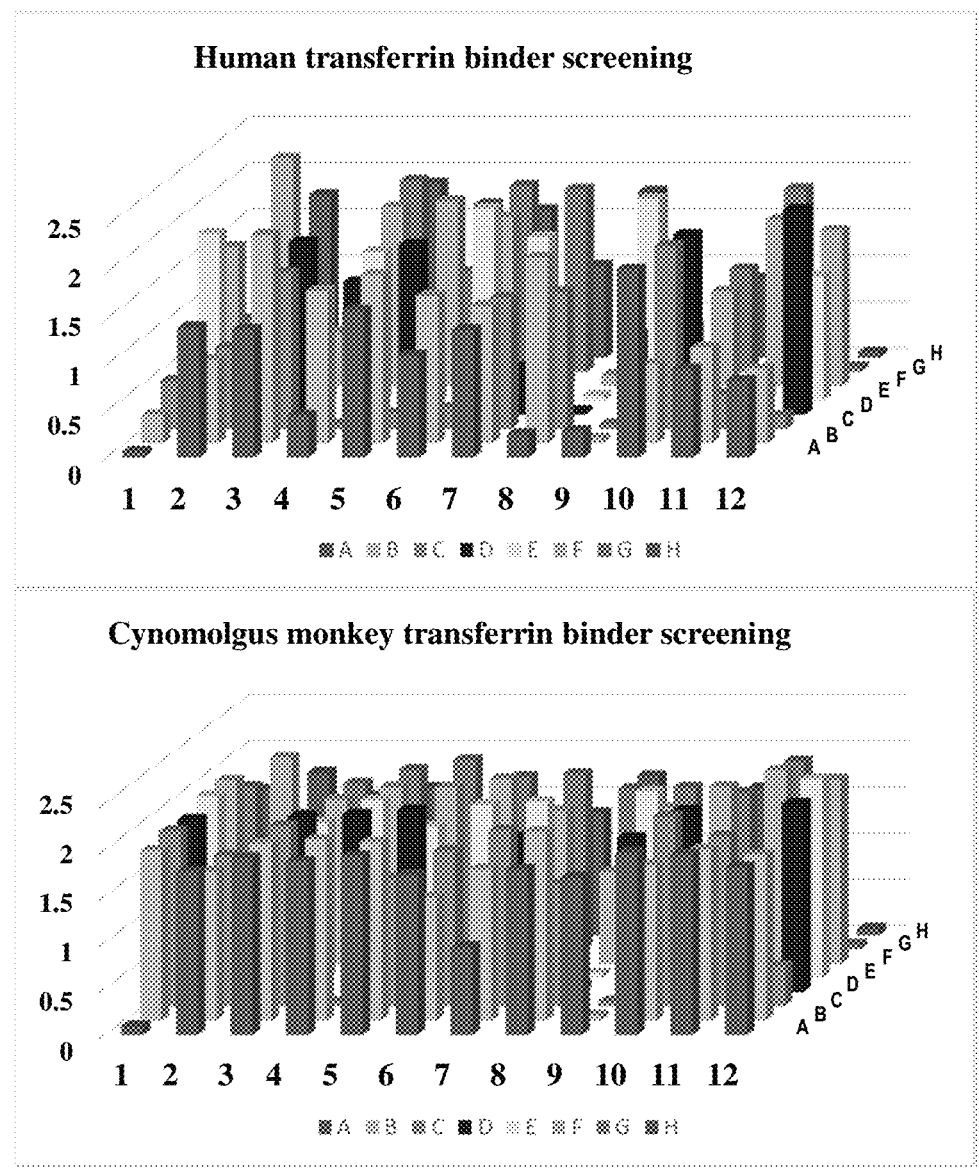
FIG. 2 shows binder screening of human transferrin (upper panel) and cynomolgus monkey transferrin (lower panel) by ELISA. Each column stands for one picked clone from output phage.

Approximately 2×10$^8$ llama leukocytes were used for the isolation of mRNA, which was then used for the construction of a phage library. The size of the obtained library was 2×10$^9$ independent transformants with a positive insertion rate of 92%. Two rounds of phage display panning were performed on immobilized transferrin, and phage enrichment was observed during panning (data not shown). Phage ELISA showed that ~88% of the analyzed clones bound to transferrin (FIG. 2). Analysis of encoding sequences of the sdAbs displayed on the phage clones revealed 37 different sdAb amino acid sequences (SEQ ID NOs: 316-352 corresponding to AS01274 to AS02365 of Table 1). The isolated 37 different sdAbs include framework regions 1-4 (Table 2) and complementarity determining regions 1-3 (Table 3).

TABLE 1

Anti-transferrin sequence summary

| | |
|---|---|
| AS01274 | QVQLVESGGGLVQPGGSLRLSCVASGSIASIATMAWYRQAPGQQRELVAGITRGGST KYADSVKGRFTISRDNAKNTLYLQMNSLKPDDTAVYYCTDYSRKYYQDYWGQGTQ VTVSS (SEQ ID NO: 316) |
| AS01276 | EVQLVECGGGLVQPGGSLRLSCVASGSIASIATMAWYRQAPGQQRELVAGITRGGST KYADSVKGRFTISRDNAKNTLYLQMNSLKPEDTAVYYCTDYSRGYYQDYWGQGTQ VTVSS (SEQ ID NO: 317) |
| AS01278 | QVQLVESGGGLVQPGGSLRLSCAASGSIFSINITMAWYRQAPGKQRELVAGITRSGTT TYAGSVKGRFTISRDNAKNITVYLQMNSLKPEDTAVYYCTDYSSSYYQDYWGQGTQ VTVSS (SEQ ID NO: 318) |
| AS01281 | EVQLVECGGGLVQPGGSLRLSCAASGSIFSINTMGWYRQAPGKQRELVAGITRGGST KYADSVKGRFTISRDNAKNTLYLQMNSLKPEDTAVYYCTDYSRSYYQDYWGQGTQ VTVSS (SEQ ID NO: 319) |
| AS01282 | QVKLEESGGGLVQPGGSLRLSCAASGSIFSINTMGWYRQRPGKQRELVAAITRGGNT NYADSVKGRFSISRDNAKNTMYLQMNSLKPEDTAVYYCTDYSRRYYQDDWGQGTQ VTVSS (SEQ ID NO: 320) |
| AS01284 | QVQLVESGGGLVQAGGSLRLSCAASGSIRPLRFMAWYRQAPGNQRGLVAAETSGGT IRYADSVKGRFTISRDNAKNTMYLQMNSLKPEDTAVYYCAARDLDDYWGQGIQVT VSS (SEQ ID NO: 321) |
| AS01285 | QVQLVESGGGLVQPGGSLRLSCAASGSIGSSATMAWYRQAPGKQRELVAGITRGGT TKYADSVKGRFTISRDNAENTVYLQMNSLKPEDTAVYYCTDYSRSYYEDHWGQGT QVTVSS (SEQ ID NO: 322) |
| AS01288 | QVQLVESGGGLVQPGGSLRLSCVASGSIFSIN1TMGWYRQAPGKQRELVAAITRGGNT KYTDSVKGRFTISRDNAKNITVYLQMNSLKPEDTAVYYCTDYSRSYYQDYWGQGTQ VTVSS (SEQ ID NO: 323) |
| AS01289 | QVKLEESGGGLVQPGGSLRLSCAASGSIFSIATMAWYRQAPGKQRELVAGITRSGST NYRDSVKGRFTISRDNAKNTMYLQMNSLKPEDTAVYYCTDYSSRYYHDYWGQGTQ VTVSS (SEQ ID NO: 324) |
| AS01290 | QVQLVESGGGLVQAGGSLRLSCAASRSISTLRFMAWYRQAPGEQRELVAAETSAGR LTYADSVKGRFTVSRDNAKDTIDLQMNSLKPEDTGVYYCAARGLADYWGQGTQVT VSS (SEQ ID NO: 325) |
| AS01291 | QVKLEESGGGLVQPGGSLRLSCAASGSIVSIATMAWYRQAPGKQRELVAGITRGGST KYADSVKGRFTISRDNAKNTVYLQMHSLKPEDTAVYYCTDYSRTYYEDHWGQGTQ VTVSS (SEQ ID NO: 326) |
| AS01292 | HVQLVESGGGLVQPGGSLRLSCVASGSIASVATMAWYRQAPGQQRELVAGITRGGS TKYADSVKGRFTISRDNAKNTLYLQMNSLKPEDTAVYYCTDYSRGYYQDYWGQGI QVTVSS (SEQ ID NO: 327) |
| AS01293 | QVQLVESGGGSVQPGGSLRLSCAASGSIASINTMAWYRQSPGKQRELVAGITRGGST NYADSVKGRFTISRDNAKNTVYLQMNSLKPEDTAVYYCTDYSLGYYQDYWGQGTQ VTVSS (SEQ ID NO: 328) |
| AS01296 | QVQLVESGGGLVQPGGSLRLSCAASGSIFSINTMAWYRQAPGKQRELVAGITRSGTT NYAGSVKGRFTISRDNAKNTVYLQMNGLKPEDTAVYYCTDYSRRYYQDDWGQGT QVTVSS (SEQ ID NO: 329) |
| AS01297 | EVQLVECGGGLVQPGGSLRLSCAASGSIFSIATMAWYRQAPGKQRELVAGITRSGST NYRDSVKGRFTISRDNAKNTMYLQMNSLKPEDTAVYYCTDYSSRYYHDYWGQGTQ VTVSS (SEQ ID NO: 330) |
| AS01298 | QVQLVESGGGLVQSGGSLRLSCAASGTIFAINTMAWYRQAPGQQRELVAGITRGGST KYADSVKGRFTISRDNAKNTLYLQMNSLKPEDTAVYYCTDYSRGYYQDYWGQGTQ VTVSS (SEQ ID NO: 331) |
| AS01299 | QVQLVESGGGLVQPGGSLRLSCAASGSIFSIATMAWYRQAPGKQRELVAGITRSGST NYRDSVKGRFTISRDNAKNTMYLQMNSLKPEDTAVYYCTDYSSRYYHDYWGQGTQ VTVSS (SEQ ID NO: 332) |
| AS01300 | QVQLVESGGGLVQPGGSLRLSCAASGSIASINTMAWYRQAPGKQRELVAGITSGGST KYADSVKGRFTISRDNAKNTVYLQMNNLKPEDTAIYYCTDYSKRYYQDYWGQGTQ VTVSS (SEQ ID NO: 333) |
| AS01302 | QVKLEESGGGLVQPGGSLTLSCAASGSIFSINTMAWYRQAPGKQRELVAGITRSGTT NYAGSVKGRFTISRDNAKNTVYLQMNSLKPEDTAVYYCTDYSRKYYEDQWGQGTQ VTVSS (SEQ ID NO: 334) |

TABLE 1-continued

Anti-transferrin sequence summary

| | |
|---|---|
| AS01303 | QVQLVESGGGLVQPGGSLRLSCAASGSIASINTMAWYRQAPGQQRELVAGITRGGST KYADSVKGRFTISRDNAKNTLYLQMNSLKPEDTAVYYCTDYSRGYYQDYWGQGTQ VTVSS (SEQ ID NO: 335) |
| AS01304 | QVQLVESGGGLVQPGGSLRLSCAASGSIFSINTMGWYRQAPGKQRELVAGITRGGST KYADSVKGRFTISRDNAKNTLYLQMNSLKPEDTAVYYCTDYSRSYYQDYWGQGTQ VTVSS (SEQ ID NO: 336) |
| AS01306 | QVQLVESGGGLVQPGGSLRLSCAASGSIFSINTMGWYRQAPGKQRELVAGITRGGTT NYANSVKGRFTISRDNAKNTVYLQMNSLKPEDTAVYYCTDYSSRYYHDYWGQGTQ VTVSS (SEQ ID NO: 337) |
| AS01308 | QVQLVESGGGLVQPGGSLRLSCAASGSIASINTMAWYRQAPGKQRELVAGITRSGTT TYAGSVKGRFTISRDNAKNTVYLQMNSLKPEDTAVYYCTDYSSSYYQDYWGQGTQ VTVSS (SEQ ID NO: 338) |
| AS01309 | QVQLVESGGGLVQPGGSLRLSCAASGSIFSINTMGWYRQRPGKQRELVAAITRGGNT NYADSVKGRFSISRDNAKNTMYLQMNSLKPEDTAVYYCTDYSRRYYQDDWGQGTQ VTVSS (SEQ ID NO: 339) |
| AS01310 | QVQLVESGGGLVQAGGSLRLSCVASGSIASIATMAWYRQAPGQQRELVAGITRGGST HYADSVKGRFTISRDNAKNTLYLQMNSLEPEDTAVYYCTDYSRRYYEDYWGQGTQ VTVSS (SEQ ID NO: 340) |
| AS01311 | EVQLVECGGGLVQPGGSLRLSCAASGSIASINTMAWYRQAPGQQRELVAGITRGGST NYADSVKGRFTISRDNAKNTLYLQMNSLKPEDTAVYYCTDYSRGYYQDYWGQGTQ VTVSS (SEQ ID NO: 341) |
| AS01312 | EVQLVECGGGLVQPGGSLRLSCAASGSIAGINTMAWYRQAPGQQRELVAGITRSGST KYADSVKGRFTISRDNAKNTLYLQMNSLKPEDTAVYYCTDYSRGYYQDYWGQGTQ VTVSS (SEQ ID NO: 342) |
| AS01313 | QVKLEESGGGLVQAGGSLRLSCAASGRTFSSHTMGWFRQPPGKEREFVAVIHWSGA STYYTDSVKGRFTISRDNAKNTVYLQMNSLKPEDTAIYYCAAEVPVSTWPPTEYSW WGQGTQVTVSS (SEQ ID NO: 343) |
| AS01316 | EVQLVECGGGLVQPGGSLRLSCAASGSIASINTMAWYRQAPGQQRELVAGITRGGST KYADSVKGRFTISRDNAKNTLYLQMNSLKPEDTAVYYCTDFSRDYYQDYWGQGTQ VTVSS (SEQ ID NO: 344) |
| AS01318 | QVQLVESGGGLVQPGGSLRLSCAASGSIFSINTMAWYRQAPGKQRELVAGITRSGTT TYAGSVKGRFTISRDNAKNTVYLQMNGLKPEDTAVYYCTDYSSSYYQDYWGQGTQ VTVSS (SEQ ID NO: 345) |
| AS01320 | EVQLVECGGGLVQPGGSLRLSCAASGSIASINTMAWYRQAPGQQRELVAGITRGGST KYADSVKGRFTISRDNAKNTLYLQMNSLKPEDTAVYYCTDYSRGYYQDYWGQGTQ VTVSS (SEQ ID NO: 346) |
| AS02358 | QVQLVESGGGLVQPGGSLRLSCAASGSIASINTMAWYRQSPGKQRELVAGITRGGST NYADSVKGRFTISRDNAKNTVYLQMNSLKPEDTAVYYCTDYSLGYYQDYWGQGTQ VTVSS (SEQ ID NO: 347) |
| AS02359 | QVQLVESGGGLVQPGGSLRLSCAASGSIASINTMAWYRQSPGKQRELVAGITRGGST NYADSVKGRFTISRDNAKNTVYLQMNSLKPEDTAVYYCTDYSLGYYQDYWGQGTQ VTVSS (SEQ ID NO: 348) |
| AS02360 | QVQLVESGGGLVQPGGSLRLSCAASGSIASINTMAWYRQSPGKQRELVAGITRGGST NYADSVKGRFTISRDNAKNTVYLQMNSLKPEDTAVYYCTDYSLGYYQDYWGQGTQ VTVSS (SEQ ID NO: 349) |
| AS02362 | QVQLVESGGGLVQPGGSLRLSCAASGSIASINTMAWYRQSPGKQRELVAGITRGGST NYADSVKGRFAISRDNAKNTVYLQMNSLKPEDTAVYYCTDYSLGYYQDYWGQGTQ VTVSS (SEQ ID NO: 350) |
| AS02363 | QVQLVESGGGLVQPGGSLRLSCAASGSIASINTMAWYRQSPGKQRELVAGITRGGST NYADSVKGRFTISRDNAKNTVYLQMNSLKPEDTAVYYCTDYSLGYYQDYWGQGTQ VTVSS (SEQ ID NO: 351) |
| AS02365 | QVKLEESGGGLVQPGGSLRLSCAASGSIASINTMAWYRQSPGKQRELVAGITRGGST NYADSVKGRFTISRDNAKNTVYLQMNSLKPEDTAVYYCTDYSLGYYQDYWGQGTQ VTVSS (SEQ ID NO: 352) |
| AS01274VHa | EVQLVESGGGLVQPGGSLRLSCAASGSIASIATMAWYRQAPGKGTFLVAGITRGGST KYADSVKGRFTISRDNSKNTLYLQMNSLRAEDTAVYYCTDYSRKYYQDYWGQGTL VTVSS (SEQ ID NO: 353) |

TABLE 1-continued

Anti-transferrin sequence summary

AS01299VH3a   EVQLVESGGGLVQPGGSLRLSCAASGSIFSIATMAWYRQAPGKGTFLVAGITRSGST
              NYRDSVKGRFTISRDNSKNTMYLQMNSLRAEDTAVYYCTDYSSRYYHDYWGQGTL
              VTVSS (SEQ ID NO: 354)

AS01274VHa-   EVQLVESGGGLVQPGGSLRLSCAASGSIASIATMAWYRQAPGKGTFLVSGITRGGST
A49           KYADSVKGRFTISRDNSKNTLYLQMNSLRAEDTAVYYCTDYSRKYYQDYWGQGTL
              VTVSS (SEQ ID NO: 355)

AS01299VH3a-  EVQLVESGGGLVQPGGSLRLSCAASGSIFSIATMAWYRQAPGKGTFLVSGITRSGSTN
A49           YRDSVKGRFTISRDNSKNTMYLQMNSLRAEDTAVYYCTDYSSRYYHDYWGQGTLV
              TVSS (SEQ ID NO: 356)

AS01299VH3a-  EVQLVESGGGLVQPGGSLRLSCAASGSIFSIATMAWYRQAPGKGTFWVAGITRSGST
L47           NYRDSVKGRFTISRDNSKNTMYLQMNSLRAEDTAVYYCTDYSSRYYHDYWGQGTL
              VTVSS (SEQ ID NO: 357)

AS01299VH3a-  EVQLVESGGGLVQPGGSLRLSCAASGSIFSIATMAWYRQAPGKGTFLVAGITRSGST
M78           NYRDSVKGRFTISRDNSKNTLYLQMNSLRAEDTAVYYCTDYSSRYYHDYWGQGTL
              VTVSS (SEQ ID NO: 358)

AS01299VH4    EVQLVESGGGLVQPGGSLRLSCAASGSIFSIATMAWYRQAPGKGTFLVSGITRSGSTN
              YRDSVKGRFTISRDNSKNTLYLQMNSLRAEDTAVYYCTDYSSRYYHDYWGQGTLV
              TVSS (SEQ ID NO: 359)

AS01299VH4-   EVQLVESGGGLVQPGGSLRLSCAASGSIFSIATMAWYRQAPGKGTFWVSGITRSGST
L47           NYRDSVKGRFTISRDNSKNTLYLQMNSLRAEDTAVYYCTDYSSRYYHDYWGQGTL
              VTVSS (SEQ ID NO: 360)

TABLE 2

Framework regions (FR) 1-4

| Ab ID | FR1 | NO | FR2 | NO | FR3 | NO | FR4 | NO |
|---|---|---|---|---|---|---|---|---|
| AS01274 | QVQLVESGG GLVQPGGSL RLSCVAS | 1 | WYRQAPG QQRELVA | 91 | RFTISRDNAKNTLYLQ MNSLKPDDTAVYYCTD | 181 | WGQGT QVTVSS | 271 |
| AS01276 | EVQLVECGG GLVQPGGSL RLSCVAS | 2 | WYRQAPG QQRELVA | 92 | RFTISRDNAKNTLYLQ MNSLKPEDTAVYYCTD | 182 | WGQGT QVTVSS | 272 |
| AS01278 | QVQLVESGG GLVQPGGSL RLSCAAS | 3 | WYRQAPG KQRELVA | 93 | RFTISRDNAKNTVYLQ MNSLKPEDTAVYYCTD | 183 | WGQGT QVTVSS | 273 |
| AS01281 | EVQLVECGG GLVQPGGSL RLSCAAS | 4 | WYRQAPG KQRELVA | 94 | RFTISRDNAKNTLYLQ MNSLKPEDTAVYYCTD | 184 | WGQGT QVTVSS | 274 |
| AS01282 | QVKLEESGG GLVQPGGSL RLSCAAS | 5 | WYRQRPG KQRELVA | 95 | RFSISRDNAKNTMYLQ MNSLKPEDTAVYYCTD | 185 | WGQGT QVTVSS | 275 |
| AS01284 | QVQLVESGG GLVQAGGSL RLSCAAS | 6 | WYRQAPG NQRGLVA | 96 | RFTISRDNAKNTMYLQ MNSLKPEDTAVYYCAA | 186 | WGQGI QVTVSS | 276 |
| AS01285 | QVQLVESGG GLVQPGGSL RLSCAAS | 7 | WYRQAPG KQRELVA | 97 | RFTISRDNAENTVYLQ MNSLKPEDTAVYYCTD | 187 | WGQGT QVTVSS | 277 |
| AS01288 | QVQLVESGG GLVQPGGSL RLSCVAS | 8 | WYRQAPG KQRELVA | 98 | RFTISRDNAKNTVYLQ MNSLKPEDTAVYYCTD | 188 | WGQGT QVTVSS | 278 |
| AS01289 | QVKLEESGG GLVQPGGSL RLSCAAS | 9 | WYRQAPG KQRELVA | 99 | RFTISRDNAKNTMYLQ MNSLKPEDTAVYYCTD | 189 | WGQGT QVTVSS | 279 |
| AS01290 | QVQLVESGG GLVQAGGSL RLSCAAS | 10 | WYRQAPG EQRELVA | 100 | RFTVSRDNAKDTIDLQ MNSLKPEDTGVYYCAA | 190 | WGQGT QVTVSS | 280 |

TABLE 2-continued

Framework regions (FR) 1-4

| Ab ID | FR1 | NO | FR2 | NO | FR3 | NO | FR4 | NO |
|---|---|---|---|---|---|---|---|---|
| AS01291 | QVKLEESGG GLVQPGGSL RLSCAAS | 11 | WYRQAPG KQRELVA | 101 | RFTISRDNAKNTVYLQ MHSLKPEDTAVYYCTD | 191 | WGQGT QVTVSS | 281 |
| AS01292 | HVQLVESGG GLVQPGGSL RLSCVAS | 12 | WYRQAPG QQRELVA | 102 | RFTISRDNAKNTLYLQ MNSLKPEDTAVYYCTD | 192 | WGQGI QVTVSS | 282 |
| AS01293 | QVQLVESGG GSVQPGGSL RLSCAAS | 13 | WYRQSPG KQRELVA | 103 | RFTISRDNAKNTVYLQ MNSLKPEDTAVYYCTD | 193 | WGQGT QVTVSS | 283 |
| AS01296 | QVQLVESGG GLVQPGGSL RLSCAAS | 14 | WYRQAPG KQRELVA | 104 | RFTISRDNAKNTVYLQ MNGLKPEDTAVYYCTD | 194 | WGQGT QVTVSS | 284 |
| AS01297 | EVQLVECGG GLVQPGGSL RLSCAAS | 15 | WYRQAPG KQRELVA | 105 | RFTISRDNAKNTMYLQ MNSLKPEDTAVYYCTD | 195 | WGQGT QVTVSS | 285 |
| AS01298 | QVQLVESGG GLVQSGGSL RLSCAAS | 16 | WYRQAPG QQRELVA | 106 | RFTISRDNAKNTLYLQ MNSLKPEDTAVYYCTD | 196 | WGQGT QVTVSS | 286 |
| AS01299 | QVQLVESGG GLVQPGGSL RLSCAAS | 17 | WYRQAPG KQRELVA | 107 | RFTISRDNAKNTMYLQ MNSLKPEDTAVYYCTD | 197 | WGQGT QVTVSS | 287 |
| AS01300 | QVQLVESGG GLVQPGGSL RLSCAAS | 18 | WYRQAPG KQRELVA | 108 | RFTISRDNAKNTVYLQ MNNLKPEDTAIYYCTD | 198 | WGQGT QVTVSS | 288 |
| AS01302 | QVKLEESGG GLVQPGGSL TLSCAAS | 19 | WYRQAPG KQRELVA | 109 | RFTISRDNAKNTVYLQ MNSLKPEDTAVYYCTD | 199 | WGQGT QVTVSS | 289 |
| AS01303 | QVQLVESGG GLVQPGGSL RLSCAAS | 20 | WYRQAPG QQRELVA | 110 | RFTISRDNAKNTLYLQ MNSLKPEDTAVYYCTD | 200 | WGQGT QVTVSS | 290 |
| AS01304 | QVQLVESGG GLVQPGGSL RLSCAAS | 21 | WYRQAPG KQRELVA | 111 | RFTISRDNAKNTLYLQ MNSLKPEDTAVYYCTD | 201 | WGQGT QVTVSS | 291 |
| AS01306 | QVQLVESGG GLVQPGGSL RLSCAAS | 22 | WYRQAPG KQRELVA | 112 | RFTISRDNAKNTVYLQ MNSLKPEDTAVYYCTD | 202 | WGQGT QVTVSS | 292 |
| AS01308 | QVQLVESGG GLVQPGGSL RLSCAAS | 23 | WYRQAPG KQRELVA | 113 | RFTISRDNAKNTVYLQ MNSLKPEDTAVYYCTD | 203 | WGQGT QVTVSS | 293 |
| AS01309 | QVQLVESGG GLVQPGGSL RLSCAAS | 24 | WYRQRPG KQRELVA | 114 | RFSISRDNAKNTMYLQ MNSLKPEDTAVYYCTD | 204 | WGQGT QVTVSS | 294 |
| AS01310 | QVQLVESGG GLVQAGGSL RLSCVAS | 25 | WYRQAPG QQRELVA | 115 | RFTISRDNAKNTLYLQ MNSLEPEDTAVYYCTD | 205 | WGQGT QVTVSS | 295 |
| AS01311 | EVQLVECGG GLVQPGGSL RLSCAAS | 26 | WYRQAPG QQRELVA | 116 | RFTISRDNAKNTLYLQ MNSLKPEDTAVYYCTD | 206 | WGQGT QVTVSS | 296 |
| AS01312 | EVQLVECGG GLVQPGGSL RLSCAAS | 27 | WYRQAPG QQRELVA | 117 | RFTISRDNAKNTLYLQ MNSLKPEDTAVYYCTD | 207 | WGQGT QVTVSS | 297 |
| AS01313 | QVKLEESGG GLVQAGGSL RLSCAAS | 28 | WFRQPPG KEREFVA | 118 | RFTISRDNAKNTVYLQ MNSLKPEDTAIYYCAA | 208 | WGQGT QVTVSS | 298 |
| AS01316 | EVQLVECGG GLVQPGGSL RLSCAAS | 29 | WYRQAPG QQRELVA | 119 | RFTISRDNAKNTLYLQ MNSLKPEDTAVYYCTD | 209 | WGQGT QVTVSS | 299 |

TABLE 2-continued

Framework regions (FR) 1-4

| Ab ID | FR1 | NO | FR2 | NO | FR3 | NO | FR4 | NO |
|---|---|---|---|---|---|---|---|---|
| AS01318 | QVQLVESGGGLVQPGGSLRLSCAAS | 30 | WYRQAPGKQRELVA | 120 | RFTISRDNAKNTVYLQMNGLKPEDTAVYYCTD | 210 | WGQGTQVTVSS | 300 |
| AS01320 | EVQLVECGGGLVQPGGSLRLSCAAS | 31 | WYRQAPGQQRELVA | 121 | RFTISRDNAKNTLYLQMNSLKPEDTAVYYCTD | 211 | WGQGTQVTVSS | 301 |
| AS02358 | QVQLVESGGGLVQPGGSLRLSCAAS | 32 | WYRQSPGKQRELVA | 122 | RFTISRDNAKNTVYLQMNSLKPEDTAVYYCTD | 212 | WGQGTQVTVSS | 302 |
| AS02359 | QVQLVESGGGLVQPGGSLRLSCAAS | 33 | WYRQSPGKQRELVA | 123 | RFTISRDNAKNTVYLQMNSLKPEDTAVYYCTD | 213 | WGQGTQVTVSS | 303 |
| AS02360 | QVQLVESGGGLVQPGGSLRLSCAAS | 34 | WYRQSPGKQRELVA | 124 | RFTISRDNAKNTVYLQMNSLKPEDTAVYYCTD | 214 | WGQGTQVTVSS | 304 |
| AS02362 | QVQLVESGGGLVQPGGSLRLSCAAS | 35 | WYRQSPGKQRELVA | 125 | RFAISRDNAKNTVYLQMNSLKPEDTAVYYCTD | 215 | WGQGTQVTVSS | 305 |
| AS02363 | QVQLVESGGGLVQPGGSLRLSCAAS | 36 | WYRQSPGKQRELVA | 126 | RFTISRDNAKNTVYLQMNSLKPEDTAVYYCTD | 216 | WGQGTQVTVSS | 306 |
| AS02365 | QVKLEESGGGLVQPGGSLRLSCAAS | 37 | WYRQSPGKQRELVA | 127 | RFTISRDNAKNTVYLQMNSLKPEDTAVYYCTD | 217 | WGQGTQVTVSS | 307 |

FR: Framework;
NO: SEQ ID NO

TABLE 3

Complementarity determining regions 1-3 (CDRs 1-3)

| Ab ID | CDR1 | NO | CDR2 | NO | CDR3 | NO |
|---|---|---|---|---|---|---|
| AS01274 | GSIASIATMA | 46 | GITRGGSTKYADSVKG | 136 | YSRKYYQDY | 226 |
| AS01276 | GSIASIATMA | 47 | GITRGGSTKYADSVKG | 137 | YSRGYYQDY | 227 |
| AS01278 | GSIFSINTMA | 48 | GITRSGTTTYAGSVKG | 138 | YSSSYYQDY | 228 |
| AS01281 | GSIFSINTMG | 49 | GITRGGSTKYADSVKG | 139 | YSRSYYQDY | 229 |
| AS01282 | GSIFSINTMG | 50 | AITRGGNTNYADSVKG | 140 | YSRRYYQDD | 230 |
| AS01284 | GSIRPLRFMA | 51 | AETSGGTIRYADSVKG | 141 | RDLDDY | 231 |
| AS01285 | GSIGSSATMA | 52 | GITRGGTTKYADSVKG | 142 | YSRSYYEDH | 232 |
| AS01288 | GSIFSINTMG | 53 | AITRGGNTKYTDSVKG | 143 | YSRSYYQDY | 233 |
| AS01289 | GSIFSIATMA | 54 | GITRSGSTNYRDSVKG | 144 | YSSRYYHDY | 234 |
| AS01290 | RSISTLRFMA | 55 | AETSAGRLTYADSVKG | 145 | RGLADY | 235 |
| AS01291 | GSIVSIATMA | 56 | GITRGGSTKYADSVKG | 146 | YSRTYYEDH | 236 |
| AS01292 | GSIASVATMA | 57 | GITRGGSTKYADSVKG | 147 | YSRGYYQDY | 237 |
| AS01293 | GSIASINTMA | 58 | GITRGGSTNYADSVKG | 148 | YSLGYYQDY | 238 |
| AS01296 | GSIFSINTMA | 59 | GITRSGTTNYAGSVKG | 149 | YSRRYYQDD | 239 |
| AS01297 | GSIFSIATMA | 60 | GITRSGSTNYRDSVKG | 150 | YSSRYYHDY | 240 |
| AS01298 | GTIFAINTMA | 61 | GITRGGSTKYADSVKG | 151 | YSRGYYQDY | 241 |
| AS01299 | GSIFSIATMA | 62 | GITRSGSTNYRDSVKG | 152 | YSSRYYHDY | 242 |

TABLE 3-continued

Complementarity determining regions 1-3 (CDRs 1-3)

| Ab ID | CDR1 | NO | CDR2 | NO | CDR3 | NO |
|---|---|---|---|---|---|---|
| AS01300 | GSIASINTMA | 63 | GITSGGSTKYADSVKG | 153 | YSKRYYQDY | 243 |
| AS01302 | GSIFSINTMA | 64 | GITRSGTTNYAGSVKG | 154 | YSRKYYEDQ | 244 |
| AS01303 | GSIASINTMA | 65 | GITRGGSTKYADSVKG | 155 | YSRGYYQDY | 245 |
| AS01304 | GSIFSINTMG | 66 | GITRGGSTKYADSVKG | 156 | YSRSYYQDY | 246 |
| AS01306 | GSIFSINTMG | 67 | GITRGGTTNYANSVKG | 157 | YSSRYYHDY | 247 |
| AS01308 | GSIASINTMA | 68 | GITRSGTTTYAGSVKG | 158 | YSSSYYQDY | 248 |
| AS01309 | GSIFSINTMG | 69 | AITRGGNTNYADSVKG | 159 | YSRRYYQDD | 249 |
| AS01310 | GSIASIATMA | 70 | GITRGGSTHYADSVKG | 160 | YSRRYYEDY | 250 |
| AS01311 | GSIASINTMA | 71 | GITRGGSTNYADSVKG | 161 | YSRGYYQDY | 251 |
| AS01312 | GSIAGINTMA | 72 | GITRSGSTKYADSVKG | 162 | YSRGYYQDY | 252 |
| AS01313 | GRTFSSHTMG | 73 | VIHWSGASTYYTDSVKG | 163 | EVPVSTWPPTEYSW | 253 |
| AS01316 | GSIASINTMA | 74 | GITRGGSTKYADSVKG | 164 | FSRDYYQDY | 254 |
| AS01318 | GSIFSINTMA | 75 | GITRSGTTTYAGSVKG | 165 | YSSSYYQDY | 255 |
| AS01320 | GSIASINTMA | 76 | GITRGGSTKYADSVKG | 166 | YSRGYYQDY | 256 |
| AS02358 | GSIASINTMA | 77 | GITRGGSTNYADSVKG | 167 | YSLGYYQDY | 257 |
| AS02359 | GSIASINTMA | 78 | GITRGGSTNYADSVKG | 168 | YSLGYYQDY | 258 |
| AS02360 | GSIASINTMA | 79 | GITRGGSTNYADSVKG | 169 | YSLGYYQDY | 259 |
| AS02362 | GSIASINTMA | 80 | GITRGGSTNYADSVKG | 170 | YSLGYYQDY | 260 |
| AS02363 | GSIASINTMA | 81 | GITRGGSTNYADSVKG | 171 | YSLGYYQDY | 261 |
| AS02365 | GSIASINTMA | 82 | GITRGGSTNYADSVKG | 172 | YSLGYYQDY | 262 |

CDR: Complementarity determining region;
NO: SEQ ID NO

Figure 3:
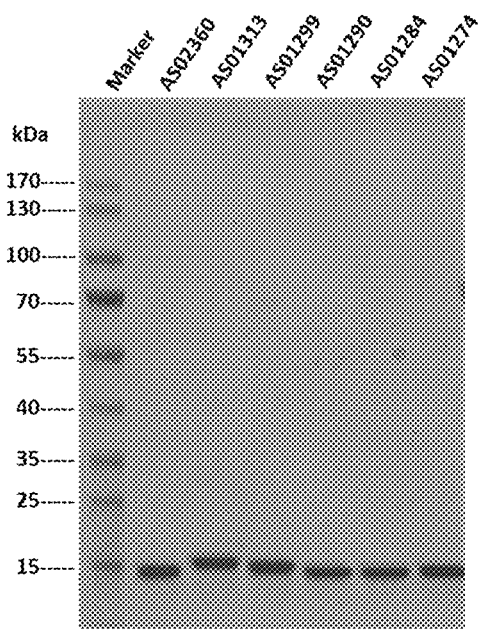
FIG. 3 is an image of an SDS polyacrylamide gel of purified sdAbs AS02630, AS01313, AS01299, AS01290, AS01284 and AS01274, isolated from *Escherichia coli*, the amino acid sequences of which are shown in Table 1.

Six sdAbs, AS02360, AS01313, AS01299, AS01290, AS01284 and AS01274 were sub-cloned into an *E. coli* periplasmic expression vector, pSJF2H[12]. The six sdAbs, each tagged with a 6× histidine (His) tag at their C-terminal, were produced in *E. coli* and purified by IMAC (FIG. 3). AS02360, AS01313, AS01299, AS01290, AS01284 and AS01274 were purified at 20.29, 15.71, 22.20, 6.87, 15.03 and 19.53 mg per liter of TG1 culture, respectively.

The two transferrin sdAbs AS01274 and AS01299 were analyzed for binding to human transferrin and cynomolgus monkey transferrin using a SPR-based biosensor.

Figure 4A:
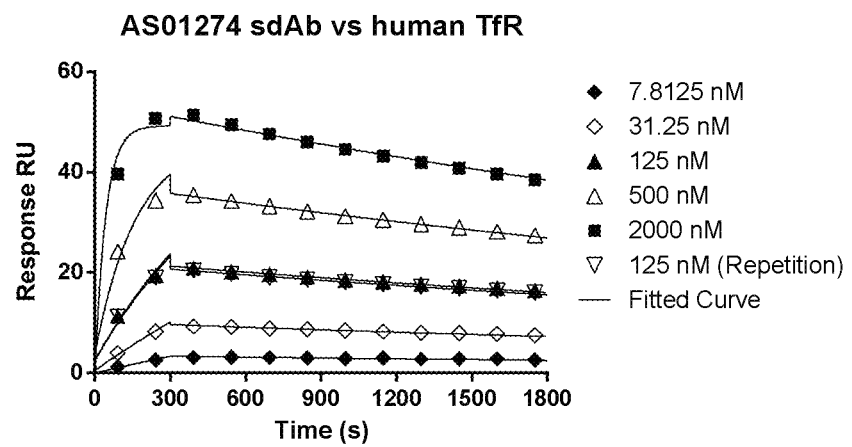
FIGS. 4A-4D show affinity determination of transferrin sdAbs binding to human transferrin, cynomolgus monkey transferrin by BIAcore T200.
Figure 4B:
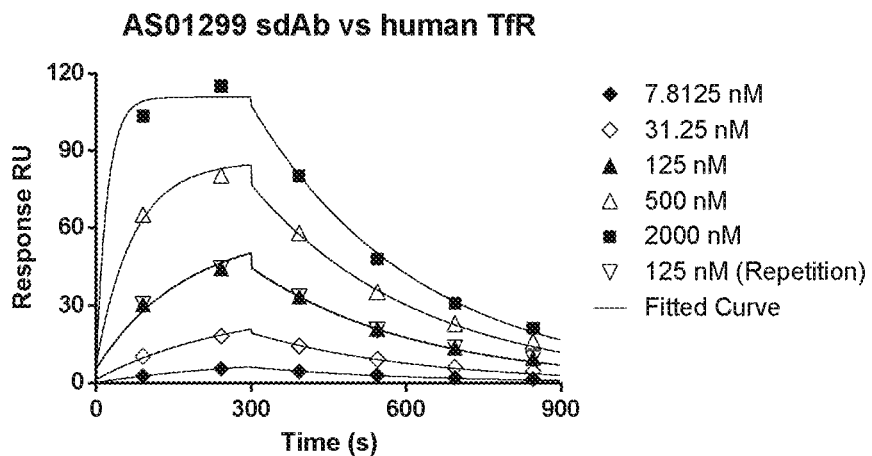
Figure 4C:
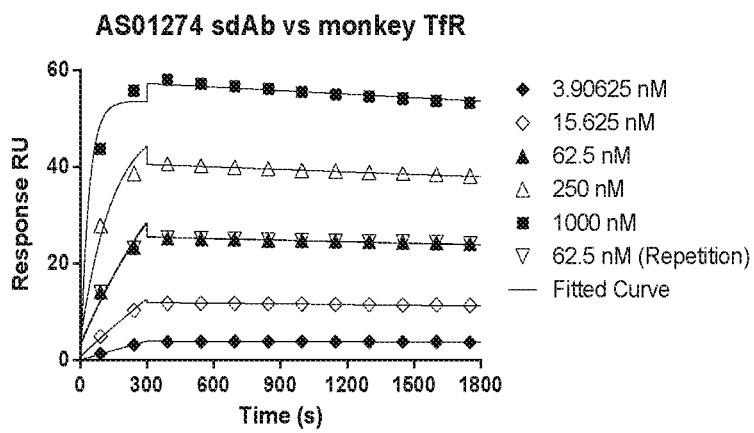
Figure 4D:
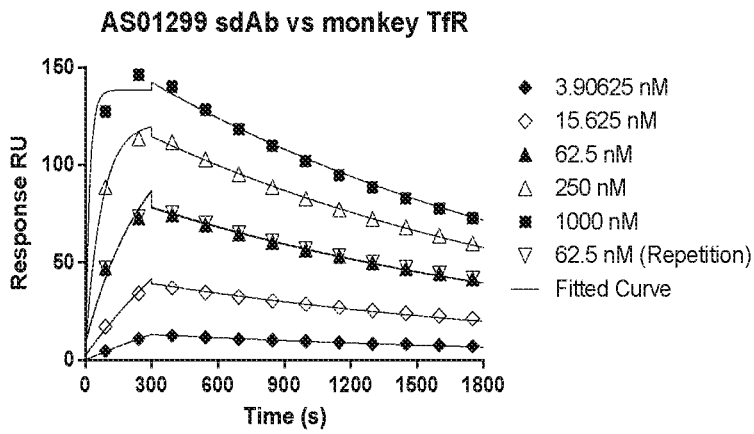

The results are shown in Table 4. The dissociation constants ($K_D$s) of AS01274 were calculated as 16 nM for human transferrin and 1.6 nM for cynomolgus monkey transferrin (FIG. 4A). The dissociation constants ($K_D$s) of the AS01299 were calculated as 140 nM for human transferrin and 8.8 nM for cynomolgus monkey transferrin (FIG. 4B).

TABLE 4 affinity measurement of obtained sdAbs

| Antigen | Analyte | $k_a$ (1/Ms) | $k_d$ (1/s) | $K_D$ (M) |
|---|---|---|---|---|
| AS01274 | Human | 1.2E+04 | 1.9E−04 | 1.6E−08 |
| AS01299 | transferrin | 2.2E+04 | 3.1E−03 | 1.4E−07 |

TABLE 4-continued affinity measurement of obtained sdAbs

| Antigen | Analyte | $k_a$ (1/Ms) | $k_d$ (1/s) | $K_D$ (M) |
|---|---|---|---|---|
| AS01274 | Cynomolgus monkey | 2.7E+04 | 4.4E−05 | 1.6E−09 |
| AS01299 | transferrin | 5.2E+04 | 4.6E−04 | 8.8E−09 |

Figure 5A:
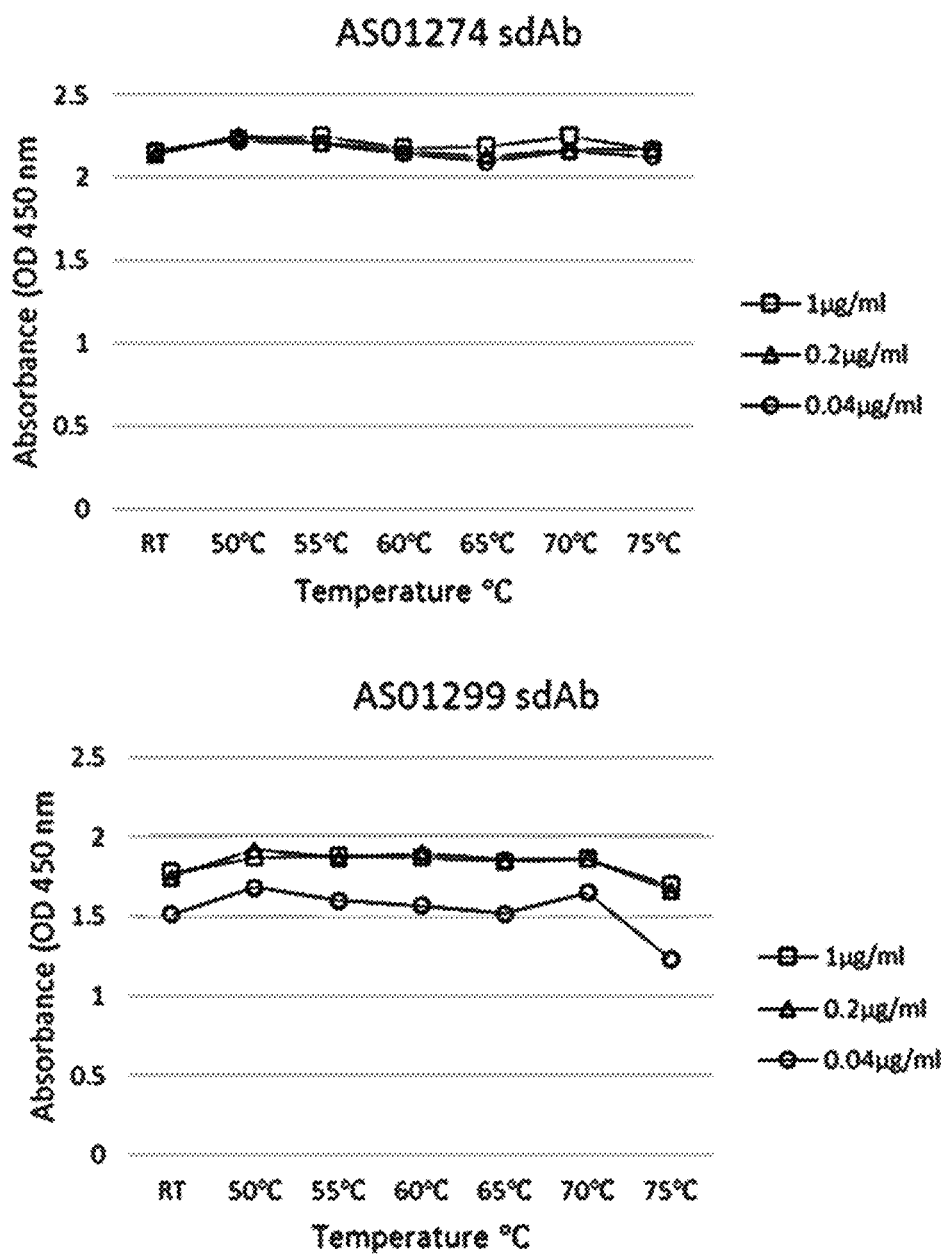
FIGS. 5A-5B show graphs of thermostability evaluation of AS01274 sdAb and AS01299 sdAb by ELISA.
Figure 5B:
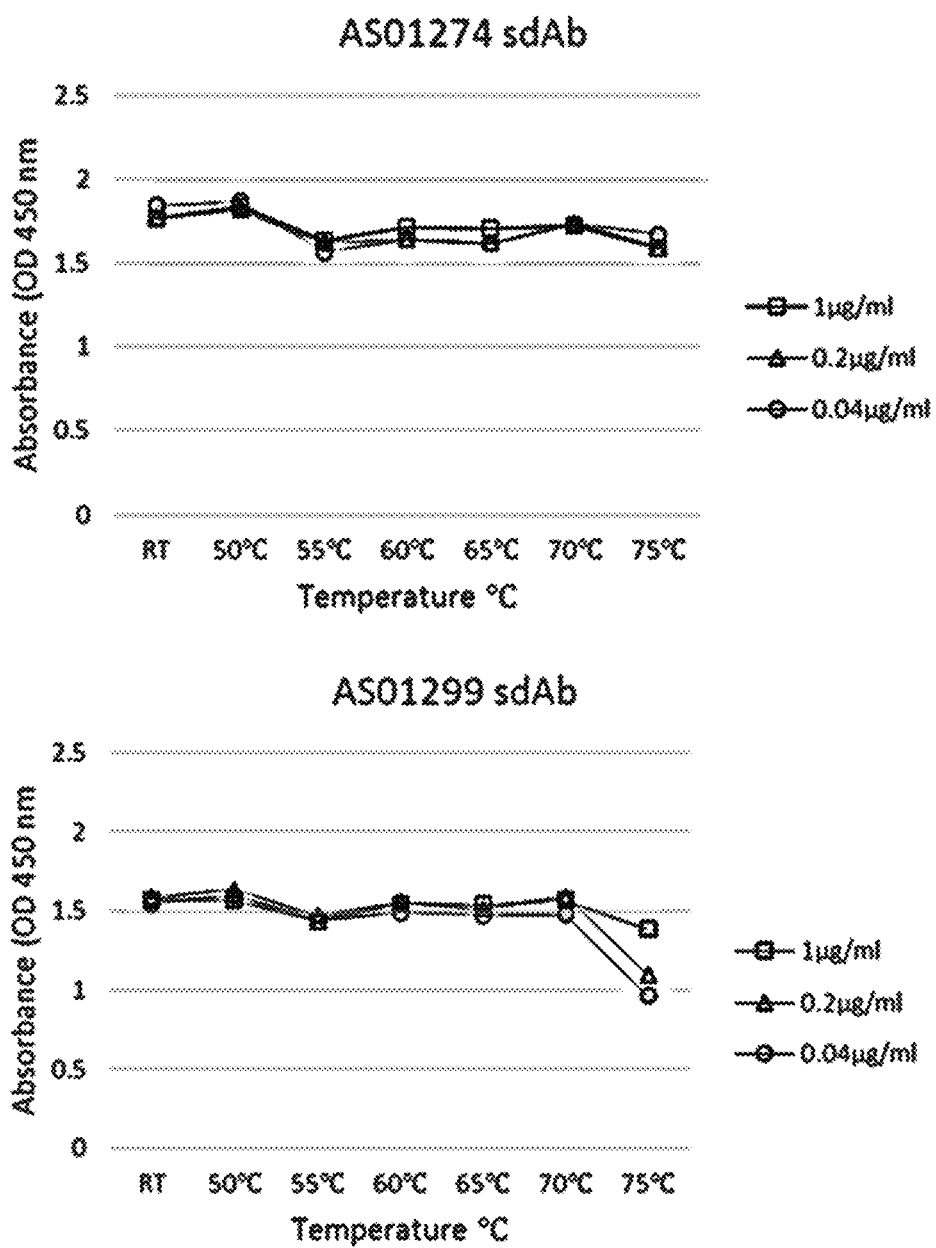

The thermostability of AS01274 sdAb and AS01299 sdAb were measured by ELISA. Three sdAb concentrations were used in this assay: 1 μg/ml; 0.2 μg/ml and 0.04 μg/ml. The purified AS01274 sdAb and AS01299 sdAb were diluted to the three concentrations mentioned above and were heated in water baths for 30 minutes at 50° C., 55° C., 60° C., 65° C., 70° C. and 75° C. All samples were allowed to cool to room temperature on the bench top. Samples were centrifuged to pellet aggregated material. Remaining soluble protein was assayed as primary antibodies for binding activity using ELISA. 96-well microtiter plates were coated with 2 μg/ml human transferrin and 2 μg/ml cynomolgus transferrin, respectively. The heated sdAb samples were added to the 96-well microtiter plates for binding evaluation. FIG. 5A shows the binding activity of human transferrin and FIG. 5B shows the binding activity of cynomolgus monkey transferrin.

Serum Clearance of sdAb AS01274 and AS01299

AS01274 and AS01299 were selected to test its serum half-life based on the transferrin binding activity, Protein A binding activity and high thermostability. Normally, sdAb is cleared from blood rapidly and the serum half-life is minutes to hours. To investigate the serum half-life of two selected sdAbs, the two sdAbs were fused to another sdAb (anti-IL-6R sdAb) with a very short serum half-life and produced as a sdAb fusion protein, respectively.

Figure 6:
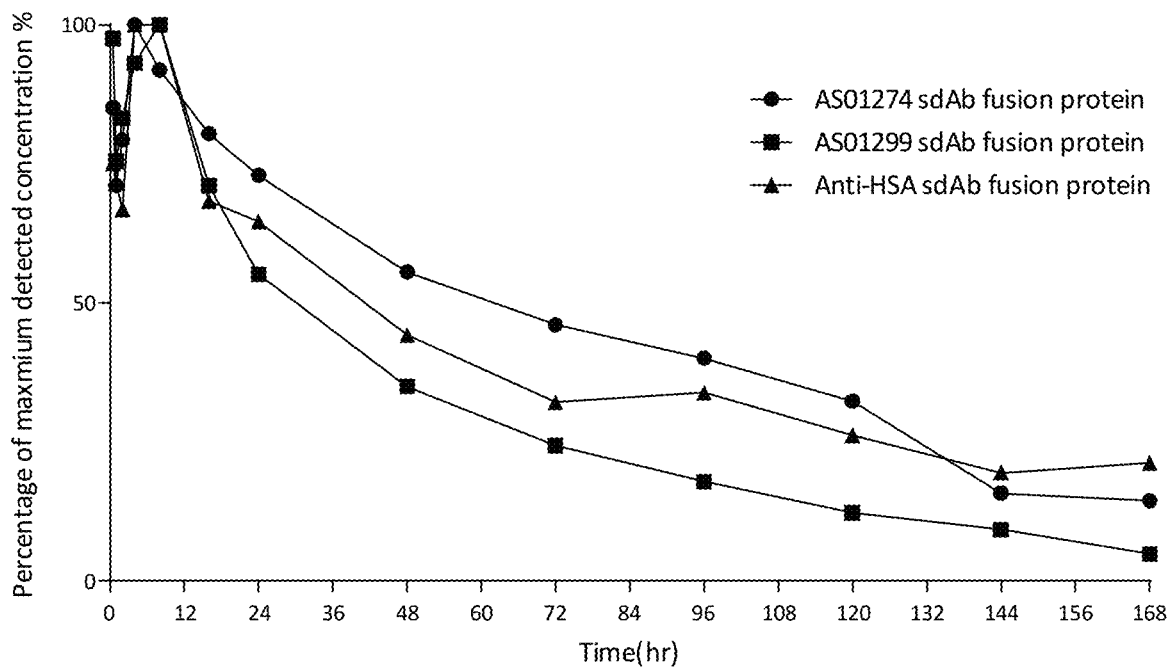
FIG. 6 shows the serum clearance of AS01274 sdAb fusion protein and AS01299 sdAb fusion protein after injection into a cynomolgus monkey. The blood sample was taken at the indicated time points and the concentrations of sdAb AS01274 and sdAb AS01299 were determined by enzyme linked immunosorbent assay (ELISA).

The AS01274 sdAb fusion protein and AS01299 sdAb fusion protein were injected into 4-5 kg Cynomolgus monkey for serum clearance analysis. AS01274 sdAb and AS01299 sdAb, by binding to transferrin, were able to significantly increase the serum half-life of the sdAb fusion protein from minutes to 2-3 days. Human serum albumin (HSA) is abundant in human serum and the HSA domain or fragments have been extensively used for serum half-life extension. In this experiment, the AS01274 sdAb fusion protein has comparable serum half-life to anti-HSA sdAb fusion protein. While the serum half-life for AS01299 sdAb is shorter than anti-HSA sdAb fusion protein (FIG. 6). The serum half-life was listed in Table 5.

TABLE 5

Serum half-life of selected sdAb fusion proteins

| Antibody | AS01274 sdAb fusion protein | AS01299 sdAb fusion protein | Anti-HSA sdAb fusion protein |
|---|---|---|---|
| $T_{(1/2)}$ (hours) | 66.869 | 41.221 | 73.903 |

Humanized Anti-Transferrin sdAb Characterization
Expression of Humanized Anti-Transferrin sdAbs AS01274 and AS01299 sdAbs were selected for humanization. Eight humanized sdAb variants were generated based on homology model and back mutations. The humanized sdAb variants include framework regions 1-4 (Table 6) and complementarity determining regions 1-3 (Table 7).

TABLE 6

Framework regions (FR) 1-4

| Ab ID | FR1 | NO | FR2 | NO | FR3 | NO | FR4 | NO |
|---|---|---|---|---|---|---|---|---|
| AS01274VHa | EVQLVESGGGLVQPGGSLRLSCAAS | 38 | WYRQAPGKGLELVA | 128 | RFTISRDNSKNTLYLQMNSLRAEDTAVYYCTD | 218 | WGQGTLVTVSS | 308 |
| AS01299VH3a | EVQLVESGGGLVQPGGSLRLSCAAS | 39 | WYRQAPGKGLELVA | 129 | RFTISRDNSKNTMYLQMNSLRAEDTAVYYCTD | 219 | WGQGTLVTVSS | 309 |
| AS01274VHa-A49 | EVQLVESGGGLVQPGGSLRLSCAAS | 40 | WYRQAPGKGLELVS | 130 | RFTISRDNSKNTLYLQMNSLRAEDTAVYYCTD | 220 | WGQGTLVTVSS | 310 |
| AS01299VH3a-A49 | EVQLVESGGGLVQPGGSLRLSCAAS | 41 | WYRQAPGKGLELVS | 131 | RFTISRDNSKNTMYLQMNSLRAEDTAVYYCTD | 221 | WGQGTLVTVSS | 311 |
| AS01299VH3a-L47 | EVQLVESGGGLVQPGGSLRLSCAAS | 42 | WYRQAPGKGLEWVA | 132 | RFTISRDNSKNTMYLQMNSLRAEDTAVYYCTD | 222 | WGQGTLVTVSS | 312 |
| AS01299VH3a-M78 | EVQLVESGGGLVQPGGSLRLSCAAS | 43 | WYRQAPGKGLELVA | 133 | RFTISRDNSKNTLYLQMNSLRAEDTAVYYCTD | 223 | WGQGTLVTVSS | 313 |
| AS01299VH4 | EVQLVESGGGLVQPGGSLRLSCAAS | 44 | WYRQAPGKGLELVS | 134 | RFTISRDNSKNTLYLQMNSLRAEDTAVYYCTD | 224 | WGQGTLVTVSS | 314 |
| AS01299VH4-LA7 | EVQLVESGGGLVQPGGSLRLSCAAS | 45 | WYRQAPGKGLEWVS | 135 | RFTISRDNSKNTLYLQMNSLRAEDTAVYYCTD | 225 | WGQGTLVTVSS | 315 |

TABLE 3

Complementarity determining regions 1-3 (CDRs 1-3)

| Ab ID | CDR1 | NO | CDR2 | NO | CDR3 | NO |
|---|---|---|---|---|---|---|
| AS01274VHa | GSIASIATMA | 83 | GITRGGSTKYADSVKG | 173 | YSRKYYQDY | 263 |
| AS01299VH3a | GSIFSIATMA | 84 | GITRSGSTNYRDSVKG | 174 | YSSRYYHDY | 264 |
| AS01274VHa-A49 | GSIASIATMA | 85 | GITRGGSTKYADSVKG | 175 | YSRKYYQDY | 265 |
| AS01299VH3a-A49 | GSIFSIATMA | 86 | GITRSGSTNYRDSVKG | 176 | YSSRYYHDY | 266 |
| AS01299VH3a-L47 | GSIFSIATMA | 87 | GITRSGSTNYRDSVKG | 177 | YSSRYYHDY | 267 |

TABLE 3-continued

Complementarity determining regions 1-3 (CDRs 1-3)

| Ab ID | CDR1 | NO | CDR2 | NO | CDR3 | NO |
|---|---|---|---|---|---|---|
| AS01299VH3a-M78 | GSIFSIATMA | 88 | GITRSGSTNYRDSVKG | 178 | YSSRYYHDY | 268 |
| AS01299VH4 | GSIFSIATMA | 89 | GITRSGSTNYRDSVKG | 179 | YSSRYYHDY | 269 |
| AS01299VH4-L47 | GSIFSIATMA | 90 | GITRSGSTNYRDSVKG | 180 | YSSRYYHDY | 270 |

Figure 7:
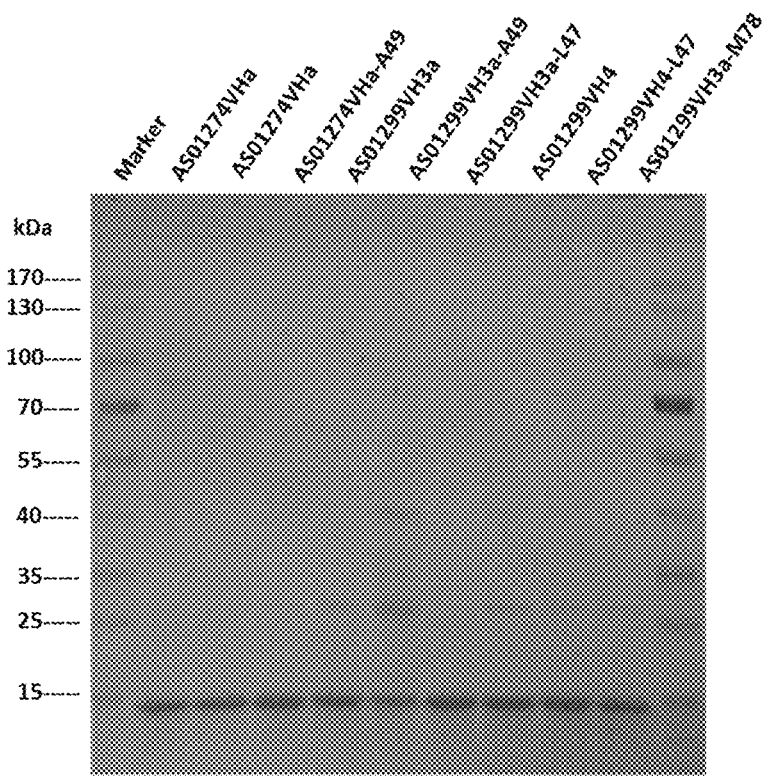
FIG. 7 is an image of an SDS polyacrylamide gel of purified sdAbs AS01274VHa, AS01274VHa-A49, AS01299VH3a, AS01299VH3a-A49, AS01299VH3a-L47, AS01299VH4, AS01299VH4-L47 and AS01299VH3a-M78, isolated from *Escherichia coli*, the amino acid sequences of which are shown in Table 1.
Figure 8A:
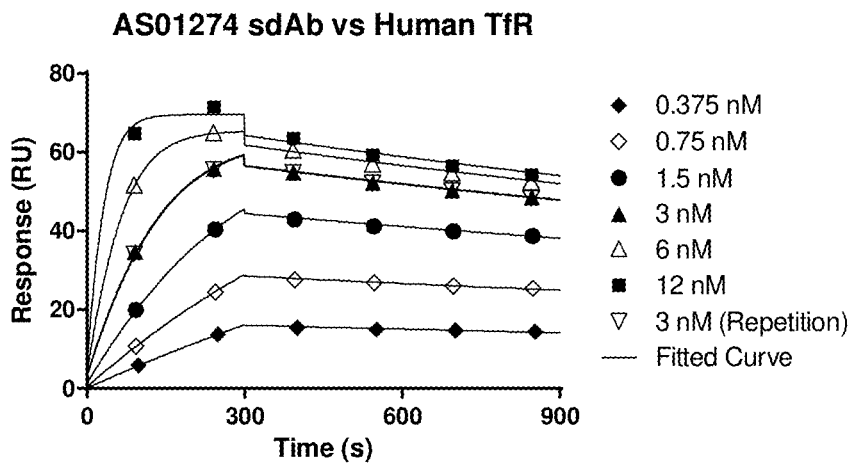
FIGS. 8A-8F show affinity determination of humanized anti-transferrin sdAbs binding to human transferrin and cynomolgus monkey transferrin, by BIAcore T200, along with their corresponding parent sdAb AS01274.
Figure 8B:
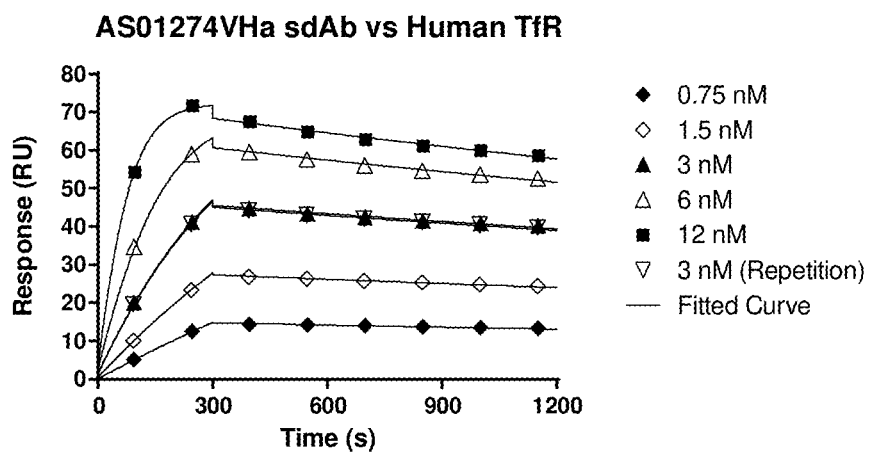
Figure 8C:
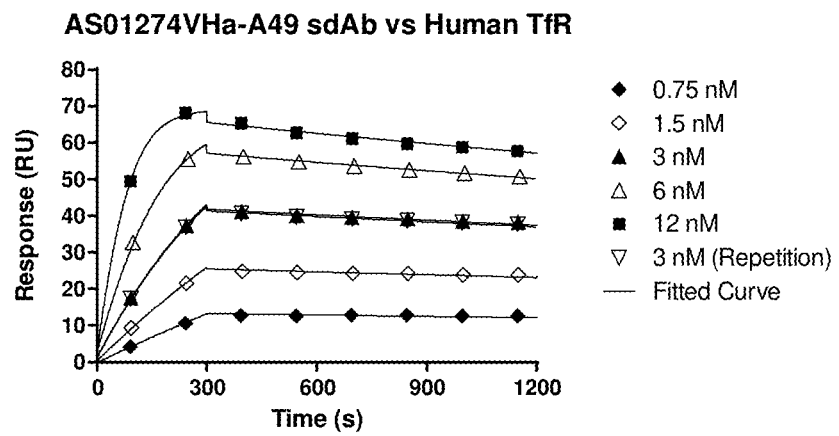
Figure 8D:
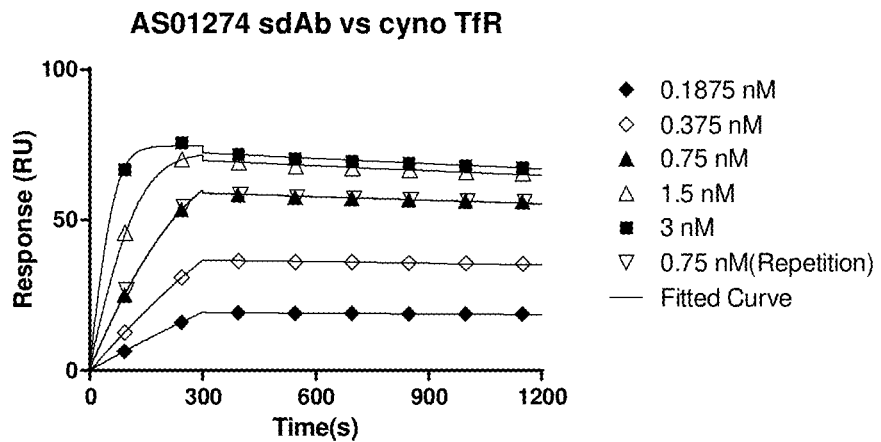
Figure 8E:
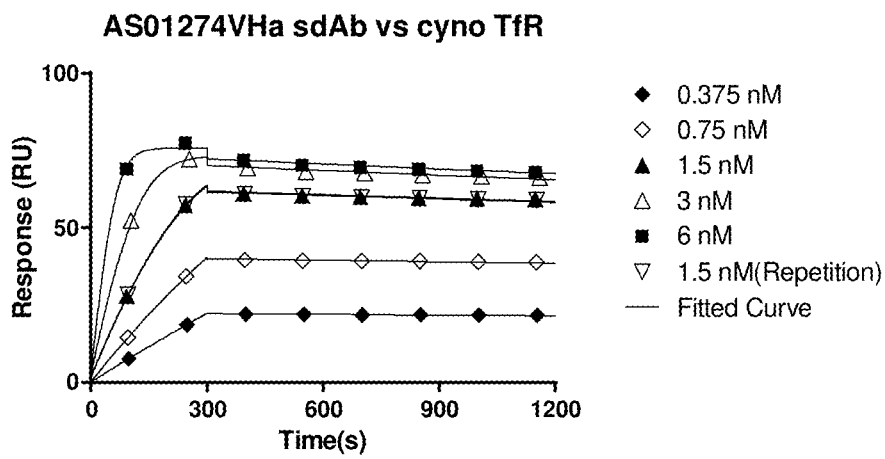
Figure 8F:
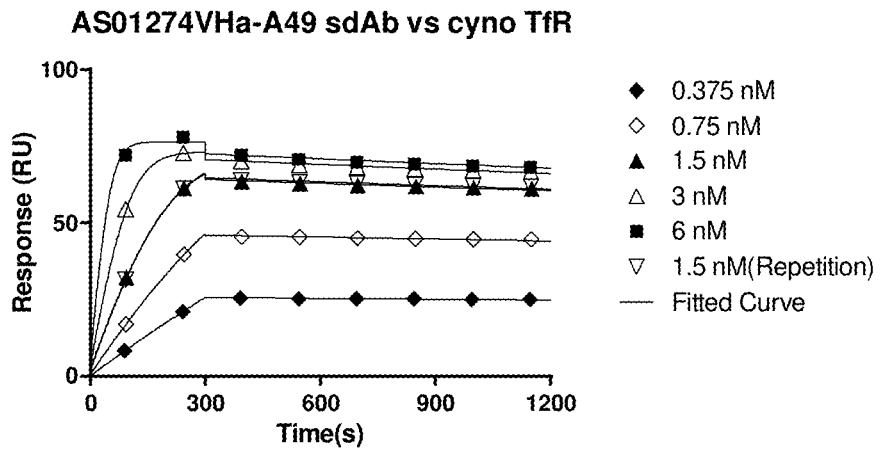
Figure 9A:
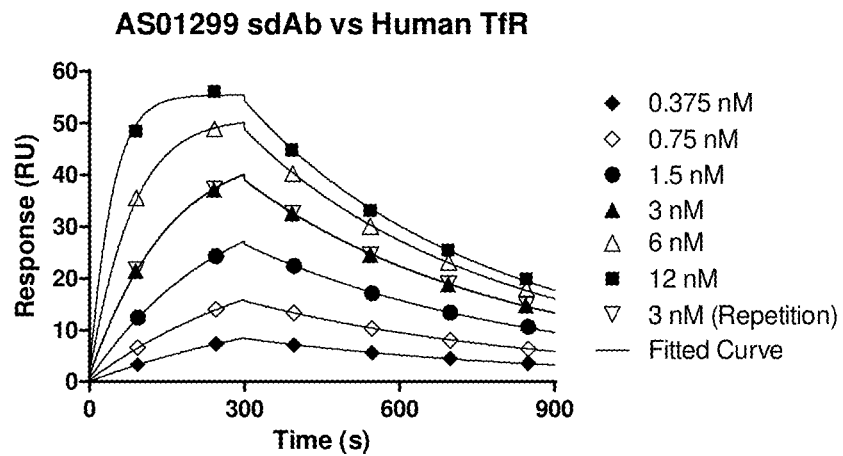
FIGS. 9A-9N show affinity determination of humanized anti-transferrin sdAbs binding to human transferrin and cynomolgus monkey transferrin, by BIAcore T200, along with their corresponding parent antibody.
Figure 9B:
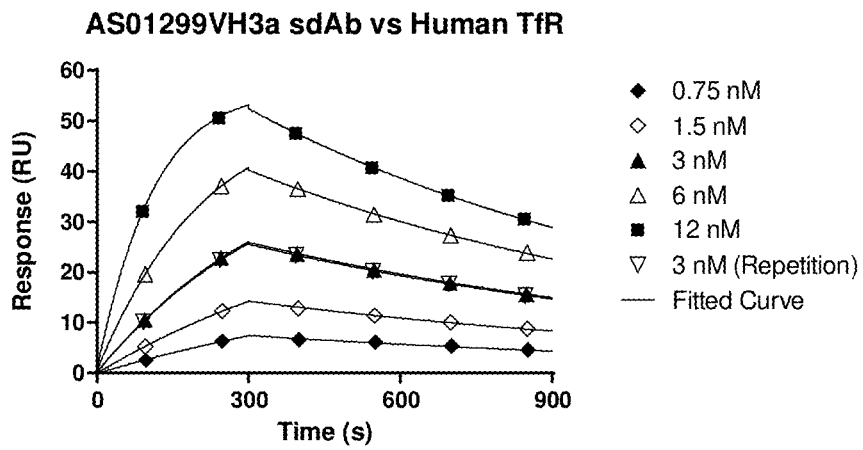
FIG. 9B: SPR sensorgram of sdAb AS01299VH3a binding to human transferrin at varying concentrations of sdAb, i.e., 0.75 nM, 1.5 nM, 3 nM, 6 nM and 12 nM from the top to the bottom of the plot.
Figure 9C:
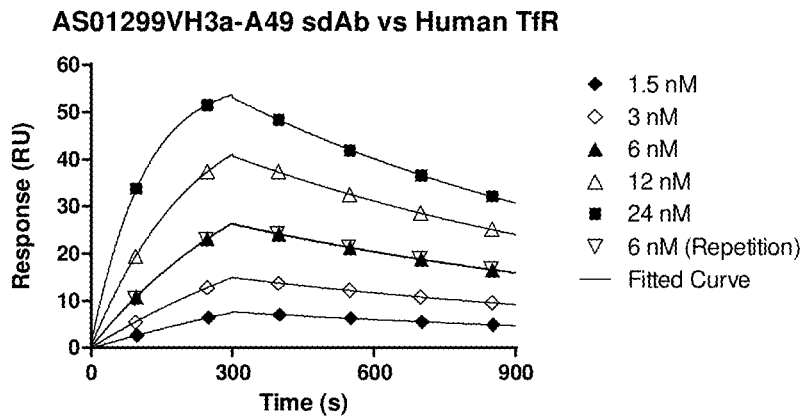
FIG. 9C: SPR sensorgram of sdAb AS01299VH3a-A49 binding to human transferrin at varying concentrations of sdAb, i.e., 1.5 nM, 3 nM, 6 nM, 12 nM and 24 nM from the top to the bottom of the plot.
Figure 9D:
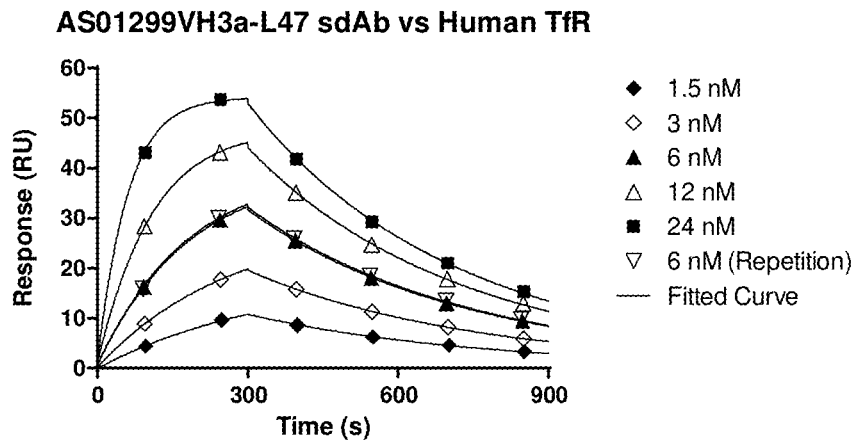
FIG. 9D: SPR sensorgram of sdAb AS01274VH3a-L47 binding to human transferrin at varying concentrations of sdAb, i.e., 1.5 nM, 3 nM, 6 nM, 12 nM and 24 nM from the top to the bottom of the plot.
Figure 9E:
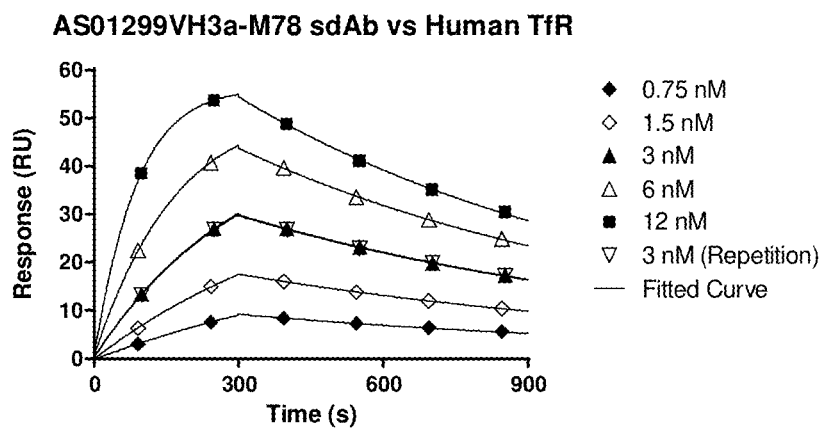
FIG. 9E: SPR sensorgram of sdAb AS01274VH3a-M78 binding to human transferrin at varying concentrations of sdAb, i.e., 0.75 nM, 1.5 nM, 3 nM, 6 nM and 12 nM from the top to the bottom of the plot.
Figure 9F:
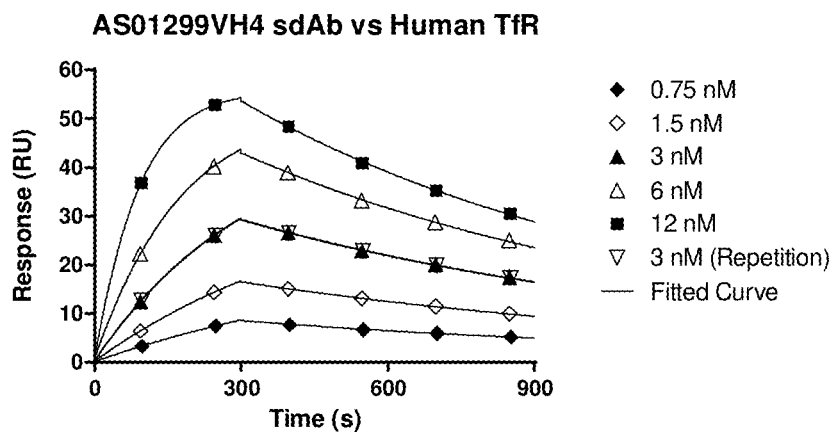
FIG. 9F: SPR sensorgram of sdAb AS01274VH4 binding to human transferrin at varying concentrations of sdAb, i.e., 0.75 nM, 1.5 nM, 3 nM, 6 nM and 12 nM from the top to the bottom of the plot.
Figure 9G:
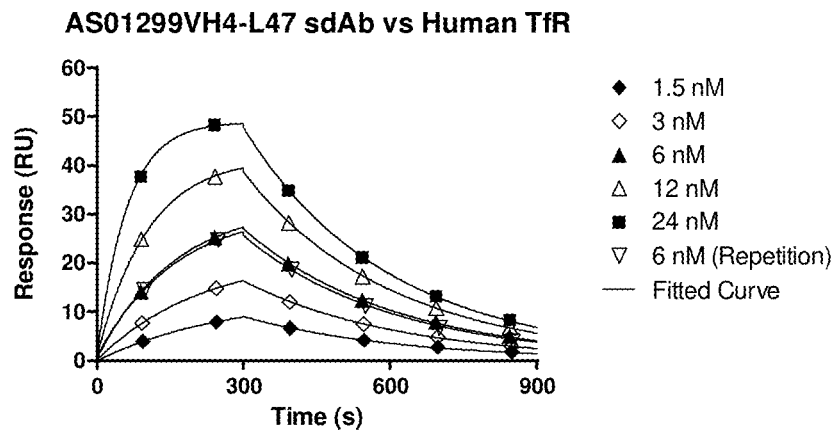
FIG. 9G: SPR sensorgram of sdAb AS01274VH4-L47 binding to human transferrin at varying concentrations of sdAb, i.e., 1.5 nM, 3 nM, 6 nM, 12 nM and 24 nM from the top to the bottom of the plot.
Figure 9H:
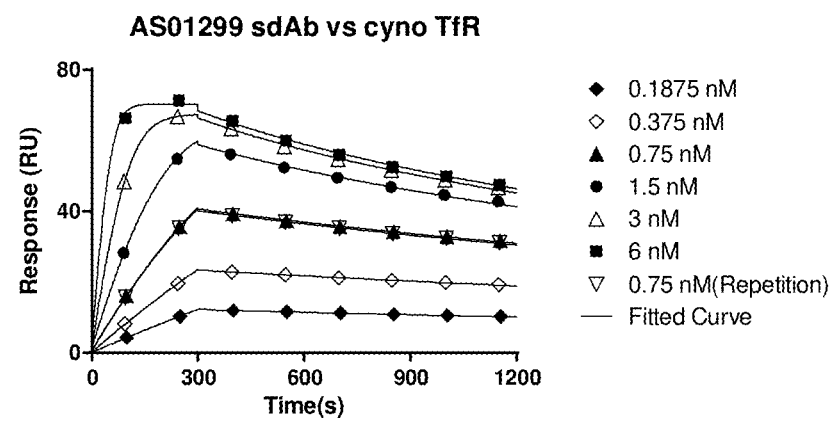
FIG. 9H: SPR sensorgram of sdAb AS01299 binding to cynomolgus monkey transferrin at varying concentrations of sdAb, i.e., 0.1875 nM, 0.375 nM, 0.75 nM, 1.5 nM, 3 nM and 6 nM from the top to the bottom of the plot.
Figure 9I:
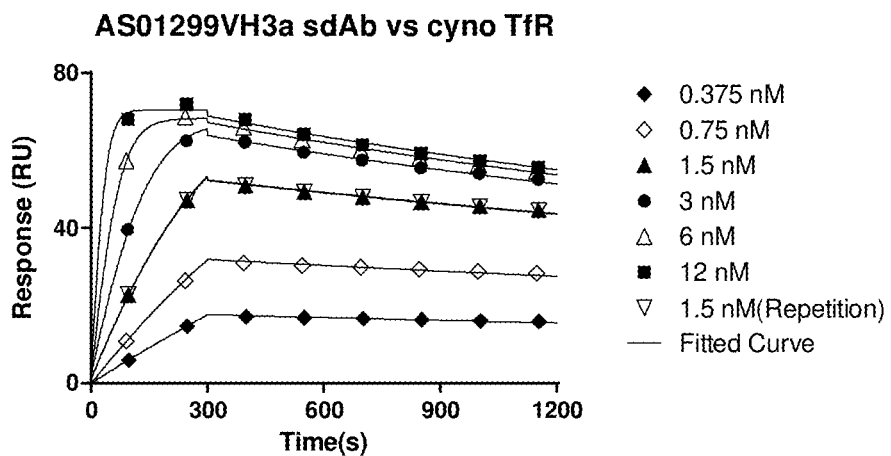
FIG. 9I: SPR sensorgram of sdAb AS01299VH3a binding to cynomolgus monkey transferrin at varying concentrations of sdAb, i.e., 0.375 nM, 0.75 nM, 1.5 nM, 3 nM, 6 nM and 12 nM from the top to the bottom of the plot.
Figure 9J:
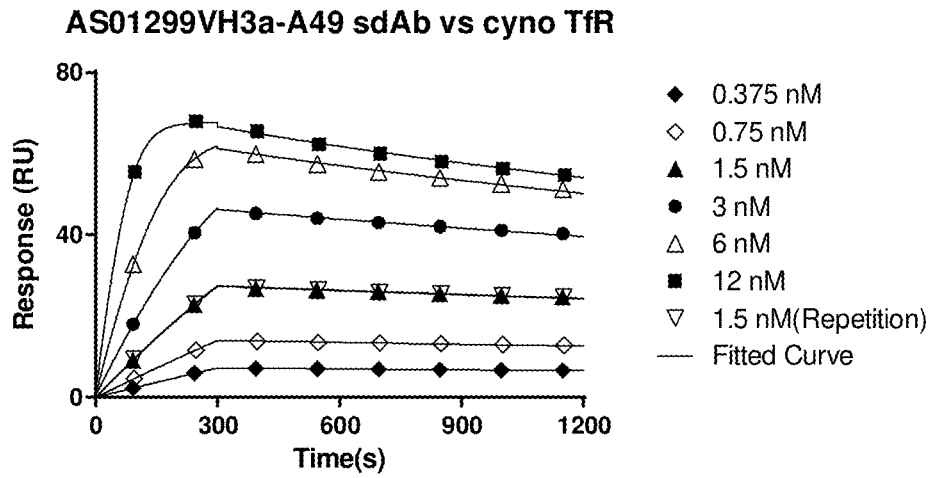
FIG. 9J: SPR sensorgram of sdAb AS01299VH3a-A49 binding to cynomolgus monkey transferrin at varying concentrations of sdAb, i.e., 0.375 nM, 0.75 nM, 1.5 nM, 3 nM, 6 nM and 12 nM from the top to the bottom of the plot.
Figure 9K:
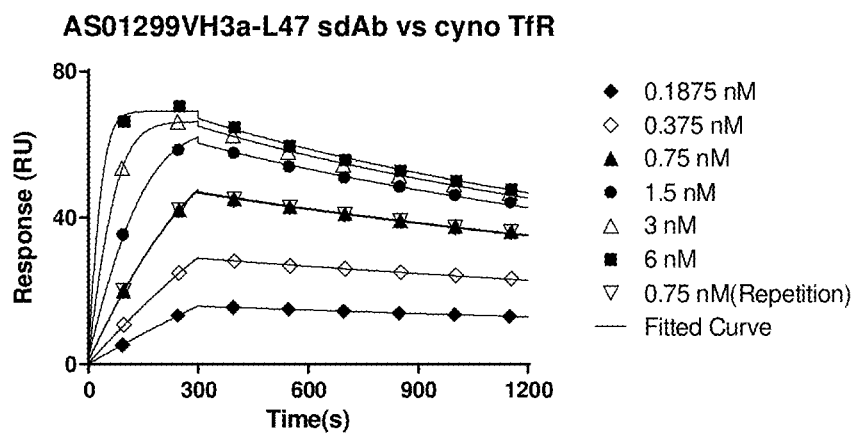
FIG. 9K: SPR sensorgram of sdAb AS01274VH3a-L47 binding to cynomolgus monkey transferrin at varying concentrations of sdAb, i.e., 0.1875 nM, 0.375 nM, 0.75 nM, 1.5 nM, 3 nM and 6 nM from the top to the bottom of the plot.
Figure 9L:
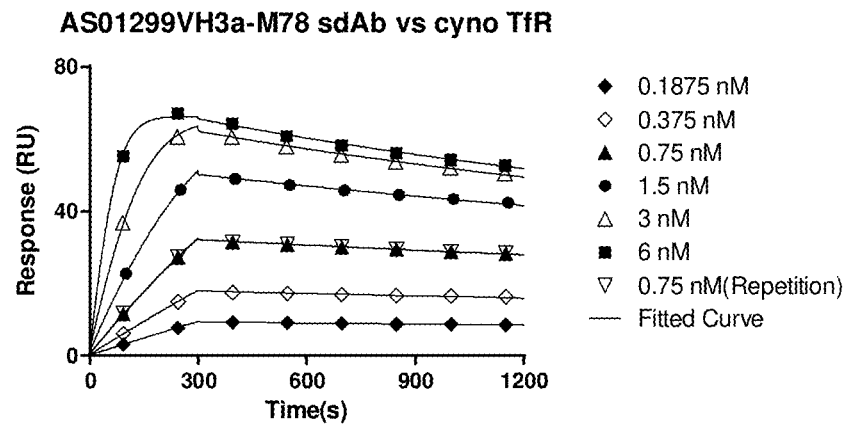
FIG. 9L: SPR sensorgram of sdAb AS01274VH3a-M78 binding to cynomolgus monkey transferrin at varying concentrations of sdAb, i.e., 0.1875 nM, 0.375 nM, 0.75 nM, 1.5 nM, 3 nM and 6 nM from the top to the bottom of the plot.
Figure 9M:
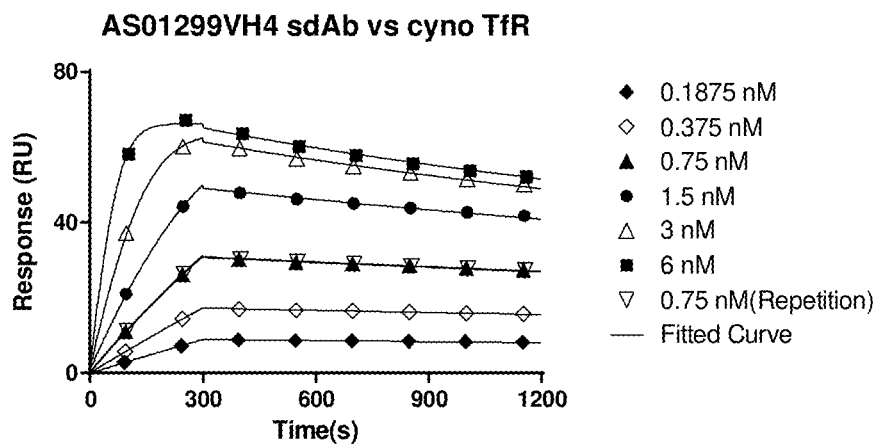
FIG. 9M: SPR sensorgram of sdAb AS01274VH4 binding to cynomolgus monkey transferrin at varying concentrations of sdAb, i.e., 0.1875 nM, 0.375 nM, 0.75 nM, 1.5 nM, 3 nM and 6 nM from the top to the bottom of the plot.
Figure 9N:
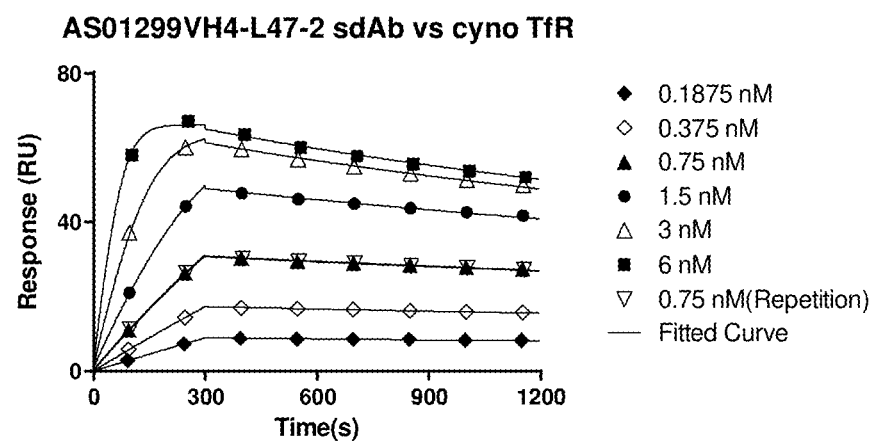

Eight sdAbs, AS01274VHa, AS01274VHa-A49, AS01299VH3a, AS01299VH3a-A49, AS01299VH3a-L47, AS01299VH4, AS01299VH4-L47 and AS01299VH3a-M78 were sub-cloned into an *E. coli* periplasmic expression vector, pSJF2H[I12]. The eight sdAbs, each tagged with a 6× histidine (His) tag at their C-terminal, were produced in *E. coli* and purified by IMAC (FIG. 7). The obtained sdAb amount from 1 L TG1 medium was listed in Table 8.

TABLE 8

Humanized sdAb production summary

| sdAb | AS01274VHa | AS01274VHa-A49 | AS01299VH3a | AS01299VH3a-A49 |
|---|---|---|---|---|
| Amount (mg) | 17.20 | 22.40 | 16.70 | 5.90 |

| sdAb | AS01299VH3a-L47 | AS01299VH4 | AS01299VH4-L47 | AS01299VH3a-M78 |
|---|---|---|---|---|
| Amount (mg) | 23.80 | 4.69 | 25.70 | 18.25 |

Affinity Determination

The 8 humanized anti-transferrin sdAbs mentioned above were analyzed for binding to human transferrin and cynomolgus monkey transferrin using a SPR-based biosensor along with their parent sdAbs. The results were in FIGS. 8 and 9. The association ($k_{on}$) rates, dissociation ($k_{off}$) rates and dissociation constants ($K_D$s) were listed in Table 9 (for human transferrin) and Table 6 (for cynomolgus monkey transferrin).

TABLE 9 affinity measurement of humanized sdAbs for human transferrin

| Ligand | Analyte (sdAb) | $k_a$ (1/Ms) | $k_d$ (1/s) | $K_D$ (M) |
|---|---|---|---|---|
| human transferrin | AS01274 | 3.3E+06 | 3.0E−04 | 9.0E−11 |
| | AS01274VHa | 1.5E+06 | 2.0E−04 | 1.3E−10 |
| | AS01274VHa-A49 | 1.5E+06 | 1.6E−04 | 1.1E−10 |
| | AS01299 | 2.2E+06 | 2.2E−03 | 9.8E−10 |
| | AS01299VH3a | 8.1E+05 | 1.1E−03 | 1.3E−09 |
| | AS01299VH3a-A49 | 4.2E+05 | 1.0E−03 | 2.4E−09 |
| | AS01299VH3a-L47-2 | 6.8E+05 | 2.5E−03 | 3.7E−09 |
| | AS01299VH3a-M78 | 1.0E+06 | 1.2E−03 | 1.1E−09 |
| | AS01299VH4 | 1.0E+06 | 1.1E−03 | 1.1E−09 |
| | AS01299VH4-L47-2 | 5.9E+05 | 3.5E−03 | 6.0E−09 |

TABLE 10 affinity measurement of humanized sdAbs for cynomolgus monkey transferrin

| Ligand | Analyte (sdAb) | $k_a$ (1/Ms) | $k_d$ (1/s) | $K_D$ (M) |
|---|---|---|---|---|
| cynomolgus monkey | AS01274 sdAb | 1.3E+07 | 8.9E−05 | 6.7E−12 |
| | AS01274VHa | 7.3E+06 | 8.1E−05 | 1.1E−11 |
| transferrin | AS01274VHa-A49 | 8.7E+06 | 7.9E−05 | 9.0E−12 |
| | AS01299 sdAb | 8.6E+06 | 5.6E−04 | 6.5E−11 |
| | AS01299VH3a | 4.9E+06 | 2.8E−04 | 5.7E−11 |
| | AS01299VH3a-A49 | 2.6E+06 | 2.7E−04 | 1.0E−10 |
| | AS01299VH3a-L47-2 | 8.9E+06 | 4.8E−04 | 5.3E−11 |
| | AS01299VH3a-M78 | 5.2E+06 | 3.0E−04 | 5.8E−11 |
| | AS01299VH4 | 5.7E+06 | 3.0E−04 | 5.4E−11 |
| | AS01299VH4-L47-2 | 9.3E+06 | 6.6E−04 | 7.1E−11 |

Protein a Binding Capacity Analysis

The static and dynamic protein A binding capacity of two humanized sdAbs were analyzed along with one protein A binding anti-HSA sdAb. The parameters were listed in the Table 11. The data indicated the protein A binding capacity of 2 humanized anti-transferrin sdAbs have similar behavior on static and dynamic protein binding capacity as anti-HSA sdAb fusion protein.

TABLE 11

Protein A binding capacity analysis of humanized anti-transferrin sdAbs

| Sample | AS01274VHa-A49 fusion protein | AS01299VH4 fusion protein | anti-HSA fusion protein |
|---|---|---|---|
| Static binding capacity (mg/ml gel) | 13.8 | 15.6 | 15.1 |
| 10% Dynamic binding capacity (mg/ml gel) | 17.7 | 19 | 16.5 |

Serum Clearance of sdAb AS01274VHa-A49 and AS01299VH4

Figure 10:
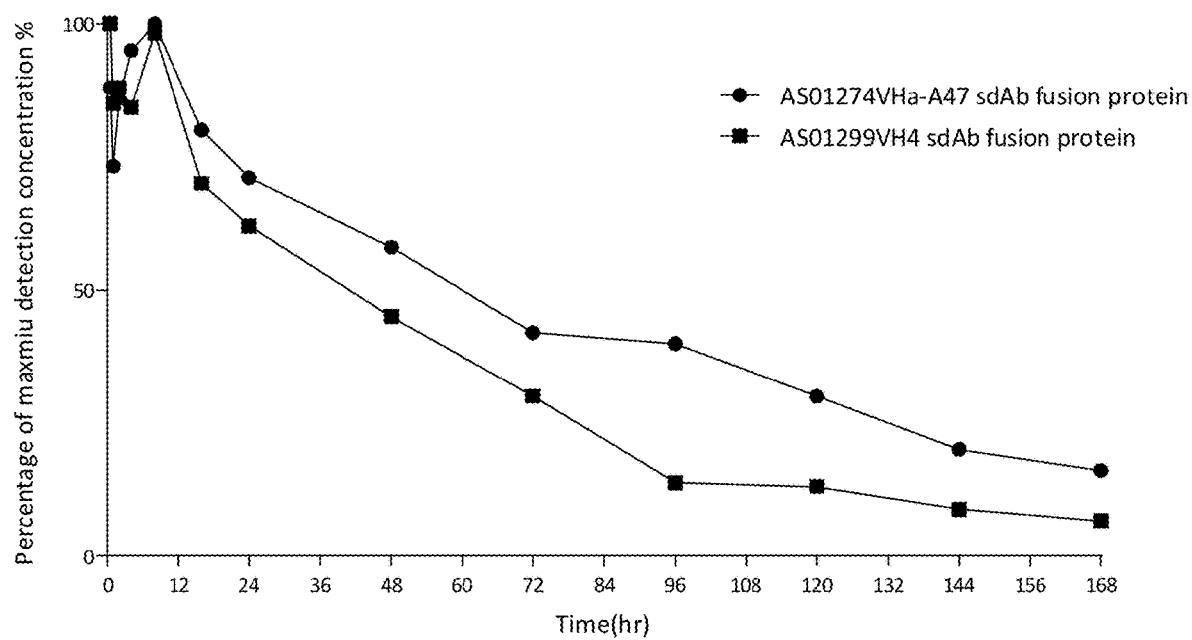
FIG. 10 shows the serum clearance of AS01274VHa-A47 sdAb fusion protein and AS01299VH4 sdAb fusion protein after injection into a cynomolgus monkey. The blood sample was taken at the indicated time points and the concentrations of sdAb AS01274VHa-A47 and sdAb AS01299VH4 were determined by enzyme linked immunosorbent assay (ELISA).

The AS01274VHa-A49 sdAb fusion protein and AS01299VH4 sdAb fusion protein were injected into 4-5 kg Cynomolgus monkey for serum clearance analysis. The serum sdAb fusion protein concentrations were shown in FIG. 10 following the first dosing. The calculated serum half-life was listed in Table 12. The data suggests the serum half-life of the two humanized anti-transferrin sdAbs was not effected after humanization.

TABLE 12

Serum half-life of humanized sdAb fusion proteins

| Antibody | AS01274 Vha-A49sdAb fusion protein | AS01299 VH4 sdAb fusion protein |
|---|---|---|
| $T_{(1/2)}$ (hours) | 60.23 | 42.35 |

REFERENCES

1. Sleep, D., J. Cameron, and L. R. Evans, *Albumin as a versatile platform for drug half-life extension*. Biochim Biophys Acta.
2. Kontermann, R. E., *Strategies for extended serum half-life of protein therapeutics*. Curr Opin Biotechnol. 22(6): p. 868-76.
3. Lee, L. S., et al., *Prolonged circulating lives of single-chain Fv proteins conjugated with polyethylene glycol: a comparison of conjugation chemistries and compounds*. Bioconjug Chem, 1999. 10(6): p. 973-81.
4. Tuettenberg, J., et al., *Pharmacokinetics, pharmacodynamics, safety and tolerability of APG101, a CD95-Fc fusion protein, in healthy volunteers and two glioma patients*. Int Immunopharmacol. 13(1): p. 93-100.
5. Nolte, M. W., et al., *Improved kinetics of rIX-FP, a recombinant fusion protein linking factor IX with albumin, in cynomolgus monkeys and hemophilia B dogs*. J Thromb Haemost. 10(8): p. 1591-9.
6. Holt, L. J., et al., *Anti-serum albumin domain antibodies for extending the half-lives of short lived drugs*. Protein Eng Des Sel, 2008. 21(5): p. 283-8.
7. Walker, A., et al., *Anti-serum albumin domain antibodies in the development of highly potent, efficacious and long-acting interferon*. Protein Eng Des Sel. 23(4): p. 271-8.
8. Stork, R., D. Muller, and R. E. Kontermann, *A novel tri-functional antibody fusion protein with improved pharmacokinetic properties generated by fusing a bispecific single-chain diabody with an albumin-binding domain from streptococcal protein G*. Protein Eng Des Sel, 2007. 20(11): p. 569-76.
9. Matsubara, M., et al., *Single dose GLP-1-Tf ameliorates myocardial ischemia/reperfusion injury*. J Surg Res. 165 (1): p. 38-45.
10. Keefe, D., et al., *In vitro characterization of an acetylcholine receptor-transferrin fusion protein for the treatment of myasthenia gravis*. Autoimmunity. 43(8): p. 628-39.
11. Arbabi Ghahroudi, M., et al., *Selection and identification of single domain antibody fragments from camel heavy-chain antibodies*. FEBS Lett, 1997. 414(3): p. 521-6.
12. Tanha, J., A. Muruganandam, and D. Stanimirovic, *Phage display technology for identifying specific antigens on brain endothelial cells*. Methods Mol Med, 2003. 89: p. 435-49.
13. Zhang, J., et al., *A pentavalent single-domain antibody approach to tumor antigen discovery and the development of novel proteomics reagents*. J Mol Biol, 2004. 341(1): p. 161-9.
14. Cortez-Retamozo, V., et al., *Efficient cancer therapy with a nanobody-based conjugate*. Cancer Res, 2004. 64(8): p. 2853-7.
15. Luo, F. R., et al., *Correlation of pharmacokinetics with the antitumor activity of Cetuximab in nude mice bearing the GEO human colon carcinoma xenograft*. Cancer Chemother Pharmacol, 2005. 56(5): p. 455-64.

We claim:

1. An isolated antibody or antigen-binding fragment thereof that specifically binds human and cynomolgus monkey serum transferrin protein and protein A resin, wherein the isolated antibody or antigen-binding fragment thereof can be purified by a protein A column, and wherein the isolated antibody or antigen-binding fragment thereof comprises:
   (a) a complementarity determining region (CDR)1 having an amino acid sequence selected from the group consisting of SEQ ID NO:46-SEQ ID NO:90;
   (b) a CDR2 having an amino acid sequence selected from the group consisting of SEQ ID NO:136-SEQ ID NO:180; and
   (c) a CDR3 having an amino acid sequence selected from the group consisting of SEQ ID NO:226-270.

2. The isolated antibody or antigen-binding fragment thereof of claim 1, wherein the isolated antibody or antigen-binding fragment thereof is a single-domain antibody (sdAb).

3. The isolated antibody or antigen-binding fragment thereof of claim 2, comprising an amino acid sequence at least 95% identical to a sequence selected from the group consisting of SEQ ID NO: 316-SEQ ID NO: 360.

4. The isolated antibody or antigen-binding fragment thereof of claim 3, comprising an amino acid sequence at least 95% identical to the amino acid sequence of

AS01274
(QVQLVESGGGLVQPGGSLRLSCVASGSIASIATMAWYRQAPGQQRELVA

GITRGGSTKYADSVKGRFTISRDNAKNTLYLQMNSLKPDDTAVYYCTDYS

RKYYQDYWGQGTQVTVSS (SEQ ID NO: 316));
or

AS01299
(QVQLVESGGGLVQPGGSLRLSCAASGSIFSIATMAWYRQAPGKQRELVA

GITRSGSTNYRDSVKGRFTISRDNAKNTMYLQMNSLKPEDTAVYYCTDYS

SRYYHDYWGQGTQVTVSS (SEQ ID NO: 332));
or

AS01299VH3a
(EVQLVESGGGLVQPGGSLRLSCAASGSIFSIATMAWYRQAPGKGLELVA

GITRSGSTNYRDSVKGRFTISRDNSKNTMYLQMNSLRAEDTAVYYCTDYS

SRYYHDYWGQGTLVTVSS (SEQ ID NO: 354);
or

AS01299VH3a-A49
(EVQLVESGGGLVQPGGSLRLSCAASGSIFSIATMAWYRQAPGKGLELVS

GITRSGSTNYRDSVKGRFTISRDNSKNTMYLQMNSLRAEDTAVYYCTDYS

SRYYHDYWGQGTLVTVSS (SEQ ID NO: 356));
or

-continued

AS01299VH3a-L47
(EVQLVESGGGLVQPGGSLRLSCAASGSIFSIATMAWYRQAPGKGLEWVA

GITRSGSTNYRDSVKGRFTISRDNSKNTMYLQMNSLRAEDTAVYYCTDYS

SRYYHDYWGQGTLVTVSS (SEQ ID NO: 357));
or

AS01299VH3a-M78
(EVQLVESGGGLVQPGGSLRLSCAASGSIFSIATMAWYRQAPGKGLELVA

GITRSGSTNYRDSVKGRFTISRDNSKNTLYLQMNSLRAEDTAVYYCTDYS

SRYYHDYWGQGTLVTVSS (SEQ ID NO: 358));
or

AS01299VH4
(EVQLVESGGGLVQPGGSLRLSCAASGSIFSIATMAWYRQAPGKGLELVS

GITRSGSTNYRDSVKGRFTISRDNSKNTLYLQMNSLRAEDTAVYYCTDYS

SRYYHDYWGQGTLVTVSS (SEQ ID NO: 359));
or

AS01299VH4-L47
(EVQLVESGGGLVQPGGSLRLSCAASGSIFSIATMAWYRQAPGKGLEWVS

GITRSGSTNYRDSVKGRFTISRDNSKNTLYLQMNSLRAEDTAVYYCTDYS

SRYYHDYWGQGTLVTVSS (SEQ ID NO: 360)).

5. The isolated antibody or antigen-binding fragment thereof of claim 1, having a dissociation constant ($K_D$) of $10^{-7}$ M or less.

6. The isolated antibody or antigen-binding fragment thereof of claim 1, wherein the isolated antibody or antigen-binding fragment thereof is produced recombinantly.

7. A fusion protein comprising the isolated antibody or antigen-binding fragment thereof of claim 1, a target protein, and a linker, wherein the isolated antibody or antigen-binding fragment thereof is fused to the carboxyl-terminus or amino-terminus of the target protein, and the linker separates the antibody and the carboxyl-terminus or amino-terminus of the target protein.

8. A composition comprising the fusion protein of claim 7 and transferrin.

9. A fusion protein comprising the isolated antibody or antigen-binding fragment thereof of claim 1, wherein the fusion protein is capable of being purified by protein A resin.

10. A method of increasing the half-life of a target protein in a fusion protein, the method comprising exposing the fusion protein of claim 7 to transferrin in cynomolgus monkey serum to thereby increase the half-life of the target protein in the fusion protein.

11. A method of producing the fusion protein of claim 7, comprising:
(a) obtaining an expression vector encoding the fusion protein;
(b) introducing the expression vector into a cell to obtain a recombinant cell;
(c) growing the recombinant cell under conditions to allow expression of the fusion protein; and
(d) obtaining the fusion protein from the recombinant cell or its supernatant.

12. A method for increasing the half-life of a target protein, the method comprising:
(1) obtaining a fusion protein, wherein the fusion protein comprises the isolated antibody or antigen-binding fragment thereof of claim 1, a target protein, and a linker, wherein the isolated antibody or antigen-binding fragment thereof is fused to the carboxyl-terminus or amino-terminus of the target protein, and the linker separates the isolated antibody or antigen-binding fragment thereof and the carboxyl-terminus or amino-terminus of the target protein, and
(2) exposing the fusion protein to transferrin,
wherein the transferrin increases the half-life of the target protein in the fusion protein compared to the target protein alone.

13. The method of claim 12, wherein the exposing step comprises administering the fusion protein to a serum comprising the transferrin of cynomolgus monkey.

14. A system for increasing the half-life of a target protein, the system comprising:
(a) a first nucleotide sequence encoding the isolated antibody or antigen-binding fragment thereof of claim 1, and a second nucleotide sequence encoding a linker, wherein the first and second nucleotide sequences are operably linked;
(b) a host cell; and
(c) transferrin.

* * * * *

SEQUENCE LISTING

```
<160> NUMBER OF SEQ ID NOS: 368

<210> SEQ ID NO 1
<211> LENGTH: 25
<212> TYPE: PRT
<213> ORGANISM: Artificial Sequence
<220> FEATURE:
<223> OTHER INFORMATION: FR1

<400> SEQUENCE: 1

Gln Val Gln Leu Val Glu Ser Gly Gly Gly Leu Val Gln Pro Gly Gly
1               5                   10                  15

Ser Leu Arg Leu Ser Cys Val Ala Ser
            20                  25

<210> SEQ ID NO 2
<211> LENGTH: 25
<212> TYPE: PRT
<213> ORGANISM: Artificial Sequence
<220> FEATURE:
<223> OTHER INFORMATION: FR1

<400> SEQUENCE: 2

Glu Val Gln Leu Val Glu Cys Gly Gly Gly Leu Val Gln Pro Gly Gly
```

```
1               5                   10                  15
Ser Leu Arg Leu Ser Cys Val Ala Ser
            20                  25

<210> SEQ ID NO 3
<211> LENGTH: 25
<212> TYPE: PRT
<213> ORGANISM: Artificial Sequence
<220> FEATURE:
<223> OTHER INFORMATION: FR1

<400> SEQUENCE: 3

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 4
<211> LENGTH: 25
<212> TYPE: PRT
<213> ORGANISM: Artificial Sequence
<220> FEATURE:
<223> OTHER INFORMATION: FR1

<400> SEQUENCE: 4

Glu Val Gln Leu Val Glu Cys Gly Gly Gly Leu Val Gln Pro Gly Gly
1               5                   10                  15

Ser Leu Arg Leu Ser Cys Ala Ala Ser
            20                  25

<210> SEQ ID NO 5
<211> LENGTH: 25
<212> TYPE: PRT
<213> ORGANISM: Artificial Sequence
<220> FEATURE:
<223> OTHER INFORMATION: FR1

<400> SEQUENCE: 5

Gln Val Lys Leu Glu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 6
<211> LENGTH: 25
<212> TYPE: PRT
<213> ORGANISM: Artificial Sequence
<220> FEATURE:
<223> OTHER INFORMATION: FR1

<400> SEQUENCE: 6

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 7
<211> LENGTH: 25
<212> TYPE: PRT
<213> ORGANISM: Artificial Sequence
<220> FEATURE:
<223> OTHER INFORMATION: FR1

<400> SEQUENCE: 7
```

-continued

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 8
<211> LENGTH: 25
<212> TYPE: PRT
<213> ORGANISM: Artificial Sequence
<220> FEATURE:
<223> OTHER INFORMATION: FR1

<400> SEQUENCE: 8

Gln Val Gln Leu Val Glu Ser Gly Gly Gly Leu Val Gln Pro Gly Gly
1               5                   10                  15

Ser Leu Arg Leu Ser Cys Val Ala Ser
            20                  25

<210> SEQ ID NO 9
<211> LENGTH: 25
<212> TYPE: PRT
<213> ORGANISM: Artificial Sequence
<220> FEATURE:
<223> OTHER INFORMATION: FR1

<400> SEQUENCE: 9

Gln Val Lys Leu Glu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 10
<211> LENGTH: 25
<212> TYPE: PRT
<213> ORGANISM: Artificial Sequence
<220> FEATURE:
<223> OTHER INFORMATION: FR1

<400> SEQUENCE: 10

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 11
<211> LENGTH: 25
<212> TYPE: PRT
<213> ORGANISM: Artificial Sequence
<220> FEATURE:
<223> OTHER INFORMATION: FR1

<400> SEQUENCE: 11

Gln Val Lys Leu Glu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 12
<211> LENGTH: 25
<212> TYPE: PRT
<213> ORGANISM: Artificial Sequence
<220> FEATURE:
<223> OTHER INFORMATION: FR1

<400> SEQUENCE: 12

His Val Gln Leu Val Glu Ser Gly Gly Gly Leu Val Gln Pro Gly Gly
1               5                   10                  15

Ser Leu Arg Leu Ser Cys Val Ala Ser
            20                  25

<210> SEQ ID NO 13
<211> LENGTH: 25
<212> TYPE: PRT
<213> ORGANISM: Artificial Sequence
<220> FEATURE:
<223> OTHER INFORMATION: FR1

<400> SEQUENCE: 13

Gln Val Gln Leu Val Glu Ser Gly Gly Gly Ser Val Gln Pro Gly Gly
1               5                   10                  15

Ser Leu Arg Leu Ser Cys Ala Ala Ser
            20                  25

<210> SEQ ID NO 14
<211> LENGTH: 25
<212> TYPE: PRT
<213> ORGANISM: Artificial Sequence
<220> FEATURE:
<223> OTHER INFORMATION: FR1

<400> SEQUENCE: 14

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 15
<211> LENGTH: 25
<212> TYPE: PRT
<213> ORGANISM: Artificial Sequence
<220> FEATURE:
<223> OTHER INFORMATION: FR1

<400> SEQUENCE: 15

Glu Val Gln Leu Val Glu Cys Gly Gly Gly Leu Val Gln Pro Gly Gly
1               5                   10                  15

Ser Leu Arg Leu Ser Cys Ala Ala Ser
            20                  25

<210> SEQ ID NO 16
<211> LENGTH: 25
<212> TYPE: PRT
<213> ORGANISM: Artificial Sequence
<220> FEATURE:
<223> OTHER INFORMATION: FR1

<400> SEQUENCE: 16

Gln Val Gln Leu Val Glu Ser Gly Gly Gly Leu Val Gln Ser Gly Gly
1               5                   10                  15

Ser Leu Arg Leu Ser Cys Ala Ala Ser
            20                  25

<210> SEQ ID NO 17
<211> LENGTH: 25
<212> TYPE: PRT
<213> ORGANISM: Artificial Sequence
<220> FEATURE:
<223> OTHER INFORMATION: FR1

```
<400> SEQUENCE: 17

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 18
<211> LENGTH: 25
<212> TYPE: PRT
<213> ORGANISM: Artificial Sequence
<220> FEATURE:
<223> OTHER INFORMATION: FR1

<400> SEQUENCE: 18

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 19
<211> LENGTH: 25
<212> TYPE: PRT
<213> ORGANISM: Artificial Sequence
<220> FEATURE:
<223> OTHER INFORMATION: FR1

<400> SEQUENCE: 19

Gln Val Lys Leu Glu Glu Ser Gly Gly Gly Leu Val Gln Pro Gly Gly
1               5                   10                  15

Ser Leu Thr Leu Ser Cys Ala Ala Ser
            20                  25

<210> SEQ ID NO 20
<211> LENGTH: 25
<212> TYPE: PRT
<213> ORGANISM: Artificial Sequence
<220> FEATURE:
<223> OTHER INFORMATION: FR1

<400> SEQUENCE: 20

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 21
<211> LENGTH: 25
<212> TYPE: PRT
<213> ORGANISM: Artificial Sequence
<220> FEATURE:
<223> OTHER INFORMATION: FR1

<400> SEQUENCE: 21

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 22
<211> LENGTH: 25
<212> TYPE: PRT
<213> ORGANISM: Artificial Sequence
<220> FEATURE:
<223> OTHER INFORMATION: FR1
```

<400> SEQUENCE: 22

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 23
<211> LENGTH: 25
<212> TYPE: PRT
<213> ORGANISM: Artificial Sequence
<220> FEATURE:
<223> OTHER INFORMATION: FR1

<400> SEQUENCE: 23

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 24
<211> LENGTH: 25
<212> TYPE: PRT
<213> ORGANISM: Artificial Sequence
<220> FEATURE:
<223> OTHER INFORMATION: FR1

<400> SEQUENCE: 24

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 25
<211> LENGTH: 25
<212> TYPE: PRT
<213> ORGANISM: Artificial Sequence
<220> FEATURE:
<223> OTHER INFORMATION: FR1

<400> SEQUENCE: 25

Gln Val Gln Leu Val Glu Ser Gly Gly Gly Leu Val Gln Ala Gly Gly
1               5                   10                  15

Ser Leu Arg Leu Ser Cys Val Ala Ser
            20                  25

<210> SEQ ID NO 26
<211> LENGTH: 25
<212> TYPE: PRT
<213> ORGANISM: Artificial Sequence
<220> FEATURE:
<223> OTHER INFORMATION: FR1

<400> SEQUENCE: 26

Glu Val Gln Leu Val Glu Cys Gly Gly Gly Leu Val Gln Pro Gly Gly
1               5                   10                  15

Ser Leu Arg Leu Ser Cys Ala Ala Ser
            20                  25

<210> SEQ ID NO 27
<211> LENGTH: 25
<212> TYPE: PRT
<213> ORGANISM: Artificial Sequence
<220> FEATURE:

<223> OTHER INFORMATION: FR1

<400> SEQUENCE: 27

Glu Val Gln Leu Val Glu Cys Gly Gly Gly Leu Val Gln Pro Gly Gly
1               5                   10                  15

Ser Leu Arg Leu Ser Cys Ala Ala Ser
            20                  25

<210> SEQ ID NO 28
<211> LENGTH: 25
<212> TYPE: PRT
<213> ORGANISM: Artificial Sequence
<220> FEATURE:
<223> OTHER INFORMATION: FR1

<400> SEQUENCE: 28

Gln Val Lys Leu Glu Glu Ser Gly Gly Gly Leu Val Gln Ala Gly Gly
1               5                   10                  15

Ser Leu Arg Leu Ser Cys Ala Ala Ser
            20                  25

<210> SEQ ID NO 29
<211> LENGTH: 25
<212> TYPE: PRT
<213> ORGANISM: Artificial Sequence
<220> FEATURE:
<223> OTHER INFORMATION: FR1

<400> SEQUENCE: 29

Glu Val Gln Leu Val Glu Cys Gly Gly Gly Leu Val Gln Pro Gly Gly
1               5                   10                  15

Ser Leu Arg Leu Ser Cys Ala Ala Ser
            20                  25

<210> SEQ ID NO 30
<211> LENGTH: 25
<212> TYPE: PRT
<213> ORGANISM: Artificial Sequence
<220> FEATURE:
<223> OTHER INFORMATION: FR1

<400> SEQUENCE: 30

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 31
<211> LENGTH: 25
<212> TYPE: PRT
<213> ORGANISM: Artificial Sequence
<220> FEATURE:
<223> OTHER INFORMATION: FR1

<400> SEQUENCE: 31

Glu Val Gln Leu Val Glu Cys Gly Gly Gly Leu Val Gln Pro Gly Gly
1               5                   10                  15

Ser Leu Arg Leu Ser Cys Ala Ala Ser
            20                  25

<210> SEQ ID NO 32
<211> LENGTH: 25
<212> TYPE: PRT
<213> ORGANISM: Artificial Sequence

```
<220> FEATURE:
<223> OTHER INFORMATION: FR1

<400> SEQUENCE: 32

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 33
<211> LENGTH: 25
<212> TYPE: PRT
<213> ORGANISM: Artificial Sequence
<220> FEATURE:
<223> OTHER INFORMATION: FR1

<400> SEQUENCE: 33

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 34
<211> LENGTH: 25
<212> TYPE: PRT
<213> ORGANISM: Artificial Sequence
<220> FEATURE:
<223> OTHER INFORMATION: FR1

<400> SEQUENCE: 34

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 35
<211> LENGTH: 25
<212> TYPE: PRT
<213> ORGANISM: Artificial Sequence
<220> FEATURE:
<223> OTHER INFORMATION: FR1

<400> SEQUENCE: 35

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 36
<211> LENGTH: 25
<212> TYPE: PRT
<213> ORGANISM: Artificial Sequence
<220> FEATURE:
<223> OTHER INFORMATION: FR1

<400> SEQUENCE: 36

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 37
<211> LENGTH: 25
<212> TYPE: PRT
```

<213> ORGANISM: Artificial Sequence
<220> FEATURE:
<223> OTHER INFORMATION: FR1

<400> SEQUENCE: 37

Gln Val Lys Leu Glu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 38
<211> LENGTH: 25
<212> TYPE: PRT
<213> ORGANISM: Artificial Sequence
<220> FEATURE:
<223> OTHER INFORMATION: FR1

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 39
<211> LENGTH: 25
<212> TYPE: PRT
<213> ORGANISM: Artificial Sequence
<220> FEATURE:
<223> OTHER INFORMATION: FR1

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 40
<211> LENGTH: 25
<212> TYPE: PRT
<213> ORGANISM: Artificial Sequence
<220> FEATURE:
<223> OTHER INFORMATION: FR1

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 41
<211> LENGTH: 25
<212> TYPE: PRT
<213> ORGANISM: Artificial Sequence
<220> FEATURE:
<223> OTHER INFORMATION: FR1

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 42
<211> LENGTH: 25

```
<212> TYPE: PRT
<213> ORGANISM: Artificial Sequence
<220> FEATURE:
<223> OTHER INFORMATION: FR1

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 43
<211> LENGTH: 25
<212> TYPE: PRT
<213> ORGANISM: Artificial Sequence
<220> FEATURE:
<223> OTHER INFORMATION: FR1

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 44
<211> LENGTH: 25
<212> TYPE: PRT
<213> ORGANISM: Artificial Sequence
<220> FEATURE:
<223> OTHER INFORMATION: FR1

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 45
<211> LENGTH: 25
<212> TYPE: PRT
<213> ORGANISM: Artificial Sequence
<220> FEATURE:
<223> OTHER INFORMATION: FR1

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 46
<211> LENGTH: 10
<212> TYPE: PRT
<213> ORGANISM: Artificial Sequence
<220> FEATURE:
<223> OTHER INFORMATION: CDR1

<400> SEQUENCE: 46

Gly Ser Ile Ala Ser Ile Ala Thr Met Ala
1               5                   10

<210> SEQ ID NO 47
<211> LENGTH: 10
<212> TYPE: PRT
<213> ORGANISM: Artificial Sequence
```

```
<220> FEATURE:
<223> OTHER INFORMATION: CDR1

<400> SEQUENCE: 47

Gly Ser Ile Ala Ser Ile Ala Thr Met Ala
1               5                   10

<210> SEQ ID NO 48
<211> LENGTH: 10
<212> TYPE: PRT
<213> ORGANISM: Artificial Sequence
<220> FEATURE:
<223> OTHER INFORMATION: CDR1

<400> SEQUENCE: 48

Gly Ser Ile Phe Ser Ile Asn Thr Met Ala
1               5                   10

<210> SEQ ID NO 49
<211> LENGTH: 10
<212> TYPE: PRT
<213> ORGANISM: Artificial Sequence
<220> FEATURE:
<223> OTHER INFORMATION: CDR1

<400> SEQUENCE: 49

Gly Ser Ile Phe Ser Ile Asn Thr Met Gly
1               5                   10

<210> SEQ ID NO 50
<211> LENGTH: 10
<212> TYPE: PRT
<213> ORGANISM: Artificial Sequence
<220> FEATURE:
<223> OTHER INFORMATION: CDR1

<400> SEQUENCE: 50

Gly Ser Ile Phe Ser Ile Asn Thr Met Gly
1               5                   10

<210> SEQ ID NO 51
<211> LENGTH: 10
<212> TYPE: PRT
<213> ORGANISM: Artificial Sequence
<220> FEATURE:
<223> OTHER INFORMATION: CDR1

<400> SEQUENCE: 51

Gly Ser Ile Arg Pro Leu Arg Phe Met Ala
1               5                   10

<210> SEQ ID NO 52
<211> LENGTH: 10
<212> TYPE: PRT
<213> ORGANISM: Artificial Sequence
<220> FEATURE:
<223> OTHER INFORMATION: CDR1

<400> SEQUENCE: 52

Gly Ser Ile Gly Ser Ser Ala Thr Met Ala
1               5                   10

<210> SEQ ID NO 53
<211> LENGTH: 10
<212> TYPE: PRT
<213> ORGANISM: Artificial Sequence
<220> FEATURE:
```

<223> OTHER INFORMATION: CDR1

<400> SEQUENCE: 53

Gly Ser Ile Phe Ser Ile Asn Thr Met Gly
1               5                   10

<210> SEQ ID NO 54
<211> LENGTH: 10
<212> TYPE: PRT
<213> ORGANISM: Artificial Sequence
<220> FEATURE:
<223> OTHER INFORMATION: CDR1

<400> SEQUENCE: 54

Gly Ser Ile Phe Ser Ile Ala Thr Met Ala
1               5                   10

<210> SEQ ID NO 55
<211> LENGTH: 10
<212> TYPE: PRT
<213> ORGANISM: Artificial Sequence
<220> FEATURE:
<223> OTHER INFORMATION: CDR1

<400> SEQUENCE: 55

Arg Ser Ile Ser Thr Leu Arg Phe Met Ala
1               5                   10

<210> SEQ ID NO 56
<211> LENGTH: 10
<212> TYPE: PRT
<213> ORGANISM: Artificial Sequence
<220> FEATURE:
<223> OTHER INFORMATION: CDR1

<400> SEQUENCE: 56

Gly Ser Ile Val Ser Ile Ala Thr Met Ala
1               5                   10

<210> SEQ ID NO 57
<211> LENGTH: 10
<212> TYPE: PRT
<213> ORGANISM: Artificial Sequence
<220> FEATURE:
<223> OTHER INFORMATION: CDR1

<400> SEQUENCE: 57

Gly Ser Ile Ala Ser Val Ala Thr Met Ala
1               5                   10

<210> SEQ ID NO 58
<211> LENGTH: 10
<212> TYPE: PRT
<213> ORGANISM: Artificial Sequence
<220> FEATURE:
<223> OTHER INFORMATION: CDR1

<400> SEQUENCE: 58

Gly Ser Ile Ala Ser Ile Asn Thr Met Ala
1               5                   10

<210> SEQ ID NO 59
<211> LENGTH: 10
<212> TYPE: PRT
<213> ORGANISM: Artificial Sequence
<220> FEATURE:
<223> OTHER INFORMATION: CDR1

<400> SEQUENCE: 59

Gly Ser Ile Phe Ser Ile Asn Thr Met Ala
1               5                   10

<210> SEQ ID NO 60
<211> LENGTH: 10
<212> TYPE: PRT
<213> ORGANISM: Artificial Sequence
<220> FEATURE:
<223> OTHER INFORMATION: CDR1

<400> SEQUENCE: 60

Gly Ser Ile Phe Ser Ile Ala Thr Met Ala
1               5                   10

<210> SEQ ID NO 61
<211> LENGTH: 10
<212> TYPE: PRT
<213> ORGANISM: Artificial Sequence
<220> FEATURE:
<223> OTHER INFORMATION: CDR1

<400> SEQUENCE: 61

Gly Thr Ile Phe Ala Ile Asn Thr Met Ala
1               5                   10

<210> SEQ ID NO 62
<211> LENGTH: 10
<212> TYPE: PRT
<213> ORGANISM: Artificial Sequence
<220> FEATURE:
<223> OTHER INFORMATION: CDR1

<400> SEQUENCE: 62

Gly Ser Ile Phe Ser Ile Ala Thr Met Ala
1               5                   10

<210> SEQ ID NO 63
<211> LENGTH: 10
<212> TYPE: PRT
<213> ORGANISM: Artificial Sequence
<220> FEATURE:
<223> OTHER INFORMATION: CDR1

<400> SEQUENCE: 63

Gly Ser Ile Ala Ser Ile Asn Thr Met Ala
1               5                   10

<210> SEQ ID NO 64
<211> LENGTH: 10
<212> TYPE: PRT
<213> ORGANISM: Artificial Sequence
<220> FEATURE:
<223> OTHER INFORMATION: CDR1

<400> SEQUENCE: 64

Gly Ser Ile Phe Ser Ile Asn Thr Met Ala
1               5                   10

<210> SEQ ID NO 65
<211> LENGTH: 10
<212> TYPE: PRT
<213> ORGANISM: Artificial Sequence
<220> FEATURE:
<223> OTHER INFORMATION: CDR1

```
<400> SEQUENCE: 65

Gly Ser Ile Ala Ser Ile Asn Thr Met Ala
1               5                   10

<210> SEQ ID NO 66
<211> LENGTH: 10
<212> TYPE: PRT
<213> ORGANISM: Artificial Sequence
<220> FEATURE:
<223> OTHER INFORMATION: CDR1

<400> SEQUENCE: 66

Gly Ser Ile Phe Ser Ile Asn Thr Met Gly
1               5                   10

<210> SEQ ID NO 67
<211> LENGTH: 10
<212> TYPE: PRT
<213> ORGANISM: Artificial Sequence
<220> FEATURE:
<223> OTHER INFORMATION: CDR1

<400> SEQUENCE: 67

Gly Ser Ile Phe Ser Ile Asn Thr Met Gly
1               5                   10

<210> SEQ ID NO 68
<211> LENGTH: 10
<212> TYPE: PRT
<213> ORGANISM: Artificial Sequence
<220> FEATURE:
<223> OTHER INFORMATION: CDR1

<400> SEQUENCE: 68

Gly Ser Ile Ala Ser Ile Asn Thr Met Ala
1               5                   10

<210> SEQ ID NO 69
<211> LENGTH: 10
<212> TYPE: PRT
<213> ORGANISM: Artificial Sequence
<220> FEATURE:
<223> OTHER INFORMATION: CDR1

<400> SEQUENCE: 69

Gly Ser Ile Phe Ser Ile Asn Thr Met Gly
1               5                   10

<210> SEQ ID NO 70
<211> LENGTH: 10
<212> TYPE: PRT
<213> ORGANISM: Artificial Sequence
<220> FEATURE:
<223> OTHER INFORMATION: CDR1

<400> SEQUENCE: 70

Gly Ser Ile Ala Ser Ile Ala Thr Met Ala
1               5                   10

<210> SEQ ID NO 71
<211> LENGTH: 10
<212> TYPE: PRT
<213> ORGANISM: Artificial Sequence
<220> FEATURE:
<223> OTHER INFORMATION: CDR1

<400> SEQUENCE: 71
```

```
Gly Ser Ile Ala Ser Ile Asn Thr Met Ala
1               5                   10

<210> SEQ ID NO 72
<211> LENGTH: 10
<212> TYPE: PRT
<213> ORGANISM: Artificial Sequence
<220> FEATURE:
<223> OTHER INFORMATION: CDR1

<400> SEQUENCE: 72

Gly Ser Ile Ala Gly Ile Asn Thr Met Ala
1               5                   10

<210> SEQ ID NO 73
<211> LENGTH: 10
<212> TYPE: PRT
<213> ORGANISM: Artificial Sequence
<220> FEATURE:
<223> OTHER INFORMATION: CDR1

<400> SEQUENCE: 73

Gly Arg Thr Phe Ser Ser His Thr Met Gly
1               5                   10

<210> SEQ ID NO 74
<211> LENGTH: 10
<212> TYPE: PRT
<213> ORGANISM: Artificial Sequence
<220> FEATURE:
<223> OTHER INFORMATION: CDR1

<400> SEQUENCE: 74

Gly Ser Ile Ala Ser Ile Asn Thr Met Ala
1               5                   10

<210> SEQ ID NO 75
<211> LENGTH: 10
<212> TYPE: PRT
<213> ORGANISM: Artificial Sequence
<220> FEATURE:
<223> OTHER INFORMATION: CDR1

<400> SEQUENCE: 75

Gly Ser Ile Phe Ser Ile Asn Thr Met Ala
1               5                   10

<210> SEQ ID NO 76
<211> LENGTH: 10
<212> TYPE: PRT
<213> ORGANISM: Artificial Sequence
<220> FEATURE:
<223> OTHER INFORMATION: CDR1

<400> SEQUENCE: 76

Gly Ser Ile Ala Ser Ile Asn Thr Met Ala
1               5                   10

<210> SEQ ID NO 77
<211> LENGTH: 10
<212> TYPE: PRT
<213> ORGANISM: Artificial Sequence
<220> FEATURE:
<223> OTHER INFORMATION: CDR1

<400> SEQUENCE: 77
```

```
Gly Ser Ile Ala Ser Ile Asn Thr Met Ala
1               5                   10

<210> SEQ ID NO 78
<211> LENGTH: 10
<212> TYPE: PRT
<213> ORGANISM: Artificial Sequence
<220> FEATURE:
<223> OTHER INFORMATION: CDR1

<400> SEQUENCE: 78

Gly Ser Ile Ala Ser Ile Asn Thr Met Ala
1               5                   10

<210> SEQ ID NO 79
<211> LENGTH: 10
<212> TYPE: PRT
<213> ORGANISM: Artificial Sequence
<220> FEATURE:
<223> OTHER INFORMATION: CDR1

<400> SEQUENCE: 79

Gly Ser Ile Ala Ser Ile Asn Thr Met Ala
1               5                   10

<210> SEQ ID NO 80
<211> LENGTH: 10
<212> TYPE: PRT
<213> ORGANISM: Artificial Sequence
<220> FEATURE:
<223> OTHER INFORMATION: CDR1

<400> SEQUENCE: 80

Gly Ser Ile Ala Ser Ile Asn Thr Met Ala
1               5                   10

<210> SEQ ID NO 81
<211> LENGTH: 10
<212> TYPE: PRT
<213> ORGANISM: Artificial Sequence
<220> FEATURE:
<223> OTHER INFORMATION: CDR1

<400> SEQUENCE: 81

Gly Ser Ile Ala Ser Ile Asn Thr Met Ala
1               5                   10

<210> SEQ ID NO 82
<211> LENGTH: 10
<212> TYPE: PRT
<213> ORGANISM: Artificial Sequence
<220> FEATURE:
<223> OTHER INFORMATION: CDR1

<400> SEQUENCE: 82

Gly Ser Ile Ala Ser Ile Asn Thr Met Ala
1               5                   10

<210> SEQ ID NO 83
<211> LENGTH: 10
<212> TYPE: PRT
<213> ORGANISM: Artificial Sequence
<220> FEATURE:
<223> OTHER INFORMATION: CDR1

<400> SEQUENCE: 83

Gly Ser Ile Ala Ser Ile Ala Thr Met Ala
```

-continued

```
<210> SEQ ID NO 84
<211> LENGTH: 10
<212> TYPE: PRT
<213> ORGANISM: Artificial Sequence
<220> FEATURE:
<223> OTHER INFORMATION: CDR1

<400> SEQUENCE: 84

Gly Ser Ile Phe Ser Ile Ala Thr Met Ala
1               5                   10

<210> SEQ ID NO 85
<211> LENGTH: 10
<212> TYPE: PRT
<213> ORGANISM: Artificial Sequence
<220> FEATURE:
<223> OTHER INFORMATION: CDR1

<400> SEQUENCE: 85

Gly Ser Ile Ala Ser Ile Ala Thr Met Ala
1               5                   10

<210> SEQ ID NO 86
<211> LENGTH: 10
<212> TYPE: PRT
<213> ORGANISM: Artificial Sequence
<220> FEATURE:
<223> OTHER INFORMATION: CDR1

<400> SEQUENCE: 86

Gly Ser Ile Phe Ser Ile Ala Thr Met Ala
1               5                   10

<210> SEQ ID NO 87
<211> LENGTH: 10
<212> TYPE: PRT
<213> ORGANISM: Artificial Sequence
<220> FEATURE:
<223> OTHER INFORMATION: CDR1

<400> SEQUENCE: 87

Gly Ser Ile Phe Ser Ile Ala Thr Met Ala
1               5                   10

<210> SEQ ID NO 88
<211> LENGTH: 10
<212> TYPE: PRT
<213> ORGANISM: Artificial Sequence
<220> FEATURE:
<223> OTHER INFORMATION: CDR1

<400> SEQUENCE: 88

Gly Ser Ile Phe Ser Ile Ala Thr Met Ala
1               5                   10

<210> SEQ ID NO 89
<211> LENGTH: 10
<212> TYPE: PRT
<213> ORGANISM: Artificial Sequence
<220> FEATURE:
<223> OTHER INFORMATION: CDR1

<400> SEQUENCE: 89

Gly Ser Ile Phe Ser Ile Ala Thr Met Ala
1               5                   10
```

<210> SEQ ID NO 90
<211> LENGTH: 10
<212> TYPE: PRT
<213> ORGANISM: Artificial Sequence
<220> FEATURE:
<223> OTHER INFORMATION: CDR1

<400> SEQUENCE: 90

Gly Ser Ile Phe Ser Ile Ala Thr Met Ala
1               5                   10

<210> SEQ ID NO 91
<211> LENGTH: 14
<212> TYPE: PRT
<213> ORGANISM: Artificial Sequence
<220> FEATURE:
<223> OTHER INFORMATION: FR2

<400> SEQUENCE: 91

Trp Tyr Arg Gln Ala Pro Gly Gln Gln Arg Glu Leu Val Ala
1               5                   10

<210> SEQ ID NO 92
<211> LENGTH: 14
<212> TYPE: PRT
<213> ORGANISM: Artificial Sequence
<220> FEATURE:
<223> OTHER INFORMATION: FR2

<400> SEQUENCE: 92

Trp Tyr Arg Gln Ala Pro Gly Gln Gln Arg Glu Leu Val Ala
1               5                   10

<210> SEQ ID NO 93
<211> LENGTH: 14
<212> TYPE: PRT
<213> ORGANISM: Artificial Sequence
<220> FEATURE:
<223> OTHER INFORMATION: FR2

<400> SEQUENCE: 93

Trp Tyr Arg Gln Ala Pro Gly Lys Gln Arg Glu Leu Val Ala
1               5                   10

<210> SEQ ID NO 94
<211> LENGTH: 14
<212> TYPE: PRT
<213> ORGANISM: Artificial Sequence
<220> FEATURE:
<223> OTHER INFORMATION: FR2

<400> SEQUENCE: 94

Trp Tyr Arg Gln Ala Pro Gly Lys Gln Arg Glu Leu Val Ala
1               5                   10

<210> SEQ ID NO 95
<211> LENGTH: 14
<212> TYPE: PRT
<213> ORGANISM: Artificial Sequence
<220> FEATURE:
<223> OTHER INFORMATION: FR2

<400> SEQUENCE: 95

Trp Tyr Arg Gln Arg Pro Gly Lys Gln Arg Glu Leu Val Ala
1               5                   10

<210> SEQ ID NO 96
<211> LENGTH: 14
<212> TYPE: PRT
<213> ORGANISM: Artificial Sequence
<220> FEATURE:
<223> OTHER INFORMATION: FR2

<400> SEQUENCE: 96

Trp Tyr Arg Gln Ala Pro Gly Asn Gln Arg Gly Leu Val Ala
1               5                   10

<210> SEQ ID NO 97
<211> LENGTH: 14
<212> TYPE: PRT
<213> ORGANISM: Artificial Sequence
<220> FEATURE:
<223> OTHER INFORMATION: FR2

<400> SEQUENCE: 97

Trp Tyr Arg Gln Ala Pro Gly Lys Gln Arg Glu Leu Val Ala
1               5                   10

<210> SEQ ID NO 98
<211> LENGTH: 14
<212> TYPE: PRT
<213> ORGANISM: Artificial Sequence
<220> FEATURE:
<223> OTHER INFORMATION: FR2

<400> SEQUENCE: 98

Trp Tyr Arg Gln Ala Pro Gly Lys Gln Arg Glu Leu Val Ala
1               5                   10

<210> SEQ ID NO 99
<211> LENGTH: 14
<212> TYPE: PRT
<213> ORGANISM: Artificial Sequence
<220> FEATURE:
<223> OTHER INFORMATION: FR2

<400> SEQUENCE: 99

Trp Tyr Arg Gln Ala Pro Gly Lys Gln Arg Glu Leu Val Ala
1               5                   10

<210> SEQ ID NO 100
<211> LENGTH: 14
<212> TYPE: PRT
<213> ORGANISM: Artificial Sequence
<220> FEATURE:
<223> OTHER INFORMATION: FR2

<400> SEQUENCE: 100

Trp Tyr Arg Gln Ala Pro Gly Glu Gln Arg Glu Leu Val Ala
1               5                   10

<210> SEQ ID NO 101
<211> LENGTH: 14
<212> TYPE: PRT
<213> ORGANISM: Artificial Sequence
<220> FEATURE:
<223> OTHER INFORMATION: FR2

<400> SEQUENCE: 101

Trp Tyr Arg Gln Ala Pro Gly Lys Gln Arg Glu Leu Val Ala
1               5                   10

```
<210> SEQ ID NO 102
<211> LENGTH: 14
<212> TYPE: PRT
<213> ORGANISM: Artificial Sequence
<220> FEATURE:
<223> OTHER INFORMATION: FR2

<400> SEQUENCE: 102

Trp Tyr Arg Gln Ala Pro Gly Gln Gln Arg Glu Leu Val Ala
1               5                   10

<210> SEQ ID NO 103
<211> LENGTH: 14
<212> TYPE: PRT
<213> ORGANISM: Artificial Sequence
<220> FEATURE:
<223> OTHER INFORMATION: FR2

<400> SEQUENCE: 103

Trp Tyr Arg Gln Ser Pro Gly Lys Gln Arg Glu Leu Val Ala
1               5                   10

<210> SEQ ID NO 104
<211> LENGTH: 14
<212> TYPE: PRT
<213> ORGANISM: Artificial Sequence
<220> FEATURE:
<223> OTHER INFORMATION: FR2

<400> SEQUENCE: 104

Trp Tyr Arg Gln Ala Pro Gly Lys Gln Arg Glu Leu Val Ala
1               5                   10

<210> SEQ ID NO 105
<211> LENGTH: 14
<212> TYPE: PRT
<213> ORGANISM: Artificial Sequence
<220> FEATURE:
<223> OTHER INFORMATION: FR2

<400> SEQUENCE: 105

Trp Tyr Arg Gln Ala Pro Gly Lys Gln Arg Glu Leu Val Ala
1               5                   10

<210> SEQ ID NO 106
<211> LENGTH: 14
<212> TYPE: PRT
<213> ORGANISM: Artificial Sequence
<220> FEATURE:
<223> OTHER INFORMATION: FR2

<400> SEQUENCE: 106

Trp Tyr Arg Gln Ala Pro Gly Gln Gln Arg Glu Leu Val Ala
1               5                   10

<210> SEQ ID NO 107
<211> LENGTH: 14
<212> TYPE: PRT
<213> ORGANISM: Artificial Sequence
<220> FEATURE:
<223> OTHER INFORMATION: FR2

<400> SEQUENCE: 107

Trp Tyr Arg Gln Ala Pro Gly Lys Gln Arg Glu Leu Val Ala
1               5                   10

<210> SEQ ID NO 108
```

```
<211> LENGTH: 14
<212> TYPE: PRT
<213> ORGANISM: Artificial Sequence
<220> FEATURE:
<223> OTHER INFORMATION: FR2

<400> SEQUENCE: 108

Trp Tyr Arg Gln Ala Pro Gly Lys Gln Arg Glu Leu Val Ala
1               5                   10

<210> SEQ ID NO 109
<211> LENGTH: 14
<212> TYPE: PRT
<213> ORGANISM: Artificial Sequence
<220> FEATURE:
<223> OTHER INFORMATION: FR2

<400> SEQUENCE: 109

Trp Tyr Arg Gln Ala Pro Gly Lys Gln Arg Glu Leu Val Ala
1               5                   10

<210> SEQ ID NO 110
<211> LENGTH: 14
<212> TYPE: PRT
<213> ORGANISM: Artificial Sequence
<220> FEATURE:
<223> OTHER INFORMATION: FR2

<400> SEQUENCE: 110

Trp Tyr Arg Gln Ala Pro Gly Gln Gln Arg Glu Leu Val Ala
1               5                   10

<210> SEQ ID NO 111
<211> LENGTH: 14
<212> TYPE: PRT
<213> ORGANISM: Artificial Sequence
<220> FEATURE:
<223> OTHER INFORMATION: FR2

<400> SEQUENCE: 111

Trp Tyr Arg Gln Ala Pro Gly Lys Gln Arg Glu Leu Val Ala
1               5                   10

<210> SEQ ID NO 112
<211> LENGTH: 14
<212> TYPE: PRT
<213> ORGANISM: Artificial Sequence
<220> FEATURE:
<223> OTHER INFORMATION: FR2

<400> SEQUENCE: 112

Trp Tyr Arg Gln Ala Pro Gly Lys Gln Arg Glu Leu Val Ala
1               5                   10

<210> SEQ ID NO 113
<211> LENGTH: 14
<212> TYPE: PRT
<213> ORGANISM: Artificial Sequence
<220> FEATURE:
<223> OTHER INFORMATION: FR2

<400> SEQUENCE: 113

Trp Tyr Arg Gln Ala Pro Gly Lys Gln Arg Glu Leu Val Ala
1               5                   10

<210> SEQ ID NO 114
<211> LENGTH: 14
```

```
<212> TYPE: PRT
<213> ORGANISM: Artificial Sequence
<220> FEATURE:
<223> OTHER INFORMATION: FR2

<400> SEQUENCE: 114

Trp Tyr Arg Gln Arg Pro Gly Lys Gln Arg Glu Leu Val Ala
1               5                   10

<210> SEQ ID NO 115
<211> LENGTH: 14
<212> TYPE: PRT
<213> ORGANISM: Artificial Sequence
<220> FEATURE:
<223> OTHER INFORMATION: FR2

<400> SEQUENCE: 115

Trp Tyr Arg Gln Ala Pro Gly Gln Gln Arg Glu Leu Val Ala
1               5                   10

<210> SEQ ID NO 116
<211> LENGTH: 14
<212> TYPE: PRT
<213> ORGANISM: Artificial Sequence
<220> FEATURE:
<223> OTHER INFORMATION: FR2

<400> SEQUENCE: 116

Trp Tyr Arg Gln Ala Pro Gly Gln Gln Arg Glu Leu Val Ala
1               5                   10

<210> SEQ ID NO 117
<211> LENGTH: 14
<212> TYPE: PRT
<213> ORGANISM: Artificial Sequence
<220> FEATURE:
<223> OTHER INFORMATION: FR2

<400> SEQUENCE: 117

Trp Tyr Arg Gln Ala Pro Gly Gln Gln Arg Glu Leu Val Ala
1               5                   10

<210> SEQ ID NO 118
<211> LENGTH: 14
<212> TYPE: PRT
<213> ORGANISM: Artificial Sequence
<220> FEATURE:
<223> OTHER INFORMATION: FR2

<400> SEQUENCE: 118

Trp Phe Arg Gln Pro Pro Gly Lys Glu Arg Glu Phe Val Ala
1               5                   10

<210> SEQ ID NO 119
<211> LENGTH: 14
<212> TYPE: PRT
<213> ORGANISM: Artificial Sequence
<220> FEATURE:
<223> OTHER INFORMATION: FR2

<400> SEQUENCE: 119

Trp Tyr Arg Gln Ala Pro Gly Gln Gln Arg Glu Leu Val Ala
1               5                   10

<210> SEQ ID NO 120
<211> LENGTH: 14
<212> TYPE: PRT
```

```
<213> ORGANISM: Artificial Sequence
<220> FEATURE:
<223> OTHER INFORMATION: FR2

<400> SEQUENCE: 120

Trp Tyr Arg Gln Ala Pro Gly Lys Gln Arg Glu Leu Val Ala
1               5                   10

<210> SEQ ID NO 121
<211> LENGTH: 14
<212> TYPE: PRT
<213> ORGANISM: Artificial Sequence
<220> FEATURE:
<223> OTHER INFORMATION: FR2

<400> SEQUENCE: 121

Trp Tyr Arg Gln Ala Pro Gly Gln Gln Arg Glu Leu Val Ala
1               5                   10

<210> SEQ ID NO 122
<211> LENGTH: 14
<212> TYPE: PRT
<213> ORGANISM: Artificial Sequence
<220> FEATURE:
<223> OTHER INFORMATION: FR2

<400> SEQUENCE: 122

Trp Tyr Arg Gln Ser Pro Gly Lys Gln Arg Glu Leu Val Ala
1               5                   10

<210> SEQ ID NO 123
<211> LENGTH: 14
<212> TYPE: PRT
<213> ORGANISM: Artificial Sequence
<220> FEATURE:
<223> OTHER INFORMATION: FR2

<400> SEQUENCE: 123

Trp Tyr Arg Gln Ser Pro Gly Lys Gln Arg Glu Leu Val Ala
1               5                   10

<210> SEQ ID NO 124
<211> LENGTH: 14
<212> TYPE: PRT
<213> ORGANISM: Artificial Sequence
<220> FEATURE:
<223> OTHER INFORMATION: FR2

<400> SEQUENCE: 124

Trp Tyr Arg Gln Ser Pro Gly Lys Gln Arg Glu Leu Val Ala
1               5                   10

<210> SEQ ID NO 125
<211> LENGTH: 14
<212> TYPE: PRT
<213> ORGANISM: Artificial Sequence
<220> FEATURE:
<223> OTHER INFORMATION: FR2

<400> SEQUENCE: 125

Trp Tyr Arg Gln Ser Pro Gly Lys Gln Arg Glu Leu Val Ala
1               5                   10

<210> SEQ ID NO 126
<211> LENGTH: 14
<212> TYPE: PRT
<213> ORGANISM: Artificial Sequence
```

```
<220> FEATURE:
<223> OTHER INFORMATION: FR2

<400> SEQUENCE: 126

Trp Tyr Arg Gln Ser Pro Gly Lys Gln Arg Glu Leu Val Ala
1               5                   10

<210> SEQ ID NO 127
<211> LENGTH: 14
<212> TYPE: PRT
<213> ORGANISM: Artificial Sequence
<220> FEATURE:
<223> OTHER INFORMATION: FR2

<400> SEQUENCE: 127

Trp Tyr Arg Gln Ser Pro Gly Lys Gln Arg Glu Leu Val Ala
1               5                   10

<210> SEQ ID NO 128
<211> LENGTH: 14
<212> TYPE: PRT
<213> ORGANISM: Artificial Sequence
<220> FEATURE:
<223> OTHER INFORMATION: FR2

<400> SEQUENCE: 128

Trp Tyr Arg Gln Ala Pro Gly Lys Gly Leu Glu Leu Val Ala
1               5                   10

<210> SEQ ID NO 129
<211> LENGTH: 14
<212> TYPE: PRT
<213> ORGANISM: Artificial Sequence
<220> FEATURE:
<223> OTHER INFORMATION: FR2

<400> SEQUENCE: 129

Trp Tyr Arg Gln Ala Pro Gly Lys Gly Leu Glu Leu Val Ala
1               5                   10

<210> SEQ ID NO 130
<211> LENGTH: 14
<212> TYPE: PRT
<213> ORGANISM: Artificial Sequence
<220> FEATURE:
<223> OTHER INFORMATION: FR2

<400> SEQUENCE: 130

Trp Tyr Arg Gln Ala Pro Gly Lys Gly Leu Glu Leu Val Ser
1               5                   10

<210> SEQ ID NO 131
<211> LENGTH: 14
<212> TYPE: PRT
<213> ORGANISM: Artificial Sequence
<220> FEATURE:
<223> OTHER INFORMATION: FR2

<400> SEQUENCE: 131

Trp Tyr Arg Gln Ala Pro Gly Lys Gly Leu Glu Leu Val Ser
1               5                   10

<210> SEQ ID NO 132
<211> LENGTH: 14
<212> TYPE: PRT
<213> ORGANISM: Artificial Sequence
<220> FEATURE:
```

```
<223> OTHER INFORMATION: FR2

<400> SEQUENCE: 132

Trp Tyr Arg Gln Ala Pro Gly Lys Gly Leu Glu Trp Val Ala
1               5                   10

<210> SEQ ID NO 133
<211> LENGTH: 14
<212> TYPE: PRT
<213> ORGANISM: Artificial Sequence
<220> FEATURE:
<223> OTHER INFORMATION: FR2

<400> SEQUENCE: 133

Trp Tyr Arg Gln Ala Pro Gly Lys Gly Leu Glu Leu Val Ala
1               5                   10

<210> SEQ ID NO 134
<211> LENGTH: 14
<212> TYPE: PRT
<213> ORGANISM: Artificial Sequence
<220> FEATURE:
<223> OTHER INFORMATION: FR2

<400> SEQUENCE: 134

Trp Tyr Arg Gln Ala Pro Gly Lys Gly Leu Glu Leu Val Ser
1               5                   10

<210> SEQ ID NO 135
<211> LENGTH: 14
<212> TYPE: PRT
<213> ORGANISM: Artificial Sequence
<220> FEATURE:
<223> OTHER INFORMATION: FR2

<400> SEQUENCE: 135

Trp Tyr Arg Gln Ala Pro Gly Lys Gly Leu Glu Trp Val Ser
1               5                   10

<210> SEQ ID NO 136
<211> LENGTH: 16
<212> TYPE: PRT
<213> ORGANISM: Artificial Sequence
<220> FEATURE:
<223> OTHER INFORMATION: CDR2

<400> SEQUENCE: 136

Gly Ile Thr Arg Gly Gly Ser Thr Lys Tyr Ala Asp Ser Val Lys Gly
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: CDR2

<400> SEQUENCE: 137

Gly Ile Thr Arg Gly Gly Ser Thr Lys Tyr Ala Asp Ser Val Lys Gly
1               5                   10                  15

<210> SEQ ID NO 138
<211> LENGTH: 16
<212> TYPE: PRT
<213> ORGANISM: Artificial Sequence
<220> FEATURE:
<223> OTHER INFORMATION: CDR2
```

```
<400> SEQUENCE: 138

Gly Ile Thr Arg Ser Gly Thr Thr Tyr Ala Gly Ser Val Lys Gly
1               5                   10                  15

<210> SEQ ID NO 139
<211> LENGTH: 16
<212> TYPE: PRT
<213> ORGANISM: Artificial Sequence
<220> FEATURE:
<223> OTHER INFORMATION: CDR2

<400> SEQUENCE: 139

Gly Ile Thr Arg Gly Gly Ser Thr Lys Tyr Ala Asp Ser Val Lys Gly
1               5                   10                  15

<210> SEQ ID NO 140
<211> LENGTH: 16
<212> TYPE: PRT
<213> ORGANISM: Artificial Sequence
<220> FEATURE:
<223> OTHER INFORMATION: CDR2

<400> SEQUENCE: 140

Ala Ile Thr Arg Gly Gly Asn Thr Asn Tyr Ala Asp Ser Val Lys Gly
1               5                   10                  15

<210> SEQ ID NO 141
<211> LENGTH: 16
<212> TYPE: PRT
<213> ORGANISM: Artificial Sequence
<220> FEATURE:
<223> OTHER INFORMATION: CDR2

<400> SEQUENCE: 141

Ala Glu Thr Ser Gly Gly Thr Ile Arg Tyr Ala Asp Ser Val Lys Gly
1               5                   10                  15

<210> SEQ ID NO 142
<211> LENGTH: 16
<212> TYPE: PRT
<213> ORGANISM: Artificial Sequence
<220> FEATURE:
<223> OTHER INFORMATION: CDR2

<400> SEQUENCE: 142

Gly Ile Thr Arg Gly Gly Thr Thr Lys Tyr Ala Asp Ser Val Lys Gly
1               5                   10                  15

<210> SEQ ID NO 143
<211> LENGTH: 16
<212> TYPE: PRT
<213> ORGANISM: Artificial Sequence
<220> FEATURE:
<223> OTHER INFORMATION: CDR2

<400> SEQUENCE: 143

Ala Ile Thr Arg Gly Gly Asn Thr Lys Tyr Thr Asp Ser Val Lys Gly
1               5                   10                  15

<210> SEQ ID NO 144
<211> LENGTH: 16
<212> TYPE: PRT
<213> ORGANISM: Artificial Sequence
<220> FEATURE:
<223> OTHER INFORMATION: CDR2
```

```
<400> SEQUENCE: 144

Gly Ile Thr Arg Ser Gly Ser Thr Asn Tyr Arg Asp Ser Val Lys Gly
1               5                   10                  15

<210> SEQ ID NO 145
<211> LENGTH: 16
<212> TYPE: PRT
<213> ORGANISM: Artificial Sequence
<220> FEATURE:
<223> OTHER INFORMATION: CDR2

<400> SEQUENCE: 145

Ala Glu Thr Ser Ala Gly Arg Leu Thr Tyr Ala Asp Ser Val Lys Gly
1               5                   10                  15

<210> SEQ ID NO 146
<211> LENGTH: 16
<212> TYPE: PRT
<213> ORGANISM: Artificial Sequence
<220> FEATURE:
<223> OTHER INFORMATION: CDR2

<400> SEQUENCE: 146

Gly Ile Thr Arg Gly Gly Ser Thr Lys Tyr Ala Asp Ser Val Lys Gly
1               5                   10                  15

<210> SEQ ID NO 147
<211> LENGTH: 16
<212> TYPE: PRT
<213> ORGANISM: Artificial Sequence
<220> FEATURE:
<223> OTHER INFORMATION: CDR2

<400> SEQUENCE: 147

Gly Ile Thr Arg Gly Gly Ser Thr Lys Tyr Ala Asp Ser Val Lys Gly
1               5                   10                  15

<210> SEQ ID NO 148
<211> LENGTH: 16
<212> TYPE: PRT
<213> ORGANISM: Artificial Sequence
<220> FEATURE:
<223> OTHER INFORMATION: CDR2

<400> SEQUENCE: 148

Gly Ile Thr Arg Gly Gly Ser Thr Asn Tyr Ala Asp Ser Val Lys Gly
1               5                   10                  15

<210> SEQ ID NO 149
<211> LENGTH: 16
<212> TYPE: PRT
<213> ORGANISM: Artificial Sequence
<220> FEATURE:
<223> OTHER INFORMATION: CDR2

<400> SEQUENCE: 149

Gly Ile Thr Arg Ser Gly Thr Thr Asn Tyr Ala Gly Ser Val Lys Gly
1               5                   10                  15

<210> SEQ ID NO 150
<211> LENGTH: 16
<212> TYPE: PRT
<213> ORGANISM: Artificial Sequence
<220> FEATURE:
<223> OTHER INFORMATION: CDR2

<400> SEQUENCE: 150
```

Gly Ile Thr Arg Ser Gly Ser Thr Asn Tyr Arg Asp Ser Val Lys Gly
1               5                   10                  15

<210> SEQ ID NO 151
<211> LENGTH: 16
<212> TYPE: PRT
<213> ORGANISM: Artificial Sequence
<220> FEATURE:
<223> OTHER INFORMATION: CDR2

<400> SEQUENCE: 151

Gly Ile Thr Arg Gly Gly Ser Thr Lys Tyr Ala Asp Ser Val Lys Gly
1               5                   10                  15

<210> SEQ ID NO 152
<211> LENGTH: 16
<212> TYPE: PRT
<213> ORGANISM: Artificial Sequence
<220> FEATURE:
<223> OTHER INFORMATION: CDR2

<400> SEQUENCE: 152

Gly Ile Thr Arg Ser Gly Ser Thr Asn Tyr Arg Asp Ser Val Lys Gly
1               5                   10                  15

<210> SEQ ID NO 153
<211> LENGTH: 16
<212> TYPE: PRT
<213> ORGANISM: Artificial Sequence
<220> FEATURE:
<223> OTHER INFORMATION: CDR2

<400> SEQUENCE: 153

Gly Ile Thr Ser Gly Gly Ser Thr Lys Tyr Ala Asp Ser Val Lys Gly
1               5                   10                  15

<210> SEQ ID NO 154
<211> LENGTH: 16
<212> TYPE: PRT
<213> ORGANISM: Artificial Sequence
<220> FEATURE:
<223> OTHER INFORMATION: CDR2

<400> SEQUENCE: 154

Gly Ile Thr Arg Ser Gly Thr Thr Asn Tyr Ala Gly Ser Val Lys Gly
1               5                   10                  15

<210> SEQ ID NO 155
<211> LENGTH: 16
<212> TYPE: PRT
<213> ORGANISM: Artificial Sequence
<220> FEATURE:
<223> OTHER INFORMATION: CDR2

<400> SEQUENCE: 155

Gly Ile Thr Arg Gly Gly Ser Thr Lys Tyr Ala Asp Ser Val Lys Gly
1               5                   10                  15

<210> SEQ ID NO 156
<211> LENGTH: 16
<212> TYPE: PRT
<213> ORGANISM: Artificial Sequence
<220> FEATURE:
<223> OTHER INFORMATION: CDR2

<400> SEQUENCE: 156

Gly Ile Thr Arg Gly Gly Ser Thr Lys Tyr Ala Asp Ser Val Lys Gly
1               5                   10                  15

<210> SEQ ID NO 157
<211> LENGTH: 16
<212> TYPE: PRT
<213> ORGANISM: Artificial Sequence
<220> FEATURE:
<223> OTHER INFORMATION: CDR2

<400> SEQUENCE: 157

Gly Ile Thr Arg Gly Gly Thr Thr Asn Tyr Ala Asn Ser Val Lys Gly
1               5                   10                  15

<210> SEQ ID NO 158
<211> LENGTH: 16
<212> TYPE: PRT
<213> ORGANISM: Artificial Sequence
<220> FEATURE:
<223> OTHER INFORMATION: CDR2

<400> SEQUENCE: 158

Gly Ile Thr Arg Ser Gly Thr Thr Thr Tyr Ala Gly Ser Val Lys Gly
1               5                   10                  15

<210> SEQ ID NO 159
<211> LENGTH: 16
<212> TYPE: PRT
<213> ORGANISM: Artificial Sequence
<220> FEATURE:
<223> OTHER INFORMATION: CDR2

<400> SEQUENCE: 159

Ala Ile Thr Arg Gly Gly Asn Thr Asn Tyr Ala Asp Ser Val Lys Gly
1               5                   10                  15

<210> SEQ ID NO 160
<211> LENGTH: 16
<212> TYPE: PRT
<213> ORGANISM: Artificial Sequence
<220> FEATURE:
<223> OTHER INFORMATION: CDR2

<400> SEQUENCE: 160

Gly Ile Thr Arg Gly Gly Ser Thr His Tyr Ala Asp Ser Val Lys Gly
1               5                   10                  15

<210> SEQ ID NO 161
<211> LENGTH: 16
<212> TYPE: PRT
<213> ORGANISM: Artificial Sequence
<220> FEATURE:
<223> OTHER INFORMATION: CDR2

<400> SEQUENCE: 161

Gly Ile Thr Arg Gly Gly Ser Thr Asn Tyr Ala Asp Ser Val Lys Gly
1               5                   10                  15

<210> SEQ ID NO 162
<211> LENGTH: 16
<212> TYPE: PRT
<213> ORGANISM: Artificial Sequence
<220> FEATURE:
<223> OTHER INFORMATION: CDR2

<400> SEQUENCE: 162

Gly Ile Thr Arg Ser Gly Ser Thr Lys Tyr Ala Asp Ser Val Lys Gly

<210> SEQ ID NO 163
<211> LENGTH: 17
<212> TYPE: PRT
<213> ORGANISM: Artificial Sequence
<220> FEATURE:
<223> OTHER INFORMATION: CDR2

<400> SEQUENCE: 163

Val Ile His Trp Ser Gly Ala Ser Thr Tyr Tyr Thr Asp Ser Val Lys
1               5                   10                  15
Gly

<210> SEQ ID NO 164
<211> LENGTH: 16
<212> TYPE: PRT
<213> ORGANISM: Artificial Sequence
<220> FEATURE:
<223> OTHER INFORMATION: CDR2

<400> SEQUENCE: 164

Gly Ile Thr Arg Gly Gly Ser Thr Lys Tyr Ala Asp Ser Val Lys Gly
1               5                   10                  15

<210> SEQ ID NO 165
<211> LENGTH: 16
<212> TYPE: PRT
<213> ORGANISM: Artificial Sequence
<220> FEATURE:
<223> OTHER INFORMATION: CDR2

<400> SEQUENCE: 165

Gly Ile Thr Arg Ser Gly Thr Thr Thr Tyr Ala Gly Ser Val Lys Gly
1               5                   10                  15

<210> SEQ ID NO 166
<211> LENGTH: 16
<212> TYPE: PRT
<213> ORGANISM: Artificial Sequence
<220> FEATURE:
<223> OTHER INFORMATION: CDR2

<400> SEQUENCE: 166

Gly Ile Thr Arg Gly Gly Ser Thr Lys Tyr Ala Asp Ser Val Lys Gly
1               5                   10                  15

<210> SEQ ID NO 167
<211> LENGTH: 16
<212> TYPE: PRT
<213> ORGANISM: Artificial Sequence
<220> FEATURE:
<223> OTHER INFORMATION: CDR2

<400> SEQUENCE: 167

Gly Ile Thr Arg Gly Gly Ser Thr Asn Tyr Ala Asp Ser Val Lys Gly
1               5                   10                  15

<210> SEQ ID NO 168
<211> LENGTH: 16
<212> TYPE: PRT
<213> ORGANISM: Artificial Sequence
<220> FEATURE:
<223> OTHER INFORMATION: CDR2

<400> SEQUENCE: 168

```
Gly Ile Thr Arg Gly Gly Ser Thr Asn Tyr Ala Asp Ser Val Lys Gly
1               5                   10                  15
```

<210> SEQ ID NO 169
<211> LENGTH: 16
<212> TYPE: PRT
<213> ORGANISM: Artificial Sequence
<220> FEATURE:
<223> OTHER INFORMATION: CDR2

<400> SEQUENCE: 169

```
Gly Ile Thr Arg Gly Gly Ser Thr Asn Tyr Ala Asp Ser Val Lys Gly
1               5                   10                  15
```

<210> SEQ ID NO 170
<211> LENGTH: 16
<212> TYPE: PRT
<213> ORGANISM: Artificial Sequence
<220> FEATURE:
<223> OTHER INFORMATION: CDR2

<400> SEQUENCE: 170

```
Gly Ile Thr Arg Gly Gly Ser Thr Asn Tyr Ala Asp Ser Val Lys Gly
1               5                   10                  15
```

<210> SEQ ID NO 171
<211> LENGTH: 16
<212> TYPE: PRT
<213> ORGANISM: Artificial Sequence
<220> FEATURE:
<223> OTHER INFORMATION: CDR2

<400> SEQUENCE: 171

```
Gly Ile Thr Arg Gly Gly Ser Thr Asn Tyr Ala Asp Ser Val Lys Gly
1               5                   10                  15
```

<210> SEQ ID NO 172
<211> LENGTH: 16
<212> TYPE: PRT
<213> ORGANISM: Artificial Sequence
<220> FEATURE:
<223> OTHER INFORMATION: CDR2

<400> SEQUENCE: 172

```
Gly Ile Thr Arg Gly Gly Ser Thr Asn Tyr Ala Asp Ser Val Lys Gly
1               5                   10                  15
```

<210> SEQ ID NO 173
<211> LENGTH: 16
<212> TYPE: PRT
<213> ORGANISM: Artificial Sequence
<220> FEATURE:
<223> OTHER INFORMATION: CDR2

<400> SEQUENCE: 173

```
Gly Ile Thr Arg Gly Gly Ser Thr Lys Tyr Ala Asp Ser Val Lys Gly
1               5                   10                  15
```

<210> SEQ ID NO 174
<211> LENGTH: 16
<212> TYPE: PRT
<213> ORGANISM: Artificial Sequence
<220> FEATURE:
<223> OTHER INFORMATION: CDR2

<400> SEQUENCE: 174

```
Gly Ile Thr Arg Ser Gly Ser Thr Asn Tyr Arg Asp Ser Val Lys Gly
1               5                   10                  15
```

<210> SEQ ID NO 175
<211> LENGTH: 16
<212> TYPE: PRT
<213> ORGANISM: Artificial Sequence
<220> FEATURE:
<223> OTHER INFORMATION: CDR2

<400> SEQUENCE: 175

Gly Ile Thr Arg Gly Gly Ser Thr Lys Tyr Ala Asp Ser Val Lys Gly
1               5                   10                  15

<210> SEQ ID NO 176
<211> LENGTH: 16
<212> TYPE: PRT
<213> ORGANISM: Artificial Sequence
<220> FEATURE:
<223> OTHER INFORMATION: CDR2

<400> SEQUENCE: 176

Gly Ile Thr Arg Ser Gly Ser Thr Asn Tyr Arg Asp Ser Val Lys Gly
1               5                   10                  15

<210> SEQ ID NO 177
<211> LENGTH: 16
<212> TYPE: PRT
<213> ORGANISM: Artificial Sequence
<220> FEATURE:
<223> OTHER INFORMATION: CDR2

<400> SEQUENCE: 177

Gly Ile Thr Arg Ser Gly Ser Thr Asn Tyr Arg Asp Ser Val Lys Gly
1               5                   10                  15

<210> SEQ ID NO 178
<211> LENGTH: 16
<212> TYPE: PRT
<213> ORGANISM: Artificial Sequence
<220> FEATURE:
<223> OTHER INFORMATION: CDR2

<400> SEQUENCE: 178

Gly Ile Thr Arg Ser Gly Ser Thr Asn Tyr Arg Asp Ser Val Lys Gly
1               5                   10                  15

<210> SEQ ID NO 179
<211> LENGTH: 16
<212> TYPE: PRT
<213> ORGANISM: Artificial Sequence
<220> FEATURE:
<223> OTHER INFORMATION: CDR2

<400> SEQUENCE: 179

Gly Ile Thr Arg Ser Gly Ser Thr Asn Tyr Arg Asp Ser Val Lys Gly
1               5                   10                  15

<210> SEQ ID NO 180
<211> LENGTH: 16
<212> TYPE: PRT
<213> ORGANISM: Artificial Sequence
<220> FEATURE:
<223> OTHER INFORMATION: CDR2

<400> SEQUENCE: 180

Gly Ile Thr Arg Ser Gly Ser Thr Asn Tyr Arg Asp Ser Val Lys Gly
1               5                   10                  15

<210> SEQ ID NO 181
<211> LENGTH: 32
<212> TYPE: PRT
<213> ORGANISM: Artificial Sequence
<220> FEATURE:
<223> OTHER INFORMATION: FR3

<400> SEQUENCE: 181

Arg Phe Thr Ile Ser Arg Asp Asn Ala Lys Asn Thr Leu Tyr Leu Gln
1               5                   10                  15

Met Asn Ser Leu Lys Pro Asp Asp Thr Ala Val Tyr Tyr Cys Thr Asp
            20                  25                  30

<210> SEQ ID NO 182
<211> LENGTH: 32
<212> TYPE: PRT
<213> ORGANISM: Artificial Sequence
<220> FEATURE:
<223> OTHER INFORMATION: FR3

<400> SEQUENCE: 182

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Thr Asp
            20                  25                  30

<210> SEQ ID NO 183
<211> LENGTH: 32
<212> TYPE: PRT
<213> ORGANISM: Artificial Sequence
<220> FEATURE:
<223> OTHER INFORMATION: FR3

<400> SEQUENCE: 183

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Thr Asp
            20                  25                  30

<210> SEQ ID NO 184
<211> LENGTH: 32
<212> TYPE: PRT
<213> ORGANISM: Artificial Sequence
<220> FEATURE:
<223> OTHER INFORMATION: FR3

<400> SEQUENCE: 184

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Thr Asp
            20                  25                  30

<210> SEQ ID NO 185
<211> LENGTH: 32
<212> TYPE: PRT
<213> ORGANISM: Artificial Sequence
<220> FEATURE:
<223> OTHER INFORMATION: FR3

<400> SEQUENCE: 185

Arg Phe Ser Ile Ser Arg Asp Asn Ala Lys Asn Thr Met Tyr Leu Gln
1               5                   10                  15

Met Asn Ser Leu Lys Pro Glu Asp Thr Ala Val Tyr Tyr Cys Thr Asp

-continued

```
                 20                  25                  30

<210> SEQ ID NO 186
<211> LENGTH: 32
<212> TYPE: PRT
<213> ORGANISM: Artificial Sequence
<220> FEATURE:
<223> OTHER INFORMATION: FR3

<400> SEQUENCE: 186

Arg Phe Thr Ile Ser Arg Asp Asn Ala Lys Asn Thr Met Tyr Leu Gln
1               5                   10                  15

Met Asn Ser Leu Lys Pro Glu Asp Thr Ala Val Tyr Tyr Cys Ala Ala
                20                  25                  30

<210> SEQ ID NO 187
<211> LENGTH: 32
<212> TYPE: PRT
<213> ORGANISM: Artificial Sequence
<220> FEATURE:
<223> OTHER INFORMATION: FR3

<400> SEQUENCE: 187

Arg Phe Thr Ile Ser Arg Asp Asn Ala Glu Asn Thr Val Tyr Leu Gln
1               5                   10                  15

Met Asn Ser Leu Lys Pro Glu Asp Thr Ala Val Tyr Tyr Cys Thr Asp
                20                  25                  30

<210> SEQ ID NO 188
<211> LENGTH: 32
<212> TYPE: PRT
<213> ORGANISM: Artificial Sequence
<220> FEATURE:
<223> OTHER INFORMATION: FR3

<400> SEQUENCE: 188

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Thr Asp
                20                  25                  30

<210> SEQ ID NO 189
<211> LENGTH: 32
<212> TYPE: PRT
<213> ORGANISM: Artificial Sequence
<220> FEATURE:
<223> OTHER INFORMATION: FR3

<400> SEQUENCE: 189

Arg Phe Thr Ile Ser Arg Asp Asn Ala Lys Asn Thr Met Tyr Leu Gln
1               5                   10                  15

Met Asn Ser Leu Lys Pro Glu Asp Thr Ala Val Tyr Tyr Cys Thr Asp
                20                  25                  30

<210> SEQ ID NO 190
<211> LENGTH: 32
<212> TYPE: PRT
<213> ORGANISM: Artificial Sequence
<220> FEATURE:
<223> OTHER INFORMATION: FR3

<400> SEQUENCE: 190

Arg Phe Thr Val Ser Arg Asp Asn Ala Lys Asp Thr Ile Asp Leu Gln
1               5                   10                  15
```

Met Asn Ser Leu Lys Pro Glu Asp Thr Gly Val Tyr Tyr Cys Ala Ala
            20                  25                  30

<210> SEQ ID NO 191
<211> LENGTH: 32
<212> TYPE: PRT
<213> ORGANISM: Artificial Sequence
<220> FEATURE:
<223> OTHER INFORMATION: FR3

<400> SEQUENCE: 191

Arg Phe Thr Ile Ser Arg Asp Asn Ala Lys Asn Thr Val Tyr Leu Gln
1               5                   10                  15

Met His Ser Leu Lys Pro Glu Asp Thr Ala Val Tyr Tyr Cys Thr Asp
            20                  25                  30

<210> SEQ ID NO 192
<211> LENGTH: 32
<212> TYPE: PRT
<213> ORGANISM: Artificial Sequence
<220> FEATURE:
<223> OTHER INFORMATION: FR3

<400> SEQUENCE: 192

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Thr Asp
            20                  25                  30

<210> SEQ ID NO 193
<211> LENGTH: 32
<212> TYPE: PRT
<213> ORGANISM: Artificial Sequence
<220> FEATURE:
<223> OTHER INFORMATION: FR3

<400> SEQUENCE: 193

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Thr Asp
            20                  25                  30

<210> SEQ ID NO 194
<211> LENGTH: 32
<212> TYPE: PRT
<213> ORGANISM: Artificial Sequence
<220> FEATURE:
<223> OTHER INFORMATION: FR3

<400> SEQUENCE: 194

Arg Phe Thr Ile Ser Arg Asp Asn Ala Lys Asn Thr Val Tyr Leu Gln
1               5                   10                  15

Met Asn Gly Leu Lys Pro Glu Asp Thr Ala Val Tyr Tyr Cys Thr Asp
            20                  25                  30

<210> SEQ ID NO 195
<211> LENGTH: 32
<212> TYPE: PRT
<213> ORGANISM: Artificial Sequence
<220> FEATURE:
<223> OTHER INFORMATION: FR3

<400> SEQUENCE: 195

Arg Phe Thr Ile Ser Arg Asp Asn Ala Lys Asn Thr Met Tyr Leu Gln
1               5                   10                  15

Met Asn Ser Leu Lys Pro Glu Asp Thr Ala Val Tyr Tyr Cys Thr Asp
            20                  25                  30

<210> SEQ ID NO 196
<211> LENGTH: 32
<212> TYPE: PRT
<213> ORGANISM: Artificial Sequence
<220> FEATURE:
<223> OTHER INFORMATION: FR3

<400> SEQUENCE: 196

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Thr Asp
            20                  25                  30

<210> SEQ ID NO 197
<211> LENGTH: 32
<212> TYPE: PRT
<213> ORGANISM: Artificial Sequence
<220> FEATURE:
<223> OTHER INFORMATION: FR3

<400> SEQUENCE: 197

Arg Phe Thr Ile Ser Arg Asp Asn Ala Lys Asn Thr Met Tyr Leu Gln
1               5                   10                  15

Met Asn Ser Leu Lys Pro Glu Asp Thr Ala Val Tyr Tyr Cys Thr Asp
            20                  25                  30

<210> SEQ ID NO 198
<211> LENGTH: 32
<212> TYPE: PRT
<213> ORGANISM: Artificial Sequence
<220> FEATURE:
<223> OTHER INFORMATION: FR3

<400> SEQUENCE: 198

Arg Phe Thr Ile Ser Arg Asp Asn Ala Lys Asn Thr Val Tyr Leu Gln
1               5                   10                  15

Met Asn Asn Leu Lys Pro Glu Asp Thr Ala Ile Tyr Tyr Cys Thr Asp
            20                  25                  30

<210> SEQ ID NO 199
<211> LENGTH: 32
<212> TYPE: PRT
<213> ORGANISM: Artificial Sequence
<220> FEATURE:
<223> OTHER INFORMATION: FR3

<400> SEQUENCE: 199

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Thr Asp
            20                  25                  30

<210> SEQ ID NO 200
<211> LENGTH: 32
<212> TYPE: PRT
<213> ORGANISM: Artificial Sequence
<220> FEATURE:
<223> OTHER INFORMATION: FR3

<400> SEQUENCE: 200

Arg Phe Thr Ile Ser Arg Asp Asn Ala Lys Asn Thr Leu Tyr Leu Gln

```
1               5                   10                  15
Met Asn Ser Leu Lys Pro Glu Asp Thr Ala Val Tyr Tyr Cys Thr Asp
            20                  25                  30
```

<210> SEQ ID NO 201
<211> LENGTH: 32
<212> TYPE: PRT
<213> ORGANISM: Artificial Sequence
<220> FEATURE:
<223> OTHER INFORMATION: FR3

<400> SEQUENCE: 201

```
Arg Phe Thr Ile Ser Arg Asp Asn Ala Lys Asn Thr Leu Tyr Leu Gln
1               5                   10                  15
Met Asn Ser Leu Lys Pro Glu Asp Thr Ala Val Tyr Tyr Cys Thr Asp
            20                  25                  30
```

<210> SEQ ID NO 202
<211> LENGTH: 32
<212> TYPE: PRT
<213> ORGANISM: Artificial Sequence
<220> FEATURE:
<223> OTHER INFORMATION: FR3

<400> SEQUENCE: 202

```
Arg Phe Thr Ile Ser Arg Asp Asn Ala Lys Asn Thr Val Tyr Leu Gln
1               5                   10                  15
Met Asn Ser Leu Lys Pro Glu Asp Thr Ala Val Tyr Tyr Cys Thr Asp
            20                  25                  30
```

<210> SEQ ID NO 203
<211> LENGTH: 32
<212> TYPE: PRT
<213> ORGANISM: Artificial Sequence
<220> FEATURE:
<223> OTHER INFORMATION: FR3

<400> SEQUENCE: 203

```
Arg Phe Thr Ile Ser Arg Asp Asn Ala Lys Asn Thr Val Tyr Leu Gln
1               5                   10                  15
Met Asn Ser Leu Lys Pro Glu Asp Thr Ala Val Tyr Tyr Cys Thr Asp
            20                  25                  30
```

<210> SEQ ID NO 204
<211> LENGTH: 32
<212> TYPE: PRT
<213> ORGANISM: Artificial Sequence
<220> FEATURE:
<223> OTHER INFORMATION: FR3

<400> SEQUENCE: 204

```
Arg Phe Ser Ile Ser Arg Asp Asn Ala Lys Asn Thr Met Tyr Leu Gln
1               5                   10                  15
Met Asn Ser Leu Lys Pro Glu Asp Thr Ala Val Tyr Tyr Cys Thr Asp
            20                  25                  30
```

<210> SEQ ID NO 205
<211> LENGTH: 32
<212> TYPE: PRT
<213> ORGANISM: Artificial Sequence
<220> FEATURE:
<223> OTHER INFORMATION: FR3

<400> SEQUENCE: 205

-continued

```
Arg Phe Thr Ile Ser Arg Asp Asn Ala Lys Asn Thr Leu Tyr Leu Gln
1               5                   10                  15

Met Asn Ser Leu Glu Pro Glu Asp Thr Ala Val Tyr Tyr Cys Thr Asp
            20                  25                  30
```

<210> SEQ ID NO 206
<211> LENGTH: 32
<212> TYPE: PRT
<213> ORGANISM: Artificial Sequence
<220> FEATURE:
<223> OTHER INFORMATION: FR3

<400> SEQUENCE: 206

```
Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Thr Asp
            20                  25                  30
```

<210> SEQ ID NO 207
<211> LENGTH: 32
<212> TYPE: PRT
<213> ORGANISM: Artificial Sequence
<220> FEATURE:
<223> OTHER INFORMATION: FR3

<400> SEQUENCE: 207

```
Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Thr Asp
            20                  25                  30
```

<210> SEQ ID NO 208
<211> LENGTH: 32
<212> TYPE: PRT
<213> ORGANISM: Artificial Sequence
<220> FEATURE:
<223> OTHER INFORMATION: FR3

<400> SEQUENCE: 208

```
Arg Phe Thr Ile Ser Arg Asp Asn Ala Lys Asn Thr Val Tyr Leu Gln
1               5                   10                  15

Met Asn Ser Leu Lys Pro Glu Asp Thr Ala Ile Tyr Tyr Cys Ala Ala
            20                  25                  30
```

<210> SEQ ID NO 209
<211> LENGTH: 32
<212> TYPE: PRT
<213> ORGANISM: Artificial Sequence
<220> FEATURE:
<223> OTHER INFORMATION: FR3

<400> SEQUENCE: 209

```
Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Thr Asp
            20                  25                  30
```

<210> SEQ ID NO 210
<211> LENGTH: 32
<212> TYPE: PRT
<213> ORGANISM: Artificial Sequence
<220> FEATURE:
<223> OTHER INFORMATION: FR3

<400> SEQUENCE: 210

Arg Phe Thr Ile Ser Arg Asp Asn Ala Lys Asn Thr Val Tyr Leu Gln
1               5                   10                  15

Met Asn Gly Leu Lys Pro Glu Asp Thr Ala Val Tyr Tyr Cys Thr Asp
            20                  25                  30

<210> SEQ ID NO 211
<211> LENGTH: 32
<212> TYPE: PRT
<213> ORGANISM: Artificial Sequence
<220> FEATURE:
<223> OTHER INFORMATION: FR3

<400> SEQUENCE: 211

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Thr Asp
            20                  25                  30

<210> SEQ ID NO 212
<211> LENGTH: 32
<212> TYPE: PRT
<213> ORGANISM: Artificial Sequence
<220> FEATURE:
<223> OTHER INFORMATION: FR3

<400> SEQUENCE: 212

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Thr Asp
            20                  25                  30

<210> SEQ ID NO 213
<211> LENGTH: 32
<212> TYPE: PRT
<213> ORGANISM: Artificial Sequence
<220> FEATURE:
<223> OTHER INFORMATION: FR3

<400> SEQUENCE: 213

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Thr Asp
            20                  25                  30

<210> SEQ ID NO 214
<211> LENGTH: 32
<212> TYPE: PRT
<213> ORGANISM: Artificial Sequence
<220> FEATURE:
<223> OTHER INFORMATION: FR3

<400> SEQUENCE: 214

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Thr Asp
            20                  25                  30

<210> SEQ ID NO 215
<211> LENGTH: 32
<212> TYPE: PRT
<213> ORGANISM: Artificial Sequence
<220> FEATURE:
<223> OTHER INFORMATION: FR3

```
<400> SEQUENCE: 215

Arg Phe Ala Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Thr Asp
                20                  25                  30

<210> SEQ ID NO 216
<211> LENGTH: 32
<212> TYPE: PRT
<213> ORGANISM: Artificial Sequence
<220> FEATURE:
<223> OTHER INFORMATION: FR3

<400> SEQUENCE: 216

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Thr Asp
                20                  25                  30

<210> SEQ ID NO 217
<211> LENGTH: 32
<212> TYPE: PRT
<213> ORGANISM: Artificial Sequence
<220> FEATURE:
<223> OTHER INFORMATION: FR3

<400> SEQUENCE: 217

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Thr Asp
                20                  25                  30

<210> SEQ ID NO 218
<211> LENGTH: 32
<212> TYPE: PRT
<213> ORGANISM: Artificial Sequence
<220> FEATURE:
<223> OTHER INFORMATION: FR3

<400> SEQUENCE: 218

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Thr Asp
                20                  25                  30

<210> SEQ ID NO 219
<211> LENGTH: 32
<212> TYPE: PRT
<213> ORGANISM: Artificial Sequence
<220> FEATURE:
<223> OTHER INFORMATION: FR3

<400> SEQUENCE: 219

Arg Phe Thr Ile Ser Arg Asp Asn Ser Lys Asn Thr Met Tyr Leu Gln
1               5                   10                  15

Met Asn Ser Leu Arg Ala Glu Asp Thr Ala Val Tyr Tyr Cys Thr Asp
                20                  25                  30

<210> SEQ ID NO 220
<211> LENGTH: 32
<212> TYPE: PRT
<213> ORGANISM: Artificial Sequence
<220> FEATURE:
<223> OTHER INFORMATION: FR3
```

<400> SEQUENCE: 220

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Thr Asp
            20                  25                  30

<210> SEQ ID NO 221
<211> LENGTH: 32
<212> TYPE: PRT
<213> ORGANISM: Artificial Sequence
<220> FEATURE:
<223> OTHER INFORMATION: FR3

<400> SEQUENCE: 221

Arg Phe Thr Ile Ser Arg Asp Asn Ser Lys Asn Thr Met Tyr Leu Gln
1               5                   10                  15

Met Asn Ser Leu Arg Ala Glu Asp Thr Ala Val Tyr Tyr Cys Thr Asp
            20                  25                  30

<210> SEQ ID NO 222
<211> LENGTH: 32
<212> TYPE: PRT
<213> ORGANISM: Artificial Sequence
<220> FEATURE:
<223> OTHER INFORMATION: FR3

<400> SEQUENCE: 222

Arg Phe Thr Ile Ser Arg Asp Asn Ser Lys Asn Thr Met Tyr Leu Gln
1               5                   10                  15

Met Asn Ser Leu Arg Ala Glu Asp Thr Ala Val Tyr Tyr Cys Thr Asp
            20                  25                  30

<210> SEQ ID NO 223
<211> LENGTH: 32
<212> TYPE: PRT
<213> ORGANISM: Artificial Sequence
<220> FEATURE:
<223> OTHER INFORMATION: FR3

<400> SEQUENCE: 223

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Thr Asp
            20                  25                  30

<210> SEQ ID NO 224
<211> LENGTH: 32
<212> TYPE: PRT
<213> ORGANISM: Artificial Sequence
<220> FEATURE:
<223> OTHER INFORMATION: FR3

<400> SEQUENCE: 224

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Thr Asp
            20                  25                  30

<210> SEQ ID NO 225
<211> LENGTH: 32
<212> TYPE: PRT
<213> ORGANISM: Artificial Sequence
<220> FEATURE:

<223> OTHER INFORMATION: FR3

<400> SEQUENCE: 225

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Thr Asp
            20                  25                  30

<210> SEQ ID NO 226
<211> LENGTH: 9
<212> TYPE: PRT
<213> ORGANISM: Artificial Sequence
<220> FEATURE:
<223> OTHER INFORMATION: CDR3

<400> SEQUENCE: 226

Tyr Ser Arg Lys Tyr Tyr Gln Asp Tyr
1               5

<210> SEQ ID NO 227
<211> LENGTH: 9
<212> TYPE: PRT
<213> ORGANISM: Artificial Sequence
<220> FEATURE:
<223> OTHER INFORMATION: CDR3

<400> SEQUENCE: 227

Tyr Ser Arg Gly Tyr Tyr Gln Asp Tyr
1               5

<210> SEQ ID NO 228
<211> LENGTH: 9
<212> TYPE: PRT
<213> ORGANISM: Artificial Sequence
<220> FEATURE:
<223> OTHER INFORMATION: CDR3

<400> SEQUENCE: 228

Tyr Ser Ser Ser Tyr Tyr Gln Asp Tyr
1               5

<210> SEQ ID NO 229
<211> LENGTH: 9
<212> TYPE: PRT
<213> ORGANISM: Artificial Sequence
<220> FEATURE:
<223> OTHER INFORMATION: CDR3

<400> SEQUENCE: 229

Tyr Ser Arg Ser Tyr Tyr Gln Asp Tyr
1               5

<210> SEQ ID NO 230
<211> LENGTH: 9
<212> TYPE: PRT
<213> ORGANISM: Artificial Sequence
<220> FEATURE:
<223> OTHER INFORMATION: CDR3

<400> SEQUENCE: 230

Tyr Ser Arg Arg Tyr Tyr Gln Asp Asp
1               5

<210> SEQ ID NO 231
<211> LENGTH: 6
<212> TYPE: PRT

```
<213> ORGANISM: Artificial Sequence
<220> FEATURE:
<223> OTHER INFORMATION: CDR3

<400> SEQUENCE: 231

Arg Asp Leu Asp Asp Tyr
1               5

<210> SEQ ID NO 232
<211> LENGTH: 9
<212> TYPE: PRT
<213> ORGANISM: Artificial Sequence
<220> FEATURE:
<223> OTHER INFORMATION: CDR3

<400> SEQUENCE: 232

Tyr Ser Arg Ser Tyr Tyr Glu Asp His
1               5

<210> SEQ ID NO 233
<211> LENGTH: 9
<212> TYPE: PRT
<213> ORGANISM: Artificial Sequence
<220> FEATURE:
<223> OTHER INFORMATION: CDR3

<400> SEQUENCE: 233

Tyr Ser Arg Ser Tyr Tyr Gln Asp Tyr
1               5

<210> SEQ ID NO 234
<211> LENGTH: 9
<212> TYPE: PRT
<213> ORGANISM: Artificial Sequence
<220> FEATURE:
<223> OTHER INFORMATION: CDR3

<400> SEQUENCE: 234

Tyr Ser Ser Arg Tyr Tyr His Asp Tyr
1               5

<210> SEQ ID NO 235
<211> LENGTH: 6
<212> TYPE: PRT
<213> ORGANISM: Artificial Sequence
<220> FEATURE:
<223> OTHER INFORMATION: CDR3

<400> SEQUENCE: 235

Arg Gly Leu Ala Asp Tyr
1               5

<210> SEQ ID NO 236
<211> LENGTH: 9
<212> TYPE: PRT
<213> ORGANISM: Artificial Sequence
<220> FEATURE:
<223> OTHER INFORMATION: CDR3

<400> SEQUENCE: 236

Tyr Ser Arg Thr Tyr Tyr Glu Asp His
1               5

<210> SEQ ID NO 237
<211> LENGTH: 9
<212> TYPE: PRT
<213> ORGANISM: Artificial Sequence
```

<220> FEATURE:
<223> OTHER INFORMATION: CDR3

<400> SEQUENCE: 237

Tyr Ser Arg Gly Tyr Tyr Gln Asp Tyr
1               5

<210> SEQ ID NO 238
<211> LENGTH: 9
<212> TYPE: PRT
<213> ORGANISM: Artificial Sequence
<220> FEATURE:
<223> OTHER INFORMATION: CDR3

<400> SEQUENCE: 238

Tyr Ser Leu Gly Tyr Tyr Gln Asp Tyr
1               5

<210> SEQ ID NO 239
<211> LENGTH: 9
<212> TYPE: PRT
<213> ORGANISM: Artificial Sequence
<220> FEATURE:
<223> OTHER INFORMATION: CDR3

<400> SEQUENCE: 239

Tyr Ser Arg Arg Tyr Tyr Gln Asp Asp
1               5

<210> SEQ ID NO 240
<211> LENGTH: 9
<212> TYPE: PRT
<213> ORGANISM: Artificial Sequence
<220> FEATURE:
<223> OTHER INFORMATION: CDR3

<400> SEQUENCE: 240

Tyr Ser Ser Arg Tyr Tyr His Asp Tyr
1               5

<210> SEQ ID NO 241
<211> LENGTH: 9
<212> TYPE: PRT
<213> ORGANISM: Artificial Sequence
<220> FEATURE:
<223> OTHER INFORMATION: CDR3

<400> SEQUENCE: 241

Tyr Ser Arg Gly Tyr Tyr Gln Asp Tyr
1               5

<210> SEQ ID NO 242
<211> LENGTH: 9
<212> TYPE: PRT
<213> ORGANISM: Artificial Sequence
<220> FEATURE:
<223> OTHER INFORMATION: CDR3

<400> SEQUENCE: 242

Tyr Ser Ser Arg Tyr Tyr His Asp Tyr
1               5

<210> SEQ ID NO 243
<211> LENGTH: 9
<212> TYPE: PRT
<213> ORGANISM: Artificial Sequence
<220> FEATURE:

<223> OTHER INFORMATION: CDR3

<400> SEQUENCE: 243

Tyr Ser Lys Arg Tyr Tyr Gln Asp Tyr
1               5

<210> SEQ ID NO 244
<211> LENGTH: 9
<212> TYPE: PRT
<213> ORGANISM: Artificial Sequence
<220> FEATURE:
<223> OTHER INFORMATION: CDR3

<400> SEQUENCE: 244

Tyr Ser Arg Lys Tyr Tyr Glu Asp Gln
1               5

<210> SEQ ID NO 245
<211> LENGTH: 9
<212> TYPE: PRT
<213> ORGANISM: Artificial Sequence
<220> FEATURE:
<223> OTHER INFORMATION: CDR3

<400> SEQUENCE: 245

Tyr Ser Arg Gly Tyr Tyr Gln Asp Tyr
1               5

<210> SEQ ID NO 246
<211> LENGTH: 9
<212> TYPE: PRT
<213> ORGANISM: Artificial Sequence
<220> FEATURE:
<223> OTHER INFORMATION: CDR3

<400> SEQUENCE: 246

Tyr Ser Arg Ser Tyr Tyr Gln Asp Tyr
1               5

<210> SEQ ID NO 247
<211> LENGTH: 9
<212> TYPE: PRT
<213> ORGANISM: Artificial Sequence
<220> FEATURE:
<223> OTHER INFORMATION: CDR3

<400> SEQUENCE: 247

Tyr Ser Ser Arg Tyr Tyr His Asp Tyr
1               5

<210> SEQ ID NO 248
<211> LENGTH: 9
<212> TYPE: PRT
<213> ORGANISM: Artificial Sequence
<220> FEATURE:
<223> OTHER INFORMATION: CDR3

<400> SEQUENCE: 248

Tyr Ser Ser Ser Tyr Tyr Gln Asp Tyr
1               5

<210> SEQ ID NO 249
<211> LENGTH: 9
<212> TYPE: PRT
<213> ORGANISM: Artificial Sequence
<220> FEATURE:
<223> OTHER INFORMATION: CDR3

<400> SEQUENCE: 249

Tyr Ser Arg Arg Tyr Tyr Gln Asp Asp
1               5

<210> SEQ ID NO 250
<211> LENGTH: 9
<212> TYPE: PRT
<213> ORGANISM: Artificial Sequence
<220> FEATURE:
<223> OTHER INFORMATION: CDR3

<400> SEQUENCE: 250

Tyr Ser Arg Arg Tyr Tyr Glu Asp Tyr
1               5

<210> SEQ ID NO 251
<211> LENGTH: 9
<212> TYPE: PRT
<213> ORGANISM: Artificial Sequence
<220> FEATURE:
<223> OTHER INFORMATION: CDR3

<400> SEQUENCE: 251

Tyr Ser Arg Gly Tyr Tyr Gln Asp Tyr
1               5

<210> SEQ ID NO 252
<211> LENGTH: 9
<212> TYPE: PRT
<213> ORGANISM: Artificial Sequence
<220> FEATURE:
<223> OTHER INFORMATION: CDR3

<400> SEQUENCE: 252

Tyr Ser Arg Gly Tyr Tyr Gln Asp Tyr
1               5

<210> SEQ ID NO 253
<211> LENGTH: 14
<212> TYPE: PRT
<213> ORGANISM: Artificial Sequence
<220> FEATURE:
<223> OTHER INFORMATION: CDR3

<400> SEQUENCE: 253

Glu Val Pro Val Ser Thr Trp Pro Pro Thr Glu Tyr Ser Trp
1               5                   10

<210> SEQ ID NO 254
<211> LENGTH: 9
<212> TYPE: PRT
<213> ORGANISM: Artificial Sequence
<220> FEATURE:
<223> OTHER INFORMATION: CDR3

<400> SEQUENCE: 254

Phe Ser Arg Asp Tyr Tyr Gln Asp Tyr
1               5

<210> SEQ ID NO 255
<211> LENGTH: 9
<212> TYPE: PRT
<213> ORGANISM: Artificial Sequence
<220> FEATURE:
<223> OTHER INFORMATION: CDR3

<400> SEQUENCE: 255

Tyr Ser Ser Ser Tyr Tyr Gln Asp Tyr
1               5

<210> SEQ ID NO 256
<211> LENGTH: 9
<212> TYPE: PRT
<213> ORGANISM: Artificial Sequence
<220> FEATURE:
<223> OTHER INFORMATION: CDR3

<400> SEQUENCE: 256

Tyr Ser Arg Gly Tyr Tyr Gln Asp Tyr
1               5

<210> SEQ ID NO 257
<211> LENGTH: 9
<212> TYPE: PRT
<213> ORGANISM: Artificial Sequence
<220> FEATURE:
<223> OTHER INFORMATION: CDR3

<400> SEQUENCE: 257

Tyr Ser Leu Gly Tyr Tyr Gln Asp Tyr
1               5

<210> SEQ ID NO 258
<211> LENGTH: 9
<212> TYPE: PRT
<213> ORGANISM: Artificial Sequence
<220> FEATURE:
<223> OTHER INFORMATION: CDR3

<400> SEQUENCE: 258

Tyr Ser Leu Gly Tyr Tyr Gln Asp Tyr
1               5

<210> SEQ ID NO 259
<211> LENGTH: 9
<212> TYPE: PRT
<213> ORGANISM: Artificial Sequence
<220> FEATURE:
<223> OTHER INFORMATION: CDR3

<400> SEQUENCE: 259

Tyr Ser Leu Gly Tyr Tyr Gln Asp Tyr
1               5

<210> SEQ ID NO 260
<211> LENGTH: 9
<212> TYPE: PRT
<213> ORGANISM: Artificial Sequence
<220> FEATURE:
<223> OTHER INFORMATION: CDR3

<400> SEQUENCE: 260

Tyr Ser Leu Gly Tyr Tyr Gln Asp Tyr
1               5

<210> SEQ ID NO 261
<211> LENGTH: 9
<212> TYPE: PRT
<213> ORGANISM: Artificial Sequence
<220> FEATURE:
<223> OTHER INFORMATION: CDR3

<400> SEQUENCE: 261

```
Tyr Ser Leu Gly Tyr Tyr Gln Asp Tyr
1               5

<210> SEQ ID NO 262
<211> LENGTH: 9
<212> TYPE: PRT
<213> ORGANISM: Artificial Sequence
<220> FEATURE:
<223> OTHER INFORMATION: CDR3

<400> SEQUENCE: 262

Tyr Ser Leu Gly Tyr Tyr Gln Asp Tyr
1               5

<210> SEQ ID NO 263
<211> LENGTH: 9
<212> TYPE: PRT
<213> ORGANISM: Artificial Sequence
<220> FEATURE:
<223> OTHER INFORMATION: CDR3

<400> SEQUENCE: 263

Tyr Ser Arg Lys Tyr Tyr Gln Asp Tyr
1               5

<210> SEQ ID NO 264
<211> LENGTH: 9
<212> TYPE: PRT
<213> ORGANISM: Artificial Sequence
<220> FEATURE:
<223> OTHER INFORMATION: CDR3

<400> SEQUENCE: 264

Tyr Ser Ser Arg Tyr Tyr His Asp Tyr
1               5

<210> SEQ ID NO 265
<211> LENGTH: 9
<212> TYPE: PRT
<213> ORGANISM: Artificial Sequence
<220> FEATURE:
<223> OTHER INFORMATION: CDR3

<400> SEQUENCE: 265

Tyr Ser Arg Lys Tyr Tyr Gln Asp Tyr
1               5

<210> SEQ ID NO 266
<211> LENGTH: 9
<212> TYPE: PRT
<213> ORGANISM: Artificial Sequence
<220> FEATURE:
<223> OTHER INFORMATION: CDR3

<400> SEQUENCE: 266

Tyr Ser Ser Arg Tyr Tyr His Asp Tyr
1               5

<210> SEQ ID NO 267
<211> LENGTH: 9
<212> TYPE: PRT
<213> ORGANISM: Artificial Sequence
<220> FEATURE:
<223> OTHER INFORMATION: CDR3

<400> SEQUENCE: 267
```

Tyr Ser Ser Arg Tyr Tyr His Asp Tyr
1               5

<210> SEQ ID NO 268
<211> LENGTH: 9
<212> TYPE: PRT
<213> ORGANISM: Artificial Sequence
<220> FEATURE:
<223> OTHER INFORMATION: CDR3

<400> SEQUENCE: 268

Tyr Ser Ser Arg Tyr Tyr His Asp Tyr
1               5

<210> SEQ ID NO 269
<211> LENGTH: 9
<212> TYPE: PRT
<213> ORGANISM: Artificial Sequence
<220> FEATURE:
<223> OTHER INFORMATION: CDR3

<400> SEQUENCE: 269

Tyr Ser Ser Arg Tyr Tyr His Asp Tyr
1               5

<210> SEQ ID NO 270
<211> LENGTH: 9
<212> TYPE: PRT
<213> ORGANISM: Artificial Sequence
<220> FEATURE:
<223> OTHER INFORMATION: CDR3

<400> SEQUENCE: 270

Tyr Ser Ser Arg Tyr Tyr His Asp Tyr
1               5

<210> SEQ ID NO 271
<211> LENGTH: 11
<212> TYPE: PRT
<213> ORGANISM: Artificial Sequence
<220> FEATURE:
<223> OTHER INFORMATION: FR4

<400> SEQUENCE: 271

Trp Gly Gln Gly Thr Gln Val Thr Val Ser Ser
1               5                   10

<210> SEQ ID NO 272
<211> LENGTH: 11
<212> TYPE: PRT
<213> ORGANISM: Artificial Sequence
<220> FEATURE:
<223> OTHER INFORMATION: FR4

<400> SEQUENCE: 272

Trp Gly Gln Gly Thr Gln Val Thr Val Ser Ser
1               5                   10

<210> SEQ ID NO 273
<211> LENGTH: 11
<212> TYPE: PRT
<213> ORGANISM: Artificial Sequence
<220> FEATURE:
<223> OTHER INFORMATION: FR4

<400> SEQUENCE: 273

Trp Gly Gln Gly Thr Gln Val Thr Val Ser Ser

-continued

```
1               5                   10

<210> SEQ ID NO 274
<211> LENGTH: 11
<212> TYPE: PRT
<213> ORGANISM: Artificial Sequence
<220> FEATURE:
<223> OTHER INFORMATION: FR4

<400> SEQUENCE: 274

Trp Gly Gln Gly Thr Gln Val Thr Val Ser Ser
1               5                   10

<210> SEQ ID NO 275
<211> LENGTH: 11
<212> TYPE: PRT
<213> ORGANISM: Artificial Sequence
<220> FEATURE:
<223> OTHER INFORMATION: FR4

<400> SEQUENCE: 275

Trp Gly Gln Gly Thr Gln Val Thr Val Ser Ser
1               5                   10

<210> SEQ ID NO 276
<211> LENGTH: 11
<212> TYPE: PRT
<213> ORGANISM: Artificial Sequence
<220> FEATURE:
<223> OTHER INFORMATION: FR4

<400> SEQUENCE: 276

Trp Gly Gln Gly Ile Gln Val Thr Val Ser Ser
1               5                   10

<210> SEQ ID NO 277
<211> LENGTH: 11
<212> TYPE: PRT
<213> ORGANISM: Artificial Sequence
<220> FEATURE:
<223> OTHER INFORMATION: FR4

<400> SEQUENCE: 277

Trp Gly Gln Gly Thr Gln Val Thr Val Ser Ser
1               5                   10

<210> SEQ ID NO 278
<211> LENGTH: 11
<212> TYPE: PRT
<213> ORGANISM: Artificial Sequence
<220> FEATURE:
<223> OTHER INFORMATION: FR4

<400> SEQUENCE: 278

Trp Gly Gln Gly Thr Gln Val Thr Val Ser Ser
1               5                   10

<210> SEQ ID NO 279
<211> LENGTH: 11
<212> TYPE: PRT
<213> ORGANISM: Artificial Sequence
<220> FEATURE:
<223> OTHER INFORMATION: FR4

<400> SEQUENCE: 279

Trp Gly Gln Gly Thr Gln Val Thr Val Ser Ser
1               5                   10
```

```
<210> SEQ ID NO 280
<211> LENGTH: 11
<212> TYPE: PRT
<213> ORGANISM: Artificial Sequence
<220> FEATURE:
<223> OTHER INFORMATION: FR4

<400> SEQUENCE: 280

Trp Gly Gln Gly Thr Gln Val Thr Val Ser Ser
1               5                   10

<210> SEQ ID NO 281
<211> LENGTH: 11
<212> TYPE: PRT
<213> ORGANISM: Artificial Sequence
<220> FEATURE:
<223> OTHER INFORMATION: FR4

<400> SEQUENCE: 281

Trp Gly Gln Gly Thr Gln Val Thr Val Ser Ser
1               5                   10

<210> SEQ ID NO 282
<211> LENGTH: 11
<212> TYPE: PRT
<213> ORGANISM: Artificial Sequence
<220> FEATURE:
<223> OTHER INFORMATION: FR4

<400> SEQUENCE: 282

Trp Gly Gln Gly Ile Gln Val Thr Val Ser Ser
1               5                   10

<210> SEQ ID NO 283
<211> LENGTH: 11
<212> TYPE: PRT
<213> ORGANISM: Artificial Sequence
<220> FEATURE:
<223> OTHER INFORMATION: FR4

<400> SEQUENCE: 283

Trp Gly Gln Gly Thr Gln Val Thr Val Ser Ser
1               5                   10

<210> SEQ ID NO 284
<211> LENGTH: 11
<212> TYPE: PRT
<213> ORGANISM: Artificial Sequence
<220> FEATURE:
<223> OTHER INFORMATION: FR4

<400> SEQUENCE: 284

Trp Gly Gln Gly Thr Gln Val Thr Val Ser Ser
1               5                   10

<210> SEQ ID NO 285
<211> LENGTH: 11
<212> TYPE: PRT
<213> ORGANISM: Artificial Sequence
<220> FEATURE:
<223> OTHER INFORMATION: FR4

<400> SEQUENCE: 285

Trp Gly Gln Gly Thr Gln Val Thr Val Ser Ser
1               5                   10
```

<210> SEQ ID NO 286
<211> LENGTH: 11
<212> TYPE: PRT
<213> ORGANISM: Artificial Sequence
<220> FEATURE:
<223> OTHER INFORMATION: FR4

<400> SEQUENCE: 286

Trp Gly Gln Gly Thr Gln Val Thr Val Ser Ser
1               5                   10

<210> SEQ ID NO 287
<211> LENGTH: 11
<212> TYPE: PRT
<213> ORGANISM: Artificial Sequence
<220> FEATURE:
<223> OTHER INFORMATION: FR4

<400> SEQUENCE: 287

Trp Gly Gln Gly Thr Gln Val Thr Val Ser Ser
1               5                   10

<210> SEQ ID NO 288
<211> LENGTH: 11
<212> TYPE: PRT
<213> ORGANISM: Artificial Sequence
<220> FEATURE:
<223> OTHER INFORMATION: FR4

<400> SEQUENCE: 288

Trp Gly Gln Gly Thr Gln Val Thr Val Ser Ser
1               5                   10

<210> SEQ ID NO 289
<211> LENGTH: 11
<212> TYPE: PRT
<213> ORGANISM: Artificial Sequence
<220> FEATURE:
<223> OTHER INFORMATION: FR4

<400> SEQUENCE: 289

Trp Gly Gln Gly Thr Gln Val Thr Val Ser Ser
1               5                   10

<210> SEQ ID NO 290
<211> LENGTH: 11
<212> TYPE: PRT
<213> ORGANISM: Artificial Sequence
<220> FEATURE:
<223> OTHER INFORMATION: FR4

<400> SEQUENCE: 290

Trp Gly Gln Gly Thr Gln Val Thr Val Ser Ser
1               5                   10

<210> SEQ ID NO 291
<211> LENGTH: 11
<212> TYPE: PRT
<213> ORGANISM: Artificial Sequence
<220> FEATURE:
<223> OTHER INFORMATION: FR4

<400> SEQUENCE: 291

Trp Gly Gln Gly Thr Gln Val Thr Val Ser Ser
1               5                   10

```
<210> SEQ ID NO 292
<211> LENGTH: 11
<212> TYPE: PRT
<213> ORGANISM: Artificial Sequence
<220> FEATURE:
<223> OTHER INFORMATION: FR4

<400> SEQUENCE: 292

Trp Gly Gln Gly Thr Gln Val Thr Val Ser Ser
1               5                   10

<210> SEQ ID NO 293
<211> LENGTH: 11
<212> TYPE: PRT
<213> ORGANISM: Artificial Sequence
<220> FEATURE:
<223> OTHER INFORMATION: FR4

<400> SEQUENCE: 293

Trp Gly Gln Gly Thr Gln Val Thr Val Ser Ser
1               5                   10

<210> SEQ ID NO 294
<211> LENGTH: 11
<212> TYPE: PRT
<213> ORGANISM: Artificial Sequence
<220> FEATURE:
<223> OTHER INFORMATION: FR4

<400> SEQUENCE: 294

Trp Gly Gln Gly Thr Gln Val Thr Val Ser Ser
1               5                   10

<210> SEQ ID NO 295
<211> LENGTH: 11
<212> TYPE: PRT
<213> ORGANISM: Artificial Sequence
<220> FEATURE:
<223> OTHER INFORMATION: FR4

<400> SEQUENCE: 295

Trp Gly Gln Gly Thr Gln Val Thr Val Ser Ser
1               5                   10

<210> SEQ ID NO 296
<211> LENGTH: 11
<212> TYPE: PRT
<213> ORGANISM: Artificial Sequence
<220> FEATURE:
<223> OTHER INFORMATION: FR4

<400> SEQUENCE: 296

Trp Gly Gln Gly Thr Gln Val Thr Val Ser Ser
1               5                   10

<210> SEQ ID NO 297
<211> LENGTH: 11
<212> TYPE: PRT
<213> ORGANISM: Artificial Sequence
<220> FEATURE:
<223> OTHER INFORMATION: FR4

<400> SEQUENCE: 297

Trp Gly Gln Gly Thr Gln Val Thr Val Ser Ser
1               5                   10

<210> SEQ ID NO 298
```

```
<211> LENGTH: 11
<212> TYPE: PRT
<213> ORGANISM: Artificial Sequence
<220> FEATURE:
<223> OTHER INFORMATION: FR4

<400> SEQUENCE: 298

Trp Gly Gln Gly Thr Gln Val Thr Val Ser Ser
1               5                   10

<210> SEQ ID NO 299
<211> LENGTH: 11
<212> TYPE: PRT
<213> ORGANISM: Artificial Sequence
<220> FEATURE:
<223> OTHER INFORMATION: FR4

<400> SEQUENCE: 299

Trp Gly Gln Gly Thr Gln Val Thr Val Ser Ser
1               5                   10

<210> SEQ ID NO 300
<211> LENGTH: 11
<212> TYPE: PRT
<213> ORGANISM: Artificial Sequence
<220> FEATURE:
<223> OTHER INFORMATION: FR4

<400> SEQUENCE: 300

Trp Gly Gln Gly Thr Gln Val Thr Val Ser Ser
1               5                   10

<210> SEQ ID NO 301
<211> LENGTH: 11
<212> TYPE: PRT
<213> ORGANISM: Artificial Sequence
<220> FEATURE:
<223> OTHER INFORMATION: FR4

<400> SEQUENCE: 301

Trp Gly Gln Gly Thr Gln Val Thr Val Ser Ser
1               5                   10

<210> SEQ ID NO 302
<211> LENGTH: 11
<212> TYPE: PRT
<213> ORGANISM: Artificial Sequence
<220> FEATURE:
<223> OTHER INFORMATION: FR4

<400> SEQUENCE: 302

Trp Gly Gln Gly Thr Gln Val Thr Val Ser Ser
1               5                   10

<210> SEQ ID NO 303
<211> LENGTH: 11
<212> TYPE: PRT
<213> ORGANISM: Artificial Sequence
<220> FEATURE:
<223> OTHER INFORMATION: FR4

<400> SEQUENCE: 303

Trp Gly Gln Gly Thr Gln Val Thr Val Ser Ser
1               5                   10

<210> SEQ ID NO 304
<211> LENGTH: 11
```

```
<212> TYPE: PRT
<213> ORGANISM: Artificial Sequence
<220> FEATURE:
<223> OTHER INFORMATION: FR4

<400> SEQUENCE: 304

Trp Gly Gln Gly Thr Gln Val Thr Val Ser Ser
1               5                   10

<210> SEQ ID NO 305
<211> LENGTH: 11
<212> TYPE: PRT
<213> ORGANISM: Artificial Sequence
<220> FEATURE:
<223> OTHER INFORMATION: FR4

<400> SEQUENCE: 305

Trp Gly Gln Gly Thr Gln Val Thr Val Ser Ser
1               5                   10

<210> SEQ ID NO 306
<211> LENGTH: 11
<212> TYPE: PRT
<213> ORGANISM: Artificial Sequence
<220> FEATURE:
<223> OTHER INFORMATION: FR4

<400> SEQUENCE: 306

Trp Gly Gln Gly Thr Gln Val Thr Val Ser Ser
1               5                   10

<210> SEQ ID NO 307
<211> LENGTH: 11
<212> TYPE: PRT
<213> ORGANISM: Artificial Sequence
<220> FEATURE:
<223> OTHER INFORMATION: FR4

<400> SEQUENCE: 307

Trp Gly Gln Gly Thr Gln Val Thr Val Ser Ser
1               5                   10

<210> SEQ ID NO 308
<211> LENGTH: 11
<212> TYPE: PRT
<213> ORGANISM: Artificial Sequence
<220> FEATURE:
<223> OTHER INFORMATION: FR4

<400> SEQUENCE: 308

Trp Gly Gln Gly Thr Leu Val Thr Val Ser Ser
1               5                   10

<210> SEQ ID NO 309
<211> LENGTH: 11
<212> TYPE: PRT
<213> ORGANISM: Artificial Sequence
<220> FEATURE:
<223> OTHER INFORMATION: FR4

<400> SEQUENCE: 309

Trp Gly Gln Gly Thr Leu Val Thr Val Ser Ser
1               5                   10

<210> SEQ ID NO 310
<211> LENGTH: 11
<212> TYPE: PRT
```

```
<213> ORGANISM: Artificial Sequence
<220> FEATURE:
<223> OTHER INFORMATION: FR4

<400> SEQUENCE: 310

Trp Gly Gln Gly Thr Leu Val Thr Val Ser Ser
1               5                   10

<210> SEQ ID NO 311
<211> LENGTH: 11
<212> TYPE: PRT
<213> ORGANISM: Artificial Sequence
<220> FEATURE:
<223> OTHER INFORMATION: FR4

<400> SEQUENCE: 311

Trp Gly Gln Gly Thr Leu Val Thr Val Ser Ser
1               5                   10

<210> SEQ ID NO 312
<211> LENGTH: 11
<212> TYPE: PRT
<213> ORGANISM: Artificial Sequence
<220> FEATURE:
<223> OTHER INFORMATION: FR4

<400> SEQUENCE: 312

Trp Gly Gln Gly Thr Leu Val Thr Val Ser Ser
1               5                   10

<210> SEQ ID NO 313
<211> LENGTH: 11
<212> TYPE: PRT
<213> ORGANISM: Artificial Sequence
<220> FEATURE:
<223> OTHER INFORMATION: FR4

<400> SEQUENCE: 313

Trp Gly Gln Gly Thr Leu Val Thr Val Ser Ser
1               5                   10

<210> SEQ ID NO 314
<211> LENGTH: 11
<212> TYPE: PRT
<213> ORGANISM: Artificial Sequence
<220> FEATURE:
<223> OTHER INFORMATION: FR4

<400> SEQUENCE: 314

Trp Gly Gln Gly Thr Leu Val Thr Val Ser Ser
1               5                   10

<210> SEQ ID NO 315
<211> LENGTH: 11
<212> TYPE: PRT
<213> ORGANISM: Artificial Sequence
<220> FEATURE:
<223> OTHER INFORMATION: FR4

<400> SEQUENCE: 315

Trp Gly Gln Gly Thr Leu Val Thr Val Ser Ser
1               5                   10

<210> SEQ ID NO 316
<211> LENGTH: 117
<212> TYPE: PRT
<213> ORGANISM: Artificial Sequence
```

```
<220> FEATURE:
<223> OTHER INFORMATION: AS01274 synthesized sdAb

<400> SEQUENCE: 316

Gln Val Gln Leu Val Glu Ser Gly Gly Gly Leu Val Gln Pro Gly Gly
1               5                   10                  15

Ser Leu Arg Leu Ser Cys Val Ala Ser Gly Ser Ile Ala Ser Ile Ala
            20                  25                  30

Thr Met Ala Trp Tyr Arg Gln Ala Pro Gly Gln Gln Arg Glu Leu Val
        35                  40                  45

Ala Gly Ile Thr Arg Gly Gly Ser Thr Lys Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Asp Asp Thr Ala Val Tyr Tyr Cys Thr
                85                  90                  95

Asp Tyr Ser Arg Lys Tyr Tyr Gln Asp Tyr Trp Gly Gln Gly Thr Gln
            100                 105                 110

Val Thr Val Ser Ser
        115

<210> SEQ ID NO 317
<211> LENGTH: 117
<212> TYPE: PRT
<213> ORGANISM: Artificial Sequence
<220> FEATURE:
<223> OTHER INFORMATION: AS01276 synthesized sdAb

<400> SEQUENCE: 317

Glu Val Gln Leu Val Glu Cys Gly Gly Gly Leu Val Gln Pro Gly Gly
1               5                   10                  15

Ser Leu Arg Leu Ser Cys Val Ala Ser Gly Ser Ile Ala Ser Ile Ala
            20                  25                  30

Thr Met Ala Trp Tyr Arg Gln Ala Pro Gly Gln Gln Arg Glu Leu Val
        35                  40                  45

Ala Gly Ile Thr Arg Gly Gly Ser Thr Lys Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Thr
                85                  90                  95

Asp Tyr Ser Arg Gly Tyr Tyr Gln Asp Tyr Trp Gly Gln Gly Thr Gln
            100                 105                 110

Val Thr Val Ser Ser
        115

<210> SEQ ID NO 318
<211> LENGTH: 117
<212> TYPE: PRT
<213> ORGANISM: Artificial Sequence
<220> FEATURE:
<223> OTHER INFORMATION: AS01278 synthesized sdAb

<400> SEQUENCE: 318

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30
```

```
Thr Met Ala Trp Tyr Arg Gln Ala Pro Gly Lys Gln Arg Glu Leu Val
        35                  40                  45

Ala Gly Ile Thr Arg Ser Gly Thr Thr Thr Tyr Ala Gly Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                 85                  90                  95

Asp Tyr Ser Ser Ser Tyr Tyr Gln Asp Tyr Trp Gly Gln Gly Thr Gln
                100                 105                 110

Val Thr Val Ser Ser
            115

<210> SEQ ID NO 319
<211> LENGTH: 117
<212> TYPE: PRT
<213> ORGANISM: Artificial Sequence
<220> FEATURE:
<223> OTHER INFORMATION: AS01281 synthesized sdAb

<400> SEQUENCE: 319

Glu Val Gln Leu Val Glu Cys Gly Gly Gly Leu Val Gln Pro Gly Gly
 1               5                  10                  15

Ser Leu Arg Leu Ser Cys Ala Ala Ser Gly Ser Ile Phe Ser Ile Asn
                 20                  25                  30

Thr Met Gly Trp Tyr Arg Gln Ala Pro Gly Lys Gln Arg Glu Leu Val
        35                  40                  45

Ala Gly Ile Thr Arg Gly Gly Ser Thr Lys Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Lys Pro Glu Asp Thr Ala Val Tyr Tyr Cys Thr
                 85                  90                  95

Asp Tyr Ser Arg Ser Tyr Tyr Gln Asp Tyr Trp Gly Gln Gly Thr Gln
                100                 105                 110

Val Thr Val Ser Ser
            115

<210> SEQ ID NO 320
<211> LENGTH: 117
<212> TYPE: PRT
<213> ORGANISM: Artificial Sequence
<220> FEATURE:
<223> OTHER INFORMATION: AS01282 synthesized sdAb

<400> SEQUENCE: 320

Gln Val Lys Leu Glu Glu Ser Gly Gly Gly Leu Val Gln Pro Gly Gly
 1               5                  10                  15

Ser Leu Arg Leu Ser Cys Ala Ala Ser Gly Ser Ile Phe Ser Ile Asn
                 20                  25                  30

Thr Met Gly Trp Tyr Arg Gln Arg Pro Gly Lys Gln Arg Glu Leu Val
        35                  40                  45

Ala Ala Ile Thr Arg Gly Gly Asn Thr Asn Tyr Ala Asp Ser Val Lys
 50                  55                  60

Gly Arg Phe Ser Ile Ser Arg Asp Asn Ala Lys Asn Thr Met Tyr Leu
 65                  70                  75                  80

Gln Met Asn Ser Leu Lys Pro Glu Asp Thr Ala Val Tyr Tyr Cys Thr
                 85                  90                  95
```

-continued

Asp Tyr Ser Arg Arg Tyr Tyr Gln Asp Asp Trp Gly Gln Gly Thr Gln
            100                 105                 110

Val Thr Val Ser Ser
        115

<210> SEQ ID NO 321
<211> LENGTH: 114
<212> TYPE: PRT
<213> ORGANISM: Artificial Sequence
<220> FEATURE:
<223> OTHER INFORMATION: AS01284 synthesized sdAb

<400> SEQUENCE: 321

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Arg Pro Leu Arg
            20                  25                  30

Phe Met Ala Trp Tyr Arg Gln Ala Pro Gly Asn Gln Arg Gly Leu Val
        35                  40                  45

Ala Ala Glu Thr Ser Gly Gly Thr Ile Arg Tyr Ala Asp Ser Val Lys
    50                  55                  60

Gly Arg Phe Thr Ile Ser Arg Asp Asn Ala Lys Asn Thr Met Tyr Leu
65                  70                  75                  80

Gln Met Asn Ser Leu Lys Pro Glu Asp Thr Ala Val Tyr Tyr Cys Ala
                85                  90                  95

Ala Arg Asp Leu Asp Asp Tyr Trp Gly Gln Gly Ile Gln Val Thr Val
            100                 105                 110

Ser Ser

<210> SEQ ID NO 322
<211> LENGTH: 114
<212> TYPE: PRT
<213> ORGANISM: Artificial Sequence
<220> FEATURE:
<223> OTHER INFORMATION: AS01285 synthesized sdAb

<400> SEQUENCE: 322

Gln Val Gln Leu Val Glu Ser Gly Gly Gly Leu Val Gln Ala Gly Gly
1               5                   10                  15

Ser Leu Arg Leu Ser Cys Ala Ala Ser Arg Ser Ile Ser Thr Leu Arg
            20                  25                  30

Phe Met Ala Trp Tyr Arg Gln Ala Pro Gly Glu Gln Arg Glu Leu Val
        35                  40                  45

Ala Ala Glu Thr Ser Ala Gly Arg Leu Thr Tyr Ala Asp Ser Val Lys
    50                  55                  60

Gly Arg Phe Thr Val Ser Arg Asp Asn Ala Lys Asp Thr Ile Asp Leu
65                  70                  75                  80

Gln Met Asn Ser Leu Lys Pro Glu Asp Thr Gly Val Tyr Tyr Cys Ala
                85                  90                  95

Ala Arg Gly Leu Ala Asp Tyr Trp Gly Gln Gly Thr Gln Val Thr Val
            100                 105                 110

Ser Ser

<210> SEQ ID NO 323
<211> LENGTH: 117
<212> TYPE: PRT
<213> ORGANISM: Artificial Sequence
<220> FEATURE:

<223> OTHER INFORMATION: AS01288 synthesized sdAb

<400> SEQUENCE: 323

Gln Val Gln Leu Val Glu Ser Gly Gly Gly Leu Val Gln Pro Gly Gly
1               5                   10                  15

Ser Leu Arg Leu Ser Cys Val Ala Ser Gly Ser Ile Phe Ser Ile Asn
            20                  25                  30

Thr Met Gly Trp Tyr Arg Gln Ala Pro Gly Lys Gln Arg Glu Leu Val
        35                  40                  45

Ala Ala Ile Thr Arg Gly Gly Asn Thr Lys Tyr Thr Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Asp Tyr Ser Arg Ser Tyr Tyr Gln Asp Tyr Trp Gly Gln Gly Thr Gln
            100                 105                 110

Val Thr Val Ser Ser
        115

<210> SEQ ID NO 324
<211> LENGTH: 117
<212> TYPE: PRT
<213> ORGANISM: Artificial Sequence
<220> FEATURE:
<223> OTHER INFORMATION: AS01289 synthesized sdAb

<400> SEQUENCE: 324

Gln Val Lys Leu Glu Glu Ser Gly Gly Gly Leu Val Gln Pro Gly Gly
1               5                   10                  15

Ser Leu Arg Leu Ser Cys Ala Ala Ser Gly Ser Ile Phe Ser Ile Ala
            20                  25                  30

Thr Met Ala Trp Tyr Arg Gln Ala Pro Gly Lys Gln Arg Glu Leu Val
        35                  40                  45

Ala Gly Ile Thr Arg Ser Gly Ser Thr Asn Tyr Arg Asp Ser Val Lys
    50                  55                  60

Gly Arg Phe Thr Ile Ser Arg Asp Asn Ala Lys Asn Thr Met Tyr Leu
65                  70                  75                  80

Gln Met Asn Ser Leu Lys Pro Glu Asp Thr Ala Val Tyr Tyr Cys Thr
                85                  90                  95

Asp Tyr Ser Ser Arg Tyr Tyr His Asp Tyr Trp Gly Gln Gly Thr Gln
            100                 105                 110

Val Thr Val Ser Ser
        115

<210> SEQ ID NO 325
<211> LENGTH: 114
<212> TYPE: PRT
<213> ORGANISM: Artificial Sequence
<220> FEATURE:
<223> OTHER INFORMATION: AS01290 synthesized sdAb

<400> SEQUENCE: 325

Gln Val Gln Leu Val Glu Ser Gly Gly Gly Leu Val Gln Ala Gly Gly
1               5                   10                  15

Ser Leu Arg Leu Ser Cys Ala Ala Ser Arg Ser Ile Ser Thr Leu Arg
            20                  25                  30

Phe Met Ala Trp Tyr Arg Gln Ala Pro Gly Glu Gln Arg Glu Leu Val

```
                35                  40                  45
Ala Ala Glu Thr Ser Ala Gly Arg Leu Thr Tyr Ala Asp Ser Val Lys
 50                  55                  60

Gly Arg Phe Thr Val Ser Arg Asp Asn Ala Lys Asp Thr Ile Asp Leu
 65                  70                  75                  80

Gln Met Asn Ser Leu Lys Pro Glu Asp Thr Gly Val Tyr Tyr Cys Ala
                 85                  90                  95

Ala Arg Gly Leu Ala Asp Tyr Trp Gly Gln Gly Thr Gln Val Thr Val
                100                 105                 110

Ser Ser

<210> SEQ ID NO 326
<211> LENGTH: 117
<212> TYPE: PRT
<213> ORGANISM: Artificial Sequence
<220> FEATURE:
<223> OTHER INFORMATION: AS01291 synthesized sdAb

<400> SEQUENCE: 326

Gln Val Lys Leu Glu Glu Ser Gly Gly Gly Leu Val Gln Pro Gly Gly
 1               5                  10                  15

Ser Leu Arg Leu Ser Cys Ala Ala Ser Gly Ser Ile Val Ser Ile Ala
                20                  25                  30

Thr Met Ala Trp Tyr Arg Gln Ala Pro Gly Lys Gln Arg Glu Leu Val
                35                  40                  45

Ala Gly Ile Thr Arg Gly Gly Ser Thr Lys Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met His Ser Leu Lys Pro Glu Asp Thr Ala Val Tyr Tyr Cys Thr
                 85                  90                  95

Asp Tyr Ser Arg Thr Tyr Tyr Glu Asp His Trp Gly Gln Gly Thr Gln
                100                 105                 110

Val Thr Val Ser Ser
        115

<210> SEQ ID NO 327
<211> LENGTH: 117
<212> TYPE: PRT
<213> ORGANISM: Artificial Sequence
<220> FEATURE:
<223> OTHER INFORMATION: AS01292 synthesized sdAb

<400> SEQUENCE: 327

His Val Gln Leu Val Glu Ser Gly Gly Gly Leu Val Gln Pro Gly Gly
 1               5                  10                  15

Ser Leu Arg Leu Ser Cys Val Ala Ser Gly Ser Ile Ala Ser Val Ala
                20                  25                  30

Thr Met Ala Trp Tyr Arg Gln Ala Pro Gly Gln Gln Arg Glu Leu Val
                35                  40                  45

Ala Gly Ile Thr Arg Gly Gly Ser Thr Lys Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Lys Pro Glu Asp Thr Ala Val Tyr Tyr Cys Thr
                 85                  90                  95

Asp Tyr Ser Arg Gly Tyr Tyr Gln Asp Tyr Trp Gly Gln Gly Ile Gln
```

Val Thr Val Ser Ser
        115

<210> SEQ ID NO 328
<211> LENGTH: 117
<212> TYPE: PRT
<213> ORGANISM: Artificial Sequence
<220> FEATURE:
<223> OTHER INFORMATION: AS01293 synthesized sdAb

<400> SEQUENCE: 328

Gln Val Gln Leu Val Glu Ser Gly Gly Gly Ser Val Gln Pro Gly Gly
1               5                   10                  15

Ser Leu Arg Leu Ser Cys Ala Ala Ser Gly Ser Ile Ala Ser Ile Asn
            20                  25                  30

Thr Met Ala Trp Tyr Arg Gln Ser Pro Gly Lys Gln Arg Glu Leu Val
        35                  40                  45

Ala Gly Ile Thr Arg Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Asp Tyr Ser Leu Gly Tyr Tyr Gln Asp Tyr Trp Gly Gln Gly Thr Gln
            100                 105                 110

Val Thr Val Ser Ser
        115

<210> SEQ ID NO 329
<211> LENGTH: 117
<212> TYPE: PRT
<213> ORGANISM: Artificial Sequence
<220> FEATURE:
<223> OTHER INFORMATION: AS01296 synthesized sdAb

<400> SEQUENCE: 329

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Thr Met Ala Trp Tyr Arg Gln Ala Pro Gly Lys Gln Arg Glu Leu Val
        35                  40                  45

Ala Gly Ile Thr Arg Ser Gly Thr Thr Asn Tyr Ala Gly Ser Val Lys
    50                  55                  60

Gly Arg Phe Thr Ile Ser Arg Asp Asn Ala Lys Asn Thr Val Tyr Leu
65                  70                  75                  80

Gln Met Asn Gly Leu Lys Pro Glu Asp Thr Ala Val Tyr Tyr Cys Thr
                85                  90                  95

Asp Tyr Ser Arg Arg Tyr Tyr Gln Asp Asp Trp Gly Gln Gly Thr Gln
            100                 105                 110

Val Thr Val Ser Ser
        115

<210> SEQ ID NO 330
<211> LENGTH: 117
<212> TYPE: PRT
<213> ORGANISM: Artificial Sequence
<220> FEATURE:

<223> OTHER INFORMATION: AS01297 synthesized sdAb

<400> SEQUENCE: 330

Glu Val Gln Leu Val Glu Cys Gly Gly Gly Leu Val Gln Pro Gly Gly
1               5                   10                  15

Ser Leu Arg Leu Ser Cys Ala Ala Ser Gly Ser Ile Phe Ser Ile Ala
            20                  25                  30

Thr Met Ala Trp Tyr Arg Gln Ala Pro Gly Lys Gln Arg Glu Leu Val
        35                  40                  45

Ala Gly Ile Thr Arg Ser Gly Ser Thr Asn Tyr Arg Asp Ser Val Lys
    50                  55                  60

Gly Arg Phe Thr Ile Ser Arg Asp Asn Ala Lys Asn Thr Met Tyr Leu
65                  70                  75                  80

Gln Met Asn Ser Leu Lys Pro Glu Asp Thr Ala Val Tyr Tyr Cys Thr
                85                  90                  95

Asp Tyr Ser Ser Arg Tyr Tyr His Asp Tyr Trp Gly Gln Gly Thr Gln
            100                 105                 110

Val Thr Val Ser Ser
        115

<210> SEQ ID NO 331
<211> LENGTH: 117
<212> TYPE: PRT
<213> ORGANISM: Artificial Sequence
<220> FEATURE:
<223> OTHER INFORMATION: AS01298 synthesized sdAb

<400> SEQUENCE: 331

Gln Val Gln Leu Val Glu Ser Gly Gly Gly Leu Val Gln Ser Gly Gly
1               5                   10                  15

Ser Leu Arg Leu Ser Cys Ala Ala Ser Gly Thr Ile Phe Ala Ile Asn
            20                  25                  30

Thr Met Ala Trp Tyr Arg Gln Ala Pro Gly Gln Gln Arg Glu Leu Val
        35                  40                  45

Ala Gly Ile Thr Arg Gly Gly Ser Thr Lys Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Thr
                85                  90                  95

Asp Tyr Ser Arg Gly Tyr Tyr Gln Asp Tyr Trp Gly Gln Gly Thr Gln
            100                 105                 110

Val Thr Val Ser Ser
        115

<210> SEQ ID NO 332
<211> LENGTH: 117
<212> TYPE: PRT
<213> ORGANISM: Artificial Sequence
<220> FEATURE:
<223> OTHER INFORMATION: AS01299 synthesized sdAb

<400> SEQUENCE: 332

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Ala
            20                  25                  30

Thr Met Ala Trp Tyr Arg Gln Ala Pro Gly Lys Gln Arg Glu Leu Val

```
                35                  40                  45
Ala Gly Ile Thr Arg Ser Gly Ser Thr Asn Tyr Arg Asp Ser Val Lys
             50                  55                  60
Gly Arg Phe Thr Ile Ser Arg Asp Asn Ala Lys Asn Thr Met Tyr Leu
 65                  70                  75                  80
Gln Met Asn Ser Leu Lys Pro Glu Asp Thr Ala Val Tyr Tyr Cys Thr
                 85                  90                  95
Asp Tyr Ser Ser Arg Tyr Tyr His Asp Tyr Trp Gly Gln Gly Thr Gln
            100                 105                 110
Val Thr Val Ser Ser
        115

<210> SEQ ID NO 333
<211> LENGTH: 117
<212> TYPE: PRT
<213> ORGANISM: Artificial Sequence
<220> FEATURE:
<223> OTHER INFORMATION: AS01300 synthesized sdAb

<400> SEQUENCE: 333

Gln Val Gln Leu Val Glu Ser Gly Gly Gly Leu Val Gln Pro Gly Gly
  1               5                  10                  15
Ser Leu Arg Leu Ser Cys Ala Ala Ser Gly Ser Ile Ala Ser Ile Asn
             20                  25                  30
Thr Met Ala Trp Tyr Arg Gln Ala Pro Gly Lys Gln Arg Glu Leu Val
                35                  40                  45
Ala Gly Ile Thr Ser Gly Gly Ser Thr Lys Tyr Ala Asp Ser Val Lys
             50                  55                  60
Gly Arg Phe Thr Ile Ser Arg Asp Asn Ala Lys Asn Thr Val Tyr Leu
 65                  70                  75                  80
Gln Met Asn Asn Leu Lys Pro Glu Asp Thr Ala Ile Tyr Tyr Cys Thr
                 85                  90                  95
Asp Tyr Ser Lys Arg Tyr Tyr Gln Asp Tyr Trp Gly Gln Gly Thr Gln
            100                 105                 110
Val Thr Val Ser Ser
        115

<210> SEQ ID NO 334
<211> LENGTH: 117
<212> TYPE: PRT
<213> ORGANISM: Artificial Sequence
<220> FEATURE:
<223> OTHER INFORMATION: AS01302 synthesized sdAb

<400> SEQUENCE: 334

Gln Val Lys Leu Glu Glu Ser Gly Gly Gly Leu Val Gln Pro Gly Gly
  1               5                  10                  15
Ser Leu Thr Leu Ser Cys Ala Ala Ser Gly Ser Ile Phe Ser Ile Asn
             20                  25                  30
Thr Met Ala Trp Tyr Arg Gln Ala Pro Gly Lys Gln Arg Glu Leu Val
                35                  40                  45
Ala Gly Ile Thr Arg Ser Gly Thr Thr Asn Tyr Ala Gly Ser Val Lys
             50                  55                  60
Gly Arg Phe Thr Ile Ser Arg Asp Asn Ala Lys Asn Thr Val Tyr Leu
 65                  70                  75                  80
Gln Met Asn Ser Leu Lys Pro Glu Asp Thr Ala Val Tyr Tyr Cys Thr
                 85                  90                  95
```

```
Asp Tyr Ser Arg Lys Tyr Glu Asp Gln Trp Gly Gln Gly Thr Gln
                100                 105                 110

Val Thr Val Ser Ser
        115

<210> SEQ ID NO 335
<211> LENGTH: 117
<212> TYPE: PRT
<213> ORGANISM: Artificial Sequence
<220> FEATURE:
<223> OTHER INFORMATION: AS01303 synthesized sdAb

<400> SEQUENCE: 335

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Ala Ser Ile Asn
            20                  25                  30

Thr Met Ala Trp Tyr Arg Gln Ala Pro Gly Gln Gln Arg Glu Leu Val
        35                  40                  45

Ala Gly Ile Thr Arg Gly Gly Ser Thr Lys Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Thr
                85                  90                  95

Asp Tyr Ser Arg Gly Tyr Tyr Gln Asp Tyr Trp Gly Gln Gly Thr Gln
                100                 105                 110

Val Thr Val Ser Ser
        115

<210> SEQ ID NO 336
<211> LENGTH: 117
<212> TYPE: PRT
<213> ORGANISM: Artificial Sequence
<220> FEATURE:
<223> OTHER INFORMATION: AS01304 synthesized sdAb

<400> SEQUENCE: 336

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Thr Met Gly Trp Tyr Arg Gln Ala Pro Gly Lys Gln Arg Glu Leu Val
        35                  40                  45

Ala Gly Ile Thr Arg Gly Gly Ser Thr Lys Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Thr
                85                  90                  95

Asp Tyr Ser Arg Ser Tyr Tyr Gln Asp Tyr Trp Gly Gln Gly Thr Gln
                100                 105                 110

Val Thr Val Ser Ser
        115

<210> SEQ ID NO 337
<211> LENGTH: 117
<212> TYPE: PRT
<213> ORGANISM: Artificial Sequence
```

<220> FEATURE:
<223> OTHER INFORMATION: AS01306 synthesized sdAb

<400> SEQUENCE: 337

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Thr Met Gly Trp Tyr Arg Gln Ala Pro Gly Lys Gln Arg Glu Leu Val
        35                  40                  45

Ala Gly Ile Thr Arg Gly Gly Thr Thr Asn Tyr Ala Asn Ser Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Asp Tyr Ser Ser Arg Tyr Tyr His Asp Tyr Trp Gly Gln Gly Thr Gln
            100                 105                 110

Val Thr Val Ser Ser
        115

<210> SEQ ID NO 338
<211> LENGTH: 117
<212> TYPE: PRT
<213> ORGANISM: Artificial Sequence
<220> FEATURE:
<223> OTHER INFORMATION: AS01308 synthesized sdAb

<400> SEQUENCE: 338

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Ala Ser Ile Asn
            20                  25                  30

Thr Met Ala Trp Tyr Arg Gln Ala Pro Gly Lys Gln Arg Glu Leu Val
        35                  40                  45

Ala Gly Ile Thr Arg Ser Gly Thr Thr Thr Tyr Ala Gly Ser Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Asp Tyr Ser Ser Ser Tyr Tyr Asp Asp Tyr Trp Gly Gln Gly Thr Gln
            100                 105                 110

Val Thr Val Ser Ser
        115

<210> SEQ ID NO 339
<211> LENGTH: 117
<212> TYPE: PRT
<213> ORGANISM: Artificial Sequence
<220> FEATURE:
<223> OTHER INFORMATION: AS01309 synthesized sdAb

<400> SEQUENCE: 339

Gln Val Gln Leu Val Glu Ser Gly Gly Gly Leu Val Gln Pro Gly Gly
1               5                   10                  15

Ser Leu Arg Leu Ser Cys Ala Ser Gly Ser Ile Phe Ser Ile Asn
            20                  25                  30

```
Thr Met Gly Trp Tyr Arg Gln Arg Pro Gly Lys Gln Arg Glu Leu Val
            35                  40                  45

Ala Ala Ile Thr Arg Gly Gly Asn Thr Asn Tyr Ala Asp Ser Val Lys
 50                  55                  60

Gly Arg Phe Ser Ile Ser Arg Asp Asn Ala Lys Asn Thr Met Tyr Leu
 65                  70                  75                  80

Gln Met Asn Ser Leu Lys Pro Glu Asp Thr Ala Val Tyr Tyr Cys Thr
                85                  90                  95

Asp Tyr Ser Arg Arg Tyr Tyr Gln Asp Asp Trp Gly Gln Gly Thr Gln
                100                 105                 110

Val Thr Val Ser Ser
            115

<210> SEQ ID NO 340
<211> LENGTH: 117
<212> TYPE: PRT
<213> ORGANISM: Artificial Sequence
<220> FEATURE:
<223> OTHER INFORMATION: AS01310 synthesized sdAb

<400> SEQUENCE: 340

Gln Val Gln Leu Val Glu Ser Gly Gly Gly Leu Val Gln Ala Gly Gly
 1               5                   10                  15

Ser Leu Arg Leu Ser Cys Val Ala Ser Gly Ser Ile Ala Ser Ile Ala
                20                  25                  30

Thr Met Ala Trp Tyr Arg Gln Ala Pro Gly Gln Gln Arg Glu Leu Val
            35                  40                  45

Ala Gly Ile Thr Arg Gly Gly Ser Thr His Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Glu Pro Glu Asp Thr Ala Val Tyr Tyr Cys Thr
                85                  90                  95

Asp Tyr Ser Arg Arg Tyr Tyr Glu Asp Tyr Trp Gly Gln Gly Thr Gln
                100                 105                 110

Val Thr Val Ser Ser
            115

<210> SEQ ID NO 341
<211> LENGTH: 117
<212> TYPE: PRT
<213> ORGANISM: Artificial Sequence
<220> FEATURE:
<223> OTHER INFORMATION: AS01311 synthesized sdAb

<400> SEQUENCE: 341

Glu Val Gln Leu Val Glu Cys Gly Gly Gly Leu Val Gln Pro Gly Gly
 1               5                   10                  15

Ser Leu Arg Leu Ser Cys Ala Ala Ser Gly Ser Ile Ala Ser Ile Asn
                20                  25                  30

Thr Met Ala Trp Tyr Arg Gln Ala Pro Gly Gln Gln Arg Glu Leu Val
            35                  40                  45

Ala Gly Ile Thr Arg Gly Gly Ser Thr Asn Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Lys Pro Glu Asp Thr Ala Val Tyr Tyr Cys Thr
                85                  90                  95
```

Asp Tyr Ser Arg Gly Tyr Tyr Gln Asp Tyr Trp Gly Gln Gly Thr Gln
                100                 105                 110

Val Thr Val Ser Ser
        115

<210> SEQ ID NO 342
<211> LENGTH: 117
<212> TYPE: PRT
<213> ORGANISM: Artificial Sequence
<220> FEATURE:
<223> OTHER INFORMATION: AS01312 synthesized sdAb

<400> SEQUENCE: 342

Glu Val Gln Leu Val Glu Cys Gly Gly Gly Leu Val Gln Pro Gly Gly
1               5                   10                  15

Ser Leu Arg Leu Ser Cys Ala Ala Ser Gly Ser Ile Ala Gly Ile Asn
            20                  25                  30

Thr Met Ala Trp Tyr Arg Gln Ala Pro Gly Gln Gln Arg Glu Leu Val
        35                  40                  45

Ala Gly Ile Thr Arg Ser Gly Ser Thr Lys Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Thr
                85                  90                  95

Asp Tyr Ser Arg Gly Tyr Tyr Gln Asp Tyr Trp Gly Gln Gly Thr Gln
                100                 105                 110

Val Thr Val Ser Ser
        115

<210> SEQ ID NO 343
<211> LENGTH: 123
<212> TYPE: PRT
<213> ORGANISM: Artificial Sequence
<220> FEATURE:
<223> OTHER INFORMATION: AS01313 synthesized sdAb

<400> SEQUENCE: 343

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Ser Ser His
            20                  25                  30

Thr Met Gly Trp Phe Arg Gln Pro Pro Gly Lys Glu Arg Glu Phe Val
        35                  40                  45

Ala Val Ile His Trp Ser Gly Ala Ser Thr Tyr Tyr Thr Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Glu Val Pro Val Ser Thr Trp Pro Pro Thr Glu Tyr Ser Trp
                100                 105                 110

Trp Gly Gln Gly Thr Gln Val Thr Val Ser Ser
        115                 120

<210> SEQ ID NO 344
<211> LENGTH: 117
<212> TYPE: PRT

<213> ORGANISM: Artificial Sequence
<220> FEATURE:
<223> OTHER INFORMATION: AS01316 synthesized sdAb

<400> SEQUENCE: 344

Glu Val Gln Leu Val Glu Cys Gly Gly Gly Leu Val Gln Pro Gly Gly
1               5                   10                  15

Ser Leu Arg Leu Ser Cys Ala Ala Ser Gly Ser Ile Ala Ser Ile Asn
            20                  25                  30

Thr Met Ala Trp Tyr Arg Gln Ala Pro Gly Gln Arg Glu Leu Val
        35                  40                  45

Ala Gly Ile Thr Arg Gly Gly Ser Thr Lys Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Thr
                85                  90                  95

Asp Phe Ser Arg Asp Tyr Tyr Gln Asp Tyr Trp Gly Gly Gly Thr Gln
            100                 105                 110

Val Thr Val Ser Ser
        115

<210> SEQ ID NO 345
<211> LENGTH: 117
<212> TYPE: PRT
<213> ORGANISM: Artificial Sequence
<220> FEATURE:
<223> OTHER INFORMATION: AS01318 synthesized sdAb

<400> SEQUENCE: 345

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Thr Met Ala Trp Tyr Arg Gln Ala Pro Gly Lys Gln Arg Glu Leu Val
        35                  40                  45

Ala Gly Ile Thr Arg Ser Gly Thr Thr Thr Tyr Ala Gly Ser Val Lys
    50                  55                  60

Gly Arg Phe Thr Ile Ser Arg Asp Asn Ala Lys Asn Thr Val Tyr Leu
65                  70                  75                  80

Gln Met Asn Gly Leu Lys Pro Glu Asp Thr Ala Val Tyr Tyr Cys Thr
                85                  90                  95

Asp Tyr Ser Ser Ser Tyr Tyr Gln Asp Tyr Trp Gly Gly Gly Thr Gln
            100                 105                 110

Val Thr Val Ser Ser
        115

<210> SEQ ID NO 346
<211> LENGTH: 117
<212> TYPE: PRT
<213> ORGANISM: Artificial Sequence
<220> FEATURE:
<223> OTHER INFORMATION: AS01320 synthesized sdAb

<400> SEQUENCE: 346

Glu Val Gln Leu Val Glu Cys Gly Gly Gly Leu Val Gln Pro Gly Gly
1               5                   10                  15

Ser Leu Arg Leu Ser Cys Ala Ala Ser Gly Ser Ile Ala Ser Ile Asn
            20                  25                  30

Thr Met Ala Trp Tyr Arg Gln Ala Pro Gly Gln Gln Arg Glu Leu Val
        35                  40                  45

Ala Gly Ile Thr Arg Gly Gly Ser Thr Lys Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Lys Pro Glu Asp Thr Ala Val Tyr Tyr Cys Thr
            85                  90                  95

Asp Tyr Ser Arg Gly Tyr Tyr Gln Asp Tyr Trp Gly Gln Gly Thr Gln
            100                 105                 110

Val Thr Val Ser Ser
        115

<210> SEQ ID NO 347
<211> LENGTH: 117
<212> TYPE: PRT
<213> ORGANISM: Artificial Sequence
<220> FEATURE:
<223> OTHER INFORMATION: AS02358 synthesized sdAb

<400> SEQUENCE: 347

Gln Val Gln Leu Val Glu Ser Gly Gly Gly Leu Val Gln Pro Gly Gly
 1               5                   10                  15

Ser Leu Arg Leu Ser Cys Ala Ala Ser Gly Ser Ile Ala Ser Ile Asn
            20                  25                  30

Thr Met Ala Trp Tyr Arg Gln Ser Pro Gly Lys Gln Arg Glu Leu Val
        35                  40                  45

Ala Gly Ile Thr Arg Gly Gly Ser Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
            85                  90                  95

Asp Tyr Ser Leu Gly Tyr Tyr Gln Asp Tyr Trp Gly Gln Gly Thr Gln
            100                 105                 110

Val Thr Val Ser Ser
        115

<210> SEQ ID NO 348
<211> LENGTH: 117
<212> TYPE: PRT
<213> ORGANISM: Artificial Sequence
<220> FEATURE:
<223> OTHER INFORMATION: AS02359 synthesized sdAb

<400> SEQUENCE: 348

Gln Val Gln Leu Val Glu Ser Gly Gly Gly Leu Val Gln Pro Gly Gly
 1               5                   10                  15

Ser Leu Arg Leu Ser Cys Ala Ala Ser Gly Ser Ile Ala Ser Ile Asn
            20                  25                  30

Thr Met Ala Trp Tyr Arg Gln Ser Pro Gly Lys Gln Arg Glu Leu Val
        35                  40                  45

Ala Gly Ile Thr Arg Gly Gly Ser Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr 85                  90                  95

Asp Tyr Ser Leu Gly Tyr Tyr Gln Asp Tyr Trp Gly Gln Gly Thr Gln
            100                 105                 110

Val Thr Val Ser Ser
        115

<210> SEQ ID NO 349
<211> LENGTH: 117
<212> TYPE: PRT
<213> ORGANISM: Artificial Sequence
<220> FEATURE:
<223> OTHER INFORMATION: AS02360 synthesized sdAb

<400> SEQUENCE: 349

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Ala Ser Ile Asn
            20                  25                  30

Thr Met Ala Trp Tyr Arg Gln Ser Pro Gly Lys Gln Arg Glu Leu Val
        35                  40                  45

Ala Gly Ile Thr Arg Gly Gly Ser Thr Asn Tyr Ala Asp Ser Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Asp Tyr Ser Leu Gly Tyr Tyr Gln Asp Tyr Trp Gly Gln Gly Thr Gln
            100                 105                 110

Val Thr Val Ser Ser
        115

<210> SEQ ID NO 350
<211> LENGTH: 117
<212> TYPE: PRT
<213> ORGANISM: Artificial Sequence
<220> FEATURE:
<223> OTHER INFORMATION: AS02362 synthesized sdAb

<400> SEQUENCE: 350

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Ala Ser Ile Asn
            20                  25                  30

Thr Met Ala Trp Tyr Arg Gln Ser Pro Gly Lys Gln Arg Glu Leu Val
        35                  40                  45

Ala Gly Ile Thr Arg Gly Gly Ser Thr Asn Tyr Ala Asp Ser Val Lys
50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Asp Tyr Ser Leu Gly Tyr Tyr Gln Asp Tyr Trp Gly Gln Gly Thr Gln
            100                 105                 110

Val Thr Val Ser Ser
        115

<210> SEQ ID NO 351
<211> LENGTH: 117

<212> TYPE: PRT
<213> ORGANISM: Artificial Sequence
<220> FEATURE:
<223> OTHER INFORMATION: AS02363 synthesized sdAb

<400> SEQUENCE: 351

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Ala Ser Ile Asn
            20                  25                  30

Thr Met Ala Trp Tyr Arg Gln Ser Pro Gly Lys Gln Arg Glu Leu Val
        35                  40                  45

Ala Gly Ile Thr Arg Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Asp Tyr Ser Leu Gly Tyr Tyr Gln Asp Tyr Trp Gly Gln Gly Thr Gln
            100                 105                 110

Val Thr Val Ser Ser
        115

<210> SEQ ID NO 352
<211> LENGTH: 117
<212> TYPE: PRT
<213> ORGANISM: Artificial Sequence
<220> FEATURE:
<223> OTHER INFORMATION: AS02365 synthesized sdAb

<400> SEQUENCE: 352

Gln Val Lys Leu Glu Glu Ser Gly Gly Gly Leu Val Gln Pro Gly Gly
1               5                   10                  15

Ser Leu Arg Leu Ser Cys Ala Ala Ser Gly Ser Ile Ala Ser Ile Asn
            20                  25                  30

Thr Met Ala Trp Tyr Arg Gln Ser Pro Gly Lys Gln Arg Glu Leu Val
        35                  40                  45

Ala Gly Ile Thr Arg Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Asp Tyr Ser Leu Gly Tyr Tyr Gln Asp Tyr Trp Gly Gln Gly Thr Gln
            100                 105                 110

Val Thr Val Ser Ser
        115

<210> SEQ ID NO 353
<211> LENGTH: 117
<212> TYPE: PRT
<213> ORGANISM: Artificial Sequence
<220> FEATURE:
<223> OTHER INFORMATION: AS01274VHa synthesized humanized sdAb

<400> SEQUENCE: 353

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Ala Ser Ile Ala

```
            20                  25                  30
Thr Met Ala Trp Tyr Arg Gln Ala Pro Gly Lys Gly Leu Glu Leu Val
        35                  40                  45

Ala Gly Ile Thr Arg Gly Gly Ser Thr Lys Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Asp Tyr Ser Arg Lys Tyr Tyr Gln Asp Tyr Trp Gly Gln Gly Thr Leu
                100                 105                 110

Val Thr Val Ser Ser
        115

<210> SEQ ID NO 354
<211> LENGTH: 117
<212> TYPE: PRT
<213> ORGANISM: Artificial Sequence
<220> FEATURE:
<223> OTHER INFORMATION: AS01299VH3a synthesized humanized sdAb

<400> SEQUENCE: 354

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Ala
            20                  25                  30

Thr Met Ala Trp Tyr Arg Gln Ala Pro Gly Lys Gly Leu Glu Leu Val
        35                  40                  45

Ala Gly Ile Thr Arg Ser Gly Ser Thr Asn Tyr Arg Asp Ser Val Lys
    50                  55                  60

Gly Arg Phe Thr Ile Ser Arg Asp Asn Ser Lys Asn Thr Met Tyr Leu
65                  70                  75                  80

Gln Met Asn Ser Leu Arg Ala Glu Asp Thr Ala Val Tyr Tyr Cys Thr
                85                  90                  95

Asp Tyr Ser Ser Arg Tyr Tyr His Asp Tyr Trp Gly Gln Gly Thr Leu
                100                 105                 110

Val Thr Val Ser Ser
        115

<210> SEQ ID NO 355
<211> LENGTH: 117
<212> TYPE: PRT
<213> ORGANISM: Artificial Sequence
<220> FEATURE:
<223> OTHER INFORMATION: AS01274Vha-A49 synthesized humanized sdAb

<400> SEQUENCE: 355

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Ala Ser Ile Ala
            20                  25                  30

Thr Met Ala Trp Tyr Arg Gln Ala Pro Gly Lys Gly Leu Glu Leu Val
        35                  40                  45

Ser Gly Ile Thr Arg Gly Gly Ser Thr Lys Tyr Ala Asp Ser Val Lys
    50                  55                  60

Gly Arg Phe Thr Ile Ser Arg Asp Asn Ser Lys Asn Thr Leu Tyr Leu
65                  70                  75                  80
```

```
Gln Met Asn Ser Leu Arg Ala Glu Asp Thr Ala Val Tyr Tyr Cys Thr
                85                  90                  95

Asp Tyr Ser Arg Lys Tyr Tyr Gln Asp Tyr Trp Gly Gln Gly Thr Leu
            100                 105                 110

Val Thr Val Ser Ser
        115

<210> SEQ ID NO 356
<211> LENGTH: 117
<212> TYPE: PRT
<213> ORGANISM: Artificial Sequence
<220> FEATURE:
<223> OTHER INFORMATION: AS01299VH3a-A49 synthesized humanized sdAb

<400> SEQUENCE: 356

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Ala
            20                  25                  30

Thr Met Ala Trp Tyr Arg Gln Ala Pro Gly Lys Gly Leu Glu Leu Val
        35                  40                  45

Ser Gly Ile Thr Arg Ser Gly Ser Thr Asn Tyr Arg Asp Ser Val Lys
    50                  55                  60

Gly Arg Phe Thr Ile Ser Arg Asp Asn Ser Lys Asn Thr Met Tyr Leu
65                  70                  75                  80

Gln Met Asn Ser Leu Arg Ala Glu Asp Thr Ala Val Tyr Tyr Cys Thr
                85                  90                  95

Asp Tyr Ser Arg Tyr Tyr His Asp Tyr Trp Gly Gln Gly Thr Leu
            100                 105                 110

Val Thr Val Ser Ser
        115

<210> SEQ ID NO 357
<211> LENGTH: 117
<212> TYPE: PRT
<213> ORGANISM: Artificial Sequence
<220> FEATURE:
<223> OTHER INFORMATION: AS01299VH3a-L47 synthesized humanized sdAb

<400> SEQUENCE: 357

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Ala
            20                  25                  30

Thr Met Ala Trp Tyr Arg Gln Ala Pro Gly Lys Gly Leu Glu Trp Val
        35                  40                  45

Ala Gly Ile Thr Arg Ser Gly Ser Thr Asn Tyr Arg Asp Ser Val Lys
    50                  55                  60

Gly Arg Phe Thr Ile Ser Arg Asp Asn Ser Lys Asn Thr Met Tyr Leu
65                  70                  75                  80

Gln Met Asn Ser Leu Arg Ala Glu Asp Thr Ala Val Tyr Tyr Cys Thr
                85                  90                  95

Asp Tyr Ser Arg Tyr Tyr His Asp Tyr Trp Gly Gln Gly Thr Leu
            100                 105                 110

Val Thr Val Ser Ser
        115

<210> SEQ ID NO 358
```

<211> LENGTH: 117
<212> TYPE: PRT
<213> ORGANISM: Artificial Sequence
<220> FEATURE:
<223> OTHER INFORMATION: AS01299VH3a-M78 synthesized humanized sdAb

<400> SEQUENCE: 358

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Ala
            20                  25                  30

Thr Met Ala Trp Tyr Arg Gln Ala Pro Gly Lys Gly Leu Glu Leu Val
        35                  40                  45

Ala Gly Ile Thr Arg Ser Gly Ser Thr Asn Tyr Arg Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Asp Tyr Ser Ser Arg Tyr Tyr His Asp Tyr Trp Gly Gln Gly Thr Leu
            100                 105                 110

Val Thr Val Ser Ser
        115
```

<210> SEQ ID NO 359
<211> LENGTH: 117
<212> TYPE: PRT
<213> ORGANISM: Artificial Sequence
<220> FEATURE:
<223> OTHER INFORMATION: AS01299VH4 synthesized humanized sdAb

<400> SEQUENCE: 359

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Ala
            20                  25                  30

Thr Met Ala Trp Tyr Arg Gln Ala Pro Gly Lys Gly Leu Glu Leu Val
        35                  40                  45

Ser Gly Ile Thr Arg Ser Gly Ser Thr Asn Tyr Arg Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Asp Tyr Ser Ser Arg Tyr Tyr His Asp Tyr Trp Gly Gln Gly Thr Leu
            100                 105                 110

Val Thr Val Ser Ser
        115
```

<210> SEQ ID NO 360
<211> LENGTH: 117
<212> TYPE: PRT
<213> ORGANISM: Artificial Sequence
<220> FEATURE:
<223> OTHER INFORMATION: AS01299VH4-L47 synthesized humanized sdAb

<400> SEQUENCE: 360

```
Glu Val Gln Leu Val Glu Ser Gly Gly Gly Leu Val Gln Pro Gly Gly
1               5                   10                  15
```

-continued

```
Ser Leu Arg Leu Ser Cys Ala Ala Ser Gly Ser Ile Phe Ser Ile Ala
            20                  25                  30

Thr Met Ala Trp Tyr Arg Gln Ala Pro Gly Lys Gly Leu Glu Trp Val
        35                  40                  45

Ser Gly Ile Thr Arg Ser Gly Ser Thr Asn Tyr Arg Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Asp Tyr Ser Ser Arg Tyr Tyr His Asp Tyr Trp Gly Gln Gly Thr Leu
            100                 105                 110

Val Thr Val Ser Ser
        115

<210> SEQ ID NO 361
<211> LENGTH: 45
<212> TYPE: DNA
<213> ORGANISM: Artificial Sequence
<220> FEATURE:
<223> OTHER INFORMATION: p441_VHHF1 synthesized primer

<400> SEQUENCE: 361
gcccagccgg ccatggccsm bgtrcagctg gtggaktctg gggga            45

<210> SEQ ID NO 362
<211> LENGTH: 45
<212> TYPE: DNA
<213> ORGANISM: Artificial Sequence
<220> FEATURE:
<223> OTHER INFORMATION: p442_VHHF2 synthesized primer

<400> SEQUENCE: 362
gcccagccgg ccatggccca ggtaaagctg gaggagtctg gggga            45

<210> SEQ ID NO 363
<211> LENGTH: 39
<212> TYPE: DNA
<213> ORGANISM: Artificial Sequence
<220> FEATURE:
<223> OTHER INFORMATION: p759_VHHF3 synthesized primer

<400> SEQUENCE: 363
gcccagccgg ccatggccca ggtacagctg gtggagtct                   39

<210> SEQ ID NO 364
<211> LENGTH: 41
<212> TYPE: DNA
<213> ORGANISM: Artificial Sequence
<220> FEATURE:
<223> OTHER INFORMATION: p444_VHHF4 synthesized primer

<400> SEQUENCE: 364
gcccagccgg ccatggccga ggtgcagctg gtggagtgtg g                41

<210> SEQ ID NO 365
<211> LENGTH: 21
<212> TYPE: DNA
```

```
<213> ORGANISM: Artificial Sequence
<220> FEATURE:
<223> OTHER INFORMATION: p445_CH2R synthesized primer

<400> SEQUENCE: 365
cgccatcaag gtaccagttg a                                           21

<210> SEQ ID NO 366
<211> LENGTH: 29
<212> TYPE: DNA
<213> ORGANISM: Artificial Sequence
<220> FEATURE:
<223> OTHER INFORMATION: p446_CH2b3R synthesized primer

<400> SEQUENCE: 366
ggggtacctg tcatccacgg accagctga                                   29

<210> SEQ ID NO 367
<211> LENGTH: 34
<212> TYPE: DNA
<213> ORGANISM: Artificial Sequence
<220> FEATURE:
<223> OTHER INFORMATION: p440_VHHF synthesized primer

<400> SEQUENCE: 367
catgtgtaga ctcgcggccc agccggccat ggcc                             34

<210> SEQ ID NO 368
<211> LENGTH: 46
<212> TYPE: DNA
<213> ORGANISM: Artificial Sequence
<220> FEATURE:
<223> OTHER INFORMATION: p447_VHHR synthesized primer

<400> SEQUENCE: 368
catgtgtaga ttcctggccg gcctggcctg aggagacggt gacctg                46
```